(12) United States Patent
Hofstadler et al.

(10) Patent No.: US 7,714,275 B2
(45) Date of Patent: May 11, 2010

(54) MASS SPECTROMETRY WITH SELECTIVE ION FILTRATION BY DIGITAL THRESHOLDING

(75) Inventors: Steven A. Hofstadler, Vista, CA (US); Jared J. Drader, Carlsbad, CA (US); Amy L. Schink, Carlsbad, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 339 days.

(21) Appl. No.: 11/136,134

(22) Filed: May 24, 2005

(65) Prior Publication Data

US 2005/0270191 A1    Dec. 8, 2005

Related U.S. Application Data

(60) Provisional application No. 60/574,042, filed on May 24, 2004.

(51) Int. Cl.
*H01J 49/44* (2006.01)
(52) U.S. Cl. .................. 250/282; 250/281; 250/288
(58) Field of Classification Search .................. 250/282
See application file for complete search history.

(56) References Cited

U.S. PATENT DOCUMENTS

| | | | |
|---|---|---|---|
| 4,075,475 A | 2/1978 | Risby et al. | |
| 4,683,195 A | 7/1987 | Mullis et al. | |
| 4,683,202 A | 7/1987 | Mullis et al. | |
| 4,965,188 A | 10/1990 | Mullis et al. | |
| 5,015,845 A | 5/1991 | Allen et al. | |
| 5,072,115 A * | 12/1991 | Zhou ............... | 250/281 |
| 5,213,961 A | 5/1993 | Bunn et al. | |
| 5,219,727 A | 6/1993 | Wang et al. | |
| 5,436,129 A | 7/1995 | Stapleton | |
| 5,451,500 A | 9/1995 | Stapleton | |
| 5,472,843 A | 12/1995 | Milliman | |
| 5,476,774 A | 12/1995 | Wang et al. | |
| 5,484,908 A | 1/1996 | Froehler et al. | |
| 5,502,177 A | 3/1996 | Matteucci et al. | |
| 5,503,980 A | 4/1996 | Cantor | |
| 5,504,327 A | 4/1996 | Sproch et al. | |
| 5,504,329 A | 4/1996 | Mann et al. | |
| 5,523,217 A | 6/1996 | Lupski et al. | |
| 5,527,675 A | 6/1996 | Coull et al. | |

(Continued)

FOREIGN PATENT DOCUMENTS

AU         2003245488         6/2002

(Continued)

OTHER PUBLICATIONS

Loo, J. A. et al., "Applying Charge Discrimination with Electrospray Ionization-Mass Spectrometry to Protein Analyses," *J. Am. Soc. Mass. Spectrom.* (1995) 6:1098-1104.

(Continued)

*Primary Examiner*—David A. Vanore
(74) *Attorney, Agent, or Firm*—Casimir Jones S.C.

(57) ABSTRACT

The methods described herein generally relate to characterization of large analytes, such as biomolecules, by molecular mass analysis. Specifically, the methods are directed to molecular mass analysis of singly- or multiply-charged ions by selective ion filtering carried out by a digital thresholding process.

38 Claims, 8 Drawing Sheets

U.S. PATENT DOCUMENTS

Figure 1:
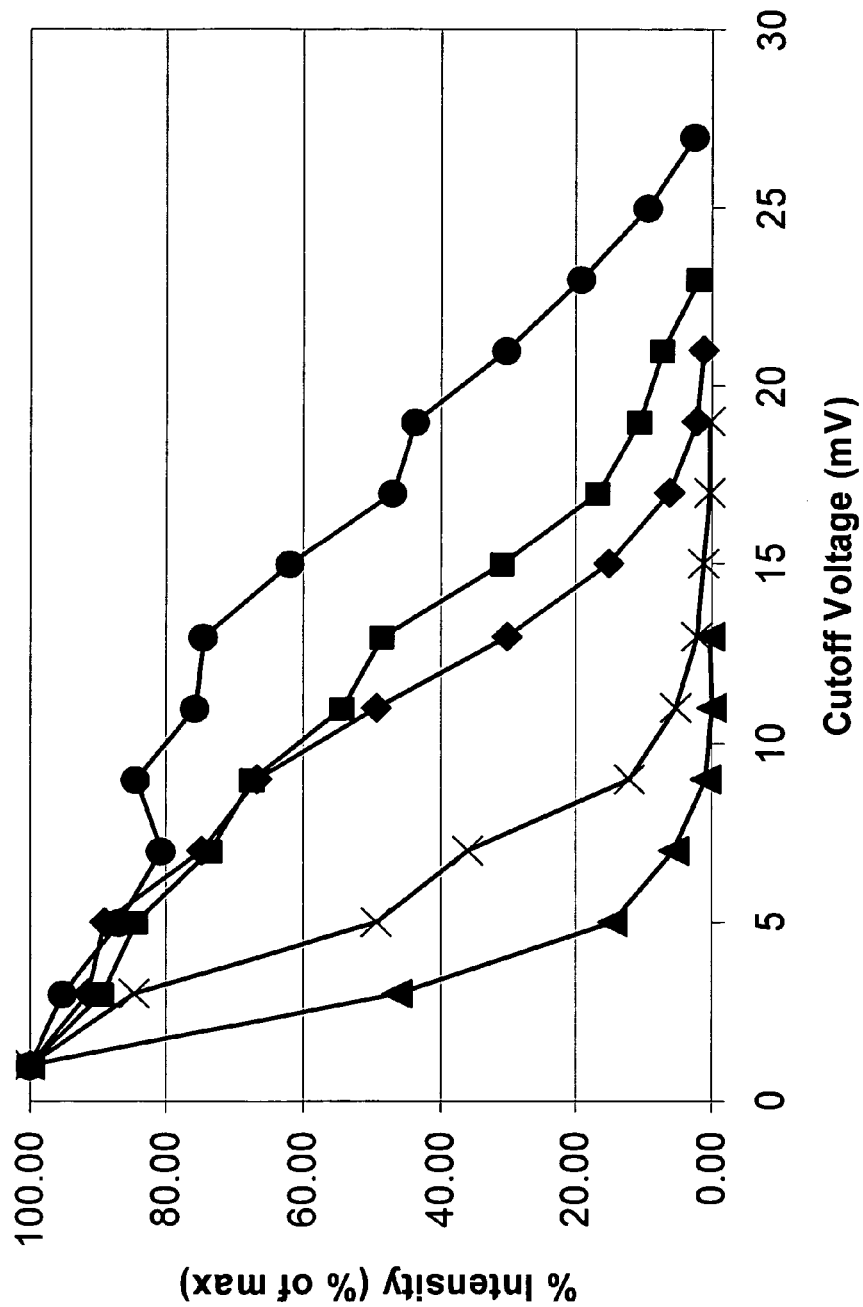

| | | |
|---|---|---|
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,645,985 A | 7/1997 | Froehler et al. |
| 5,683,869 A | 11/1997 | Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Uhlen |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,828,062 A | 10/1998 | Jarrell et al. |
| 5,830,653 A | 11/1998 | Froehler et al. |
| 5,830,655 A | 11/1998 | Monforte et al. |
| 5,832,489 A | 11/1998 | Kucala |
| 5,834,255 A | 11/1998 | van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,885,775 A | 3/1999 | Haff et al. |
| 5,928,905 A | 7/1999 | Stemmer et al. |
| 5,928,906 A | 7/1999 | Koster |
| 5,965,363 A | 10/1999 | Monforte et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,028,183 A | 2/2000 | Lin et al. |
| 6,043,031 A | 3/2000 | Koster et al. |
| 6,046,005 A | 4/2000 | Ju |
| 6,051,378 A | 4/2000 | Monforte et al. |
| 6,054,278 A | 4/2000 | Dodge et al. |
| 6,055,487 A | 4/2000 | Margery et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,194,114 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz |
| 6,270,973 B1 | 8/2001 | Lewis et al. |
| 6,270,974 B1 | 8/2001 | Shultz et al. |
| 6,274,726 B1 | 8/2001 | Laugharn, Jr. et al. |
| 6,277,573 B1 | 8/2001 | Koster et al. |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,939,387 B2 | 5/2002 | Tang et al. |
| 6,419,932 B1 | 7/2002 | Dale |
| 6,423,986 B1 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner et al. |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton et al. |

| | | |
|---|---|---|
| 6,613,509 B1 | 9/2003 | Chen |
| 6,613,520 B2 | 9/2003 | Ashby et al. |
| 6,623,928 B2 | 9/2003 | Van Ness et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,716,634 B1 | 4/2004 | Myerson |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,217,510 B2 | 5/2007 | Ecker et al. |
| 7,226,739 B2 | 8/2007 | Ecker et al. |
| 7,255,992 B2 | 8/2007 | Ecker et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150903 A1 | 10/2002 | Koster et al. |
| 2002/0150927 A1 | 10/2002 | Matray et al. |
| 2002/0168630 A1 | 11/2002 | Fleming et al. |
| 2003/0017487 A1 | 1/2003 | Xue et al. |
| 2003/0027135 A1 | 2/2003 | Ecker et al. |
| 2003/0039976 A1 | 2/2003 | Haff et al. |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0082539 A1 | 5/2003 | Ecker et al. |
| 2003/0101172 A1 | 5/2003 | Ecker et al. |
| 2003/0104410 A1 | 6/2003 | Mittmann |
| 2003/0113745 A1 | 6/2003 | Monforte et al. |
| 2003/0119018 A1 | 6/2003 | Omura et al. |
| 2003/0124556 A1 | 7/2003 | Ecker et al. |
| 2003/0129589 A1 | 7/2003 | Koster et al. |
| 2003/0134312 A1 | 7/2003 | Burgoyne et al. |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228613 A1 | 12/2003 | Bornarth et al. |
| 2004/0005555 A1 | 1/2004 | Rothman et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038234 A1 | 2/2004 | Gut et al. |
| 2004/0038385 A1 | 2/2004 | Langlois et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0013703 A1 | 7/2004 | Katinger et al. |
| 2004/0126764 A1 | 7/2004 | Lasken et al. |
| 2004/0161770 A1 | 8/2004 | Ecker et al. |
| 2004/0180328 A1 | 9/2004 | Ecker et al. |
| 2004/0185438 A1 | 9/2004 | Ecker et al. |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130216 A1 | 6/2005 | Becker et al. |
| 2005/0250125 A1 | 11/2005 | Novakoff |
| 2005/0266397 A1 | 12/2005 | Ecker et al. |
| 2006/0020391 A1 | 1/2006 | Kreiswirth et al. |
| 2006/0121520 A1 | 6/2006 | Ecker et al. |
| 2006/0259249 A1 | 11/2006 | Sampath et al. |
| 2006/0275788 A1 | 12/2006 | Ecker et al. |
| 2007/0048735 A1 | 3/2007 | Ecker et al. |
| 2007/0218467 A1 | 9/2007 | Ecker et al. |
| 2008/0160512 A1 | 7/2008 | Ecker et al. |
| 2009/0004643 A1 | 1/2009 | Ecker et al. |

FOREIGN PATENT DOCUMENTS

| | | |
|---|---|---|
| AU | 2003282352 | 11/2002 |
| CN | 1202204 | 12/1998 |
| DE | 19732086 | 1/1999 |
| DE | 19802905 | 7/1999 |
| DE | 19824280 | 12/1999 |
| DE | 19852167 | 5/2000 |
| DE | 19943374 | 3/2001 |
| DE | 10132147 | 2/2003 |
| EP | 0281390 | 9/1988 |
| EP | 0620862 | 10/1994 |
| EP | 1035219 | 9/2000 |
| EP | 1138782 | 10/2001 |
| EP | 1234888 | 8/2002 |
| EP | 02709785 | 9/2002 |
| EP | 02709785.2 | 9/2002 |
| EP | 1308506 | 5/2003 |
| EP | 1310571 | 5/2003 |
| EP | 1333101 | 8/2003 |
| EP | 1365031 | 11/2003 |
| EP | 1748072 | 1/2007 |
| FR | 2811321 | 1/2002 |
| GB | 2325002 | 11/1998 |

| | | |
|---|---|---|
| GB | 2339905 | 2/2000 |
| IN | 01136 | 2/2003 |
| JP | 5-276999 | 10/1993 |
| JP | 2004-200 | 1/2004 |
| JP | 2004-24206 | 1/2004 |
| JP | 2004-201641 | 7/2004 |
| JP | 2004-201679 | 7/2004 |
| WO | WO 88/003957 | 6/1988 |
| WO | WO 90/015157 | 12/1990 |
| WO | WO 92/008117 | 5/1992 |
| WO | WO 92/05182 | 11/1992 |
| WO | WO 92/19774 | 11/1992 |
| WO | WO 93/003186 | 2/1993 |
| WO | WO 93/008297 | 4/1993 |
| WO | WO 95/004161 | 2/1994 |
| WO | WO 94/016101 | 7/1994 |
| WO | WO 94/019490 | 9/1994 |
| WO | WO 94/021822 | 9/1994 |
| WO | WO 95/011996 | 5/1995 |
| WO | WO 95/013395 | 5/1995 |
| WO | WO 95/013396 | 5/1995 |
| WO | WO 95/031997 | 11/1995 |
| WO | WO 96/016186 | 5/1996 |
| WO | WO 96/029431 | 9/1996 |
| WO | WO 96/032504 | 10/1996 |
| WO | WO 96/037630 | 11/1996 |
| WO | WO 97/033000 | 9/1997 |
| WO | WO 97/034909 | 9/1997 |
| WO | WO 97/037041 | 10/1997 |
| WO | WO 97/47766 | 12/1997 |
| WO | WO 98/003684 | 1/1998 |
| WO | WO 98/012355 | 3/1998 |
| WO | WO 98/014616 | 4/1998 |
| WO | WO 98/015652 | 4/1998 |
| WO | WO 98/020020 | 5/1998 |
| WO | WO 98/020157 | 5/1998 |
| WO | WO 98/020166 | 5/1998 |
| WO | WO 98/026095 | 6/1998 |
| WO | WO 98/031830 | 7/1998 |
| WO | WO 98/035057 | 8/1998 |
| WO | WO 98/040520 | 9/1998 |
| WO | WO 98/054751 | 12/1998 |
| WO | WO 99/005319 | 2/1999 |
| WO | WO 99/012040 | 3/1999 |
| WO | WO 99/013104 | 3/1999 |
| WO | WO 99/014375 | 3/1999 |
| WO | WO 99/029898 | 6/1999 |
| WO | WO 99/031278 | 6/1999 |
| WO | WO 00/063362 | 10/1999 |
| WO | WO 99/057318 | 11/1999 |
| WO | WO 99/058713 | 11/1999 |
| WO | WO 99/60183 | 11/1999 |
| WO | WO 00/066789 | 11/2000 |
| WO | WO 01/007648 | 2/2001 |
| WO | WO 01/012853 | 2/2001 |
| WO | WO 01/023604 | 4/2001 |
| WO | WO 01/023608 | 4/2001 |
| WO | WO 01/032930 | 5/2001 |
| WO | WO 01/040497 | 6/2001 |
| WO | WO 01/046404 | 6/2001 |
| WO | WO 01/051661 | 7/2001 |
| WO | WO 01/051662 | 7/2001 |
| WO | WO 01/057263 | 8/2001 |
| WO | WO 01/057518 | 8/2001 |
| WO | WO 01/073119 | 10/2001 |
| WO | WO 01/073199 | 10/2001 |
| WO | WO 01/077392 | 10/2001 |
| WO | WO 02/002811 | 1/2002 |
| WO | WO 02/010186 | 2/2002 |
| WO | WO 02/010444 | 2/2002 |
| WO | WO 02/018641 | 3/2002 |
| WO | WO 02/021108 | 3/2002 |
| WO | WO 02/022873 | 3/2002 |
| WO | WO 02/024876 | 3/2002 |
| WO | WO 02/050307 | 6/2002 |
| WO | WO 02/057491 | 7/2002 |
| WO | WO 02/070664 | 9/2002 |
| WO | WO 02/070728 | 9/2002 |
| WO | WO 02/077278 | 10/2002 |
| WO | WO 02/099034 | 12/2002 |
| WO | WO 02/099095 | 12/2002 |
| WO | WO 02/099129 | 12/2002 |
| WO | WO 02/099130 | 12/2002 |
| WO | WO 03/002750 | 1/2003 |
| WO | WO 03/008636 | 1/2003 |
| WO | WO 03/012058 | 2/2003 |
| WO | WO 03/012074 | 2/2003 |
| WO | WO 03/014382 | 2/2003 |
| WO | WO 03/016546 | 2/2003 |
| WO | WO 03/020890 | 3/2003 |
| WO | WO 03/033732 | 4/2003 |
| WO | WO 03/054162 | 7/2003 |
| WO | WO 03/054755 | 7/2003 |
| WO | WO 03/060163 | 7/2003 |
| WO | WO 03/075955 | 9/2003 |
| WO | WO 03/088979 | 10/2003 |
| WO | WO 03/093506 | 11/2003 |
| WO | WO 03/097869 | 11/2003 |
| WO | WO 03/100035 | 12/2003 |
| WO | WO 03/100068 | 12/2003 |
| WO | WO 03/104410 | 12/2003 |
| WO | WO 2004/003511 | 1/2004 |
| WO | WO 2004/011651 | 2/2004 |
| WO | WO 2004/040013 | 5/2004 |
| WO | WO 2004/044123 | 5/2004 |
| WO | WO 2004/044247 | 5/2004 |
| WO | WO 2004/052175 | 6/2004 |
| WO | WO 2004/060278 | 7/2004 |
| WO | WO 2004/070001 | 8/2004 |
| WO | WO 2004/072230 | 8/2004 |
| WO | WO 2004/072231 | 8/2004 |
| WO | WO 2004/101809 | 11/2004 |
| WO | WO 2005/003384 | 1/2005 |
| WO | WO 2005/012572 | 2/2005 |
| WO | WO 2005/024046 | 3/2005 |
| WO | WO 2005/053141 | 6/2005 |
| WO | WO 2005/054454 | 6/2005 |
| WO | WO 2005/075686 | 10/2005 |
| WO | WO 2005/091971 | 10/2005 |
| WO | WO 2005/098047 | 10/2005 |
| WO | WO 2006/089762 | 8/2006 |
| WO | WO 2006/094238 | 9/2006 |
| WO | WO 2006/116127 | 11/2006 |
| WO | WO 2008/118809 | 10/2008 |
| WO | WO 98/054571 | 12/2008 |

OTHER PUBLICATIONS

Ecker et al. U.S. Appl. No. 90/010,209 (Re-exam), filed Jun. 27, 2008.

Ecker et al. U.S. Appl. No. 90/010,210 (Re-exam), filed Jun. 27, 2008.

U.S. Appl. No. 90/010,209, filing date Mar. 25, 2008, Kreiswirth et al.

U.S. Appl. No. 90/010,210, filling date Jun. 27, 2008, Ecker et al.

Aaserud et al., "Accurate base composition of double-strand DNA by mass spectrometry" *J. Am. Soc. Spec.* (1996) 7:1266-1269.

Aaserud et al., "DNA sequencing with balckbody infrared radioactive dissociation of electrosprayed ions" Int. J. Mass. Spectrom. Ion Processes, (1997) 167-168: 705-712 (Reference not found in.

Adam et al., Molecular structure of the two-dimensional hexon crystalline array and of adenovirus capsid: *Acta Microbiol. Immuno. Hung.* (1998) 45:305-310.

Adam et al., "Intertype specific epitope structure of adenovirus hexon" *Acta Microbiol. Immuno. Hung.* (1998) 45:311-316.

Adam et al., " Characterization of intertype specific epitopes on adenovirus hexons" *Arch. Virol.* (1998) 143:1669-1682.

Adrian et al., "DNA restriction analysis of adenovirus prototypes 1 to 41" *Arch. Virol.* (1986) 91:277290.

Adzhar et al., "Universal oligonucleotides for the detection of infectious bronchitis virus by the polymerase chain reaction" Avian Pathology (1996) 25:817-836.

Akalu et al., " Rapid identification of subgenera of human adenovirus by serological and PCR assays" *J. Virol Methods* (1998) 71:187-196.

Allaouchiche et al., "Clinical Impact of Rapid Oxacillin Susceptibility Testing Using a PCR Assay in Staphylococcus aureus Bactaeremia" J. Infect. (1999) 39(3):198-204.

Allawi, H.T. & Santa Lucia J., Jr. Thermodynamics and Nmr of internal G.T. mismatches in DNA, Biochemistry, 36, 10581-94 (1997).

Altschuel et al., J. Mol. Biol., 215, 403-410 (1990).

Altschul et al., Nucl. Acid Res., 25:3389-3402 (1997).

Alves-Silva, J. et al., "The Ancestry of Brazilian mtDNA Lineages," Am. J. Hum. Genet. (2000) 67:444-461.

Amano et al., "Detection of influenza virus: traditional approaches and development of biosensors" Anal. Bioanal. Chem. (2005) 381:156-164.

Amexis et al., "Quantitiative mutant analysis of viral quasispecies by chip-based matrix-assisted laser desorption/ionization of time-of-flight mass spectrometry" Pnas (2001) 98(21):12097-12102; Correction: 98(24):14186.

Anderson et al., "Sequence and organization of the human mitochondrial genome," *Nature* (1981) 290:457-465.

Anderson and Young, Quantitative Filter Hybridization in Nucleic Acid Hybridization (1985).

Andreasson et al., "Mitochondrial Sequence Analysis for Forensic Identification Using Pyrosequencing Technology" *Bio Techniques* (2002) 32:124-133.

Anthony et al., "Use of the Polymerase Chain Reaction for Rapid Detection of High-Level Mupirocin Resistance in Staphylococci" Eur. J. Clin. Microbiol. Infect. Dis. (1999) 18(1):30-34.

Application for Grant by David Mitchell Lubmann dated Oct. 25, 1992 and Oct. 29, 1992.

Application for Continuation Grant by David Mitchell Lubmann dated Jun. 10, 1994 and Jun. 24, 1994.

Application for Grant by David Mitchell Lubmann dated Sep. 1, 1994 and Sep. 27, 1994.

Application for Continuation Grant by David Mitchell Lubmann dated Jun, 4, 1996 and Jun. 14, 1996.

U.S. Appl. No. 09/798,007 Office Communication Mailed Apr. 16, 2002.

U.S. Appl. No. 09/798,007 Office Communication Mailed Jun. 20, 2002.

U.S. Appl. No. 09/798,007 Office Communication Mailed Nov. 6, 2002.

U.S. Appl. No. 09/798,007 Office Communication Mailed Jan. 8, 2003.

U.S. Appl. No. 09/798,007 Office Communication Mailed Jan. 31, 2003.

U.S. Appl. No. 09/798,007 Office Communication Mailed Feb. 27, 2003.

U.S. Appl. No. 09/798,007 Office Communication Mailed May 20, 2003.

U.S. Appl. No. 09/798,007 Office Communication Mailed May 28, 2003.

U.S. Appl. No. 09/798,007 Office Communication Mailed Jul. 11, 2003.

U.S. Appl. No. 09/798,007 Office Communication Mailed Sep. 22, 2003.

U.S. Appl. No. 09/798,007 Office Communication Mailed Nov. 19, 2003.

U.S. Appl. No. 09/798,007 Office Communication Mailed Jun. 30, 2004.

U.S. Appl. No. 09/798,007 Office Communication Mailed Aug. 10, 2004.

U.S. Appl. No. 09/798,007 Office Communication Mailed Feb. 10, 2005.

U.S. Appl. No. 09/891,793 Office Communication Mailed Dec. 18, 2002.

U.S. Appl. No. 09/891,793 Office Communication Mailed May 19, 2003 interview summary report.

U.S. Appl. No. 09/891,793 Office Communication Mailed May 23, 2003.

U.S. Appl. No. 09/891,793 Office Communication Mailed Aug. 26, 2003.

U.S. Appl. No. 09/891,793 Office Communication Mailed Nov. 13, 2003.

U.S. Appl. No. 09/891,793 Office Communication Mailed Mar. 9, 2004.

U.S. Appl. No. 09/891,793 Office Communication Mailed Jun. 14, 2004.

U.S. Appl. No. 09/891,793 Office Communication Mailed Jul. 13, 2004.

U.S. Appl. No. 09/891,793 Office Communication Mailed Aug. 10, 2004.

U.S. Appl. No. 09/891,793 Office Communication Mailed Oct. 20, 2004.

U.S. Appl. No. 09/891,793 Office Communication Mailed Mar. 8, 2005.

U.S. Appl. No. 09/891,793 Office Communication Mailed May 19, 2005.

U.S. Appl. No. 09/891,793 Office Communication Mailed Aug. 11, 2005.

U.S. Appl. No. 09/891,793 Office Communication Mailed Mar. 16, 2006.

U.S. Appl. No. 09/891,793 Office Communication Mailed Jul. 12, 2006.

U.S. Appl. No. 09/891,793 Office Communication Mailed Sep. 13, 2006.

U.S. Appl. No. 09/891,793 Office Communication Mailed Nov. 20, 2006.

U.S. Appl. No. 09/891,793 Office Communication Mailed Jul. 22, 2008.

U.S. Appl. No. 10/156,608 Office Communication Mailed Apr. 1, 2004.

U.S. Appl. No. 10/156,608 Office Communication Mailed Aug. 10, 2004.

U.S. Appl. No. 10/156,608 Office Communication Mailed Oct. 14, 2004.

U.S. Appl. No.10/156,608 Office Communication Mailed Nov. 19, 2004.

U.S. Appl. No. 10/156,608 Office Communication Mailed Dec. 9, 2004.

U.S. Appl. No. 10/156,608 Office Communication Mailed May 23, 2005.

U.S. Appl. No. 10/156,608 Office Communication Mailed May 26, 2005.

U.S. Appl. No. 10/156,608 Office Communication Mailed Jul. 20, 2005.

U.S. Appl. No. 10/156,608 Office Communication Mailed Sep. 15, 2005.

U.S. Appl. No. 10/156,608 Office Communication Mailed Jun. 2, 2006.

U.S. Appl. No. 10/323,438 Office Communication Mailed Nov. 20, 2003.

U.S. Appl. No. 10/323,438 Office Communication Mailed Jul. 26, 2004.

U.S. Appl. No. 10/325,527 Office Communication Mailed Dec. 3, 2003.

U.S. Appl. No. 10/325,527 Office Communication Mailed Aug. 16, 2004.

U.S. Appl. No. 10/325,527 Office Communication Mailed Mar. 11, 2005.

U.S. Appl. No. 10/326,642 Office Communication Mailed Nov. 21, 2003.

U.S. Appl. No. 10/326,642 Office Communication Mailed Jul. 14, 2004.

U.S. Appl. No. 10/418,514 Office Communication Mailed Sep. 29, 2005.

U.S. Appl. No. 10/418,514 Office Communication Mailed Feb. 27, 2006.

U.S. Appl. No. 10/418,514 Office Communication Mailed Mar. 27, 2007.
U.S. Appl. No. 10/418,514 Office Communication Mailed Dec. 6, 2007.
U.S. Appl. No. 10/418,514 Office Communication Mailed Apr. 15, 2008.
U.S. Appl. No. 10/418,514 Office Communication Mailed Jul. 1, 2008.
U.S. Appl. No. 10/660,122 Office Communication Mailed Mar. 17, 2006.
U.S. Appl. No. 10/660,122 Office Communication Mailed Jul. 6, 2006.
U.S. Appl. No. 10/660,122 Office Communication Mailed Sep. 19, 2006.
U.S. Appl. No. 10/660,122 Office Communication Mailed Apr. 20, 2007.
U.S. Appl. No. 10/660,122 Office Communication Mailed Sep. 19, 2007.
U.S. Appl. No. 10/660,122 Office Communication Mailed Mar. 21, 2008.
U.S. Appl. No. 10/660,122 Office Communication Mailed Jul. 9, 2008.
U.S. Appl. No. 10/660,122 Office Communication Mailed Sep. 17, 2008.
U.S. Appl. No. 10/660,996 Office Communication Mailed Feb. 28, 2006.
U.S. Appl. No.10/660,996 Office Communication Mailed May 30, 2006.
U.S. Appl. No. 10/660,996 Office Communication Mailed Jul. 12, 2006.
U.S. Appl. No. 10/660,996 Office Communication Mailed Sep. 5, 2006.
U.S. Appl. No. 10/660,996 Office Communication Mailed Nov. 22, 2006.
U.S. Appl. No. 10/660,996 Office Communication Mailed Jul. 10, 2007 with associated Information Disclosure Statement filed Feb. 21, 2007.
U.S. Appl. No. 10/660,997 Office Communication Mailed Mar. 13, 2006.
U.S. Appl. No. 10/660,997 Office Communication Mailed May 26, 2006.
U.S. Appl. No. 10/660,997 Office Communication Mailed Sep. 18, 2006.
U.S. Appl. No. 10/660,997 Office Communication Mailed Nov. 21, 2006.
U.S. Appl. No. 10/660,998 Office Communication Mailed May 1, 2006.
U.S. Appl. No. 10/660,998 Office Communication Mailed Aug. 3, 2006.
U.S. Appl. No. 10/660,998 Office Communication Mailed Jan. 24, 2007.
U.S. Appl. No. 10/660,998 Office Communication Mailed Aug. 7, 2007.
U.S. Appl. No. 10/660,998 Office Communication Mailed Dec. 11, 2007.
U.S. Appl. No. 10/660,998 Office Communication Mailed Sep. 19, 2008.
U.S. Appl. No. 10/660,998 Office Communication Mailed Apr. 7, 2009.
U.S. Appl. No. 10/728,486 Office Communication Mailed Apr. 10, 2006.
U.S. Appl. No. 10/728,486 Office Communication Mailed Jul. 27, 2006.
U.S. Appl. No. 10/728,486 Office Communication Mailed Oct. 17, 2007.
U.S. Appl. No. 10/728,486 Office Communication Mailed Dec. 20, 2006.
U.S. Appl. No. 10/728,486 Office Communication Mailed May 11, 2007.
U.S. Appl. No. 10/728,486 Office Communication Mailed Jan. 23, 2008.
U.S. Appl. No. 10/728,486 Office Communication Mailed Nov. 3, 2008.
U.S. Appl. No. 10/754,415 Office Communication Mailed Mar. 13, 2006.
U.S. Appl. No. 10/754,415 Office Communication Mailed Aug. 28, 2006.
U.S. Appl. No. 10/754,415 Office Communication Mailed Nov. 17, 2006.
U.S. Appl. No. 10/754,415 Office Communication Mailed Feb. 27, 2007.
U.S. Appl. No. 10/754,415 Office Communication Mailed Aug. 30, 2007.
U.S. Appl. No. 10/754,415 Office Communication Mailed Oct. 10. 2007.
U.S. Appl. No. 10/754,415 Office Communication Mailed Jun. 12, 2008.
U.S. Appl. No. 10/754,415 Office Communication Mailed Jun. 4, 2009.
U.S. Appl. No. 10/829,826 Office Communication Mailed Jul. 6, 2007.
U.S. Appl. No. 10/829,826 Office Communication Mailed Apr. 4, 2008.
U.S. Appl. No. 10/829,826 Office Communication Mailed Dec. 10, 2008.
U.S. Appl. No. 10/844,938 Office Communication Mailed Feb. 2, 2007.
U.S. Appl. No. 10/844,938 Office Communication Mailed Aug. 7, 2007.
U.S. Appl. No. 10/844,938 Office Communication Mailed May 20, 2008.
U.S. Appl. No. 10/844,938 Office Communication Mailed Jan. 30, 2009.
U.S. Appl. No. 10/891,337 Office Communication Mailed Apr. 20, 2009.
U.S. Appl. No. 10/933,928 Office Communication Mailed Jun. 02, 2006.
U.S. Appl. No. 10/943,344 Office Communication Mailed Feb. 27, 2007.
U.S. Appl. No. 10/943,344 Office Communication Mailed May 21, 2008.
U.S. Appl. No. 10/943,344 Office Communication Mailed Feb. 23, 2009.
U.S. Appl. No. 11/059,776 Office Communication Mailed Jan. 19, 2007.
U.S. Appl. No. 11/059,776 Office Communication Mailed May 29, 2007.
U.S. Appl. No. 11/059,776 Office Communication Mailed Jan. 23, 2008.
U.S. Appl. No. 11/060,135 Office Communication Mailed Dec. 21, 2006.
U.S. Appl. No. 11/060,135 Office Communication Mailed Mar. 8, 2007.
U.S. Appl. No. 11/060,135 Office Communication Mailed Jul. 24, 2007.
U.S. Appl. No. 11/060,135 Office Communication Mailed Mar. 25, 2008.
U.S. Appl. No. 11/060,135 Office Communication Mailed Jan. 2, 2009.
U.S. Appl. No. 11/210,516 Office Communication Mailed Jun. 8, 2007.
U.S. Appl. No. 11/210,516 Office Communication Mailed Oct. 19, 2007.
U.S. Appl. No. 11/233,630 Office Communication Mailed Jun. 8, 2007.
U.S. Appl. No. 11/233,630 Office Communication Mailed Jul. 13, 2007.
U.S. Appl. No. 11/233,630 Office Communication Mailed Apr. 16, 2008.
U.S. Appl. No. 11/233,630 Office Communication Mailed Oct. 2, 2008.
U.S. Appl. No. 11/331,978 Office Communication Mailed Nov. 15, 2007.
U.S. Appl. No. 11/331,978 Office Communication Mailed Aug. 15, 2008.

U.S. Appl. No. 11/331,978 Office Communication Mailed Oct. 17, 2008.
U.S. Appl. No. 11/331,978 Office Communication Mailed Jun. 2, 2008 (interview summary).
U.S. Appl. No. 11/331,987 Office Communication Mailed Jul. 16, 2007.
U.S. Appl. No. 11/331,987 Office Communication Mailed Oct. 22, 2007.
U.S. Appl. No. 11/331,987 Office Communication Mailed Jul. 9, 2008.
U.S. Appl. No. 11/404,561 Office Communication Mailed May 16, 2008.
U.S. Appl. No. 11/404,561 Office Communication Mailed Feb. 4, 2009.
U.S. Appl. No. 11/409,535 Office Communication Mailed Oct. 31, 2007.
U.S. Appl. No. 11/409,535 Office Communication Mailed Apr. 16, 2008.
U.S. Appl. No. 11/491,376 Office Communication Mailed Oct. 31, 2008.
U.S. Appl. No. 11/491,376 Office Communication Mailed Apr. 22, 2009.
U.S. Appl. No. 11/582,859 Office Communication Mailed Oct. 21, 2008.
U.S. Appl. No. 11/582,863 Office Communication Mailed Aug. 20, 2007.
U.S. Appl. No. 11/582,863 Office Communication Mailed Jun. 17, 2008.
U.S. Appl. No. 11/582,863 Office Communication Mailed Feb. 26, 2009.
U.S. Appl. No. 11/582,930 Office Communication Mailed Sep. 14, 2007.
U.S. Appl. No. 11/582,930 Office Communication Mailed May 2, 2008.
U.S. Appl. No. 11/582,930 Office Communication Mailed Oct, 24, 2008.
U.S. Appl. No. 11/582,930 Office Communication Mailed Jan. 16, 2009.
U.S. Appl. No. 12/211,641 Office Communication Mailed Apr. 17, 2009.
U.S. Appl. No. 90/010,209 Office Communication Mailed Jun. 27, 2008.
U.S. Appl. No. 90/010,209 Office Communication Mailed Jul. 22, 2008.
U.S. Appl. No. 90/010,210 Office Communication Mailed Jun. 27, 2008.
U.S. Appl. No. 90/010,210 Office Communication Mailed Jul. 22, 2008.
Arbique et al., "Comparison of the Velogene Rapid MRSA Identification Assay, Denka MRSA-Screen Assay, and BBL Crystal MRSA ID System for rapid identification of methicillin-resistant Staphylococcus aureus" Diagn. Microbiol. Infect. Dis. (2001) 40(1-2):5-10.
Archer, G. L. et al., "Detection of Methicillin Resistance in Staphylococci by Using a DNA Probe," *Antimicrob. Agents Chemother.* (1990) 34(9): 1720-1724.
Armstrong, P. et al., "Sensitive and Specific Colorimetric Dot Assay to Detect Eastern Equine Encephalomyelitis Viral RNA in Mosquitoes After PCR Amplification" *J. Med, Entomol.* (1995) 32(1): 42-52.
Arnal et al., "Quantification of Hepatitis A virus in shellfish by competitive reverse transcription PCR with coextraction of standard RNA" Applied and Environmental Microbiology, American Society for Microbiology (1999) 65(1):322-326.
Aronsson et al., Persistence of the influenza A/WSN/33 virus RNA at midbrain levels of immunodefective mice, Online Publication Date: Apr. 1, 2001, Journal of the NeuroVirology 7:117- 124, 2001.
Ausubel et al., Current Protocols in Molecular Biology (Relevant portions of the book).
Avellon et al. "Rapid and sensitive diagnosis of human adenovirus infections by a generic polymerase chain reaction" *J. Virol. Methods* (2001) 92:113-120.

Azevedo et al. "Detection of influenza, parainfluenza, adenovirus and respiratory syncytial virus during asthma attacks in children older than two years old." Allergol. Immunopathol. (2003) 31:311- 317.
Baba et al., "Genome and virulence determinants of high virulence community-acquired MRSA" Lancet (2002) 359:1819-1827.
Bahrmand et al., "Polymerase chain reaction of bacterial genomes with single universal primer: application to distinguishing mycobacteria species" *Molecular and Cellular Probes* (1996) 10:117-122.
Bahrmand et al., "Use of restriction enzyme analysis of amplified DNA coding for the hsp65 gene and polymerase chain reaction with universal primer for rapid differentiation of mycobacterium species in the clinical laboratory" *Scandinavian Journal of Infectious Diseases* (1998) 30:477-480.
Bai, J, T.H. Liu and D.M.. Lubman, "Matrix-Assisted Laser Desorption/Ionization Mass Spectrometry of Restriction Enzyme-Digested Plasmid DNA Using an Active Nafion Substrate," 8 Rapid Commun. Mass Spectrom. 687-691 (1994) ('787 reexamination).
Baker et al., "Review and re-analysis of domain-specific 16S primers" *J. Microbiol. Methods* (2003) 55:541-555.
Banik et al. "Multiplex PCR assay for rapid identification of oculopathogenic adenoviruses by amplification of the fiber and hexon genes" *J. Clin. Microbiol* (2005)43:1064-1068.
Baron, E. J., "Genetic Aspects of Methicillin Resistance in Staphylococcus aureus and Methods Used for its Detection in Clinical Laboratories in the United States," *J. Chemother*. (1995) 7(Suppl. 3): 87-92.
Barr et al., "An Influenza A(H3) Reassortant Was Epidemic in Australia and New Zealand in 2003" J. Med. Virol. (2005) 76:391-397.
Barski, P. et al., "Rapid assay for detection of methicillin-resistant Staphylococcus aureus using multiplex PCR," *Mol. Cell Probes* (1996) 10:471-475.
Bastia et al., "Organelle DNA analysis of Solanum and Brassica somatic hybrids by PCR with 'universal primers'." *Theoretical and Applied Genetics* (2001) 102:1265-1272.
Batey et al., "Preparation of Isotopically Labeled Ribonucleotides for Multidimensional NMR Spectroscopy of RNA" *Nucleic Acids Research* (1992) 20:4515-4523.
Baumer et al., "Age-related Human mtDNA Deletions: a Heterogeneous Set of Deletions Arising at a Single Pair of Directly Repeated Sequences" Am. *J. Hum. Genet* . (1994) 54:618-630.
Beall, B., et al. "Survey of emm Gene Sequences and T-Antigen Types from Systemic Streptococcus pyogenes Infection Isolates Collected in San Francisco, California; Atlanta, Georgia; and Connecticut in 1994 and 1995" (1997), J. Clin. Micro. 35, 1231-1235.
Beall et al., "Sequencing emm-Specific PCR Products for Routine and Accurate Typing of Group a Streptococci" (1996) J. Clin. Micro. 34, 953-958.
Benko, M. et al., "Family Adenoviridae", Virus taxonomy, VIIIth report of the International Committee on Taxonomy of Viruses (2004) Fauquet, C.M. et al. (Eds.) Academic Press, New York, pp. 213-228.
Benson et al., "Advantages of Thermococcus kodakaraenis (KOD) DNA polymerase for PCR-mass spectrometry based analyses" *J. Am. Soc. Mass Spectrom.* (2003) 14:601-604.
Berencsi, G. et al., "Molecular Biological Characterization of Adenovirus DNA", Acta Microbiol. Immunol. Hung, 1998, vol. 45, Nos. 3-4; pp. 297-304.
Bisno, A.L. (1995) in Principles and Practice of Infectious Diseases, eds., Mandell, G.L., Bennett, J.E. & Dolin, R. (Churchill Livingston, New York), vol. 2, pp. 1786-1799.
Black et al., "Detection of trace levels of tricothecene mycotoxins in human urine by gas chromatography-mass spectrometry" *J. Chromatog* (1986) 367:103-115.
Blaiotta, G. et al., "PCR detection of staphylococcal enterotoxin genes in Staphyiococcus spp. strains isolated from meat and dairy products. Evidence for new variants of seG and sel in *S. aureus* Ab-8802," *J. Appl. Microbiol.* (2004) 97:719-730.
Blast Search results (Mar. 2006).
Boivin-Jahns et al., "Bacterial Diversity in a Deep-Subsurface Clay Environment" *Applied and Environmental Microbiology* (1996) 62:3405-3412.
Bolton and Mccarthy, Proc. Natl. Acad. Sci. U.S.A., 48, 1390 (1962).

Bont, Thomas et al., "Matrix-assisted laser desorption/ionization time-of-flight mass spectrometry-based detection of microsatellite instabilities in coding DNA sequences: a novel approach to identify DNA-mismatch repair-deficient cancer cells," Clinical Chemistry, 49(4):552-561 Apr. 2003.

Borrow et al., "SiaD PCR Elisa for confirmation and identification of serogroup Y and W135 meningococcal infections" Fems Microbiological Letters (1998) 159:209-214.

Boubaker, K. et al., "Panton-Valentine Leukocidin and Staphylococcal Skin Infections in Schoolchildren," Emerg.Infct. Dis. (2004) 10(1):121-124.

Bowen et al., "The native virulence plasmid combination affects the segregational stability of a theta-replicating shuttle vector in *bacillus anthracis var*, New Hampshire" *J. Appl. Microbiol.* (1999) 87:270-278.
Bowers, K. M. et al., "Screening for methicillin resistance in *Staphylococars aureus* and coagulase-negative staphylococci: evaluation of three selective and Mastalex-MRSA latex agglutination," *Br. J. Biomed. Sci*. (2003) 60(2):71-74.
Brakstad, O. G, et al., "Multiplex polylnerase chain reaction for detection of genes for Staphylococcus aureus themonuclease and methicillin resistance and correlation with oxacillin resistance," *APMIS* (1993) 101:681-688.
Brakstad, O. G. et al., "Direct identification of *Staphylococcus aureus* in blood cultures by detection of the gene, encoding the thermostable nuclease or the gene product," *APMIS* (1995) 103:209-218.
Brandt, C.D., et al., "Infections in 18,000 Infants and Children in a Controlled Study of Respiration Tract Disease. I. Adenovirus Pathogenicity in Relation to Serologic Type and Illness Syndrome," Am. J. Epidemio.; 1969, vol. 90, No. 6, pp. 484-500.
Brayshaw, D. P., "Methicillin-resistant *Staphylococcus aureus*: evaluation of detection techniques on laboratory-passaged organisms," *Br. J Biomed. Sci*. (1999) 56:170-176.
Brightwell et al., "Development of internal controls for PCR detection of Bacillus anthracis" Molecular and Cellular Probes (1998) 12(6):367-377.
Brightwell , G. et al., "Genetic targets for the detection and identifiaction of Venezuelan equine encephalitis viruses," Arch. Virol (1998) 143(4): 731-742.
Bronzoni, R. V. M. et al., "Multiplex nested PCR for Brazilian *Alphavirus* diagnosis," Trans. R. Soc. Trop. Med. Hyg. (2004) 98(8): 456-461.
Bronzoni, R. V. M. et al., "Duplex Reverse Transcription-PCR Followed by Nested PCR Assats for Detection and Identification of Brazilan Alphaviruses and Flaviviruses." *J. Clin. Microbiol*. (2005) 43(2): 696-702.
Brown, "Advances in Molecular Diagnostics for Avian Influenza" Dev. Biol. (2006) 124:93-97.
Brownstein et al., "Modulation of Non-Templated Nucleotide Addition by Taq DNA Polymerase: Primer Modifications that Facilitate Genotyping" BioTechniques (1996)20:1004-1010.
Brunaud et al., "T-DNA integration into the Arabidopsis genome depends on sequences of pre-insertion sites" EMBO Rep. (2002) 3(12):1152-1157.
Buck et al., "Design Strategies and Performance of Custom DNA Sequencing Primers" Biotechniques (1999) 27:528-536.
Butler "DNA profiling and quantitation of human DNA" CCQM BAWG 04122005.
Campbell et al., "Detection of California serogroup Bunyaviruses in tissue culture and mosquito pools by PCR" *J. Virol. Methods* (1996) 57:175-179.
Carracedo et al., "DNA commission of the international society for forensic genetics: guidelines for mitochondria DNA typing" *Forensic Science International* (2000) 110:79-85.
Carroll, K. C. et al., "Rapid Detection of the Staphylococcal mecA Gene from Bactec Blood Culture Bottles by the Polymerase Chain Reaction,"*Am. J. Clin. Pathol*. (1996) 106:600-5.
Case et al., "Maternal inheritance of mitochondria DNA polymorphisms in cultured human fibroblasts," Somatic Cell Genetics (1981) 7:103-108.
Cattoli et al., "Comparison of three rapid detection systems for type a influenza virus on tracheal swabs of experimentally and naturally infected birds" Avian Pathology (2004) 33(4):432-437.
Cavassini, M. et al., "Evaluation of MRSA-Screen, a Simple Anti-Pbp 2a Slide Latex Agglutination Kit, for Rapid Detection of Methicillin Resistance in *Staphylococcus aureus*," *J. Clin. Microbial*. (1999) 37(5): 1591-1594.
Cespedes et al., "Polymerase chain reaction restriction fragment length polymorphism analysis of a short fragment of the cytochrome b gene for identification of flatfish species" *J. Food Protection* C1465 (1998) 61:1684-1685.
Chamberlin et al., "New RNA polymerase from Escerichia coli infected with baeriophage T7" Nature 228:227 (1970).
Chandra, S. et al., "Virus reduction in the preparation and intravenous globulin: In vitro experiments," *Transfusion* (1999) 39(3): 249-257.
Chang, P.-K. et al., "aflT, a MFS transporter-encoding gene located in the aflatoxin gene cluster, does not have a significant role in aflatoxin secretion," Fungal Genet.Biol. (2004) 41:911-920.
Chaves, F. et al., "Molecular Characterization of Resistance to Mupirocin in Methidlin-Susceptible and -Resistant Isolates of *Staphylococcus aureus* from Nasal Samples," *J. Clin. Microbiol*. (2004) 42(2):822-824.
Chelly et al., "Transcription of the dystrophin gene in human muscle and non-muscle tissue" Nature (1988) 333(6176):858-860.
Chen et al., "Universal primers for amplification of mitochondria small subunit ribosomal RNA- encoding gene in scleractinian corals" *Marine Biotechnology* (2000) 2:146-153.
Chen et al., "A universal PCR primer to detect members of the Potyviridae and its use to examine the taxonomic status of several members of the family" *Archives of Virology* (2001) 146:757-766.
Chen, N. et al., "The genomic sequence of ectromelia virus, the causative agent of mousepox," *Virology* (2003) 317:165-186.
Chen et al., "Genetic mapping of the cold-adapted phenotype of B/Ann Arbor/1/66, the master donor virus for live attenuated influenza vaccines (FluMist)" Virology (2006) 345:416-423.
Chen, CH, K. Tang, N. Taranenko and S. Allman, "Laser Desorption Mass Spectrometry for Fast DNA Sequencing," ve (Nov. 1994), http://www.ornl.gove/sci/techresources/Human_Genome/publicat/94SANTA/sequencing/seqtoc.shtml ('787 reexamination).
Chmielewicz, B. et al., "Development of a PCR-Based Assay for Detection, Quantification, and Genotyping of Human Adenoviruses," Clin. Chem., 2005, vol. 51, No. 8, pp. 1365-1373.
Cho et al., "Application of the ribonuclease P (RNase P) RNA gene sequence for phylogenetic analysis of the gene Saccharomonospora" *International Journal of Systematic Bacteriology* (1998) 48:1223-1230.
Choi et al., "Detection and subtying of swine influenza H1N1, H1N2 and H3N2 viruses inclinical samples using two multiplex RT-PCR assays" J. Virol. Methods (2002) 102:53-59.
Choi, S. et al., "Real-Time PCR Quantification of Human Adenoviruses in Urban Rivers Indicates Genome Prevalence but Low Infectivity," Appl. Environ. Microbiol., 2005, vol. 71, No. 11, pp. 7426-7433.
Christel, LA et al., "Rapid, Automated Nucleic Acid Probe Assays Using Silicon Microstructures for Nucleic Acid Concentration" J. Biomech. Eng., 1999, 121, 22-27.
Claas, E.C.J. et al., "Internally Controlled Real-Time PCT Monitoring of Adenovirus DNA Load in C1497 Serum or Plasma of Transplant Recipients," J. Clin. Microbiol., 2005, vol. 43, No. 4, pp. 1738-1744.
Cloney, L. et al., "Rapid detection of mecA in methicillin resistant *Stuphylococcus* aureus using cycling probe technology," *Mol. Cell Probes* (1999) 13:191-197.
Conrads et al., "16S-23S rDNA internal transcribed spacer sequences for analysis of the phylogenetic relationships among species of the genus Fusobacterium" *International Journal of Systematic and Evolutionary Microbiology* (2002) 52:493-499.
Cornel et al., "Polymerase chain reaction species diagnostic assay for Anopheles quadrimaculatus cryptic species (Diptera: Culicidae) based on ribosomal DNA ITS2 sequences" *Journal of Medical* Entomology (1996) 33:109-116.
Couto, I. et al., "Development of Methicillin Resistance in Clinical Isolates of *Staphylococcus sciuri* by Transcriptional Activation of the mecA Homologue Native to the Species," *J. Bacteriol*. (2003) 185(2):645-653.

Crain et al., "Applications of mass spectrometry of the characterization of oligonucleotides and nucleic acids" Curr. Opin. Biotechnol. (1998) 9:25-34.

Crawford-Miksza, L.K. et al., "Analysis of 15 Adenovirus Hexon Proteins Reveals the Location and Structure of Seven Hypervariable Regions Containing Serotype-Specific Residues," J. Virol., 1996, vol. 70, No. 3, pp. 1836-1844.

Crawford-Miksza, L.K. et al., "Adenovirus Serotype Evolution is Driven by Illegitimate Recombination in the Hypervariable Regions of the Hexon Protein," Virol., 1996, Vol. 224, pp. 357-367.

Crawfor-Miksza et al., "Strain variation in adenovirus serotypes 4 and 7a causing acute respiratory disease." (1999) 37:1107-1112.

Crespillo et al., "Mitochondrial DNA sequences for 118 individuals from northeastern Spain" Int. J. Legal Med. (2000) 114:130-132.

Cui, L. et al., "Contribution of a Thickened Cell Wall and Its Glutamine Nonamidated Component to the Vancomnycin Resistance Expressed by *Staphylococcus aureus* Mu50," *Antimicrob. Agents Chemother.* (2000) 44(9):2276-2285.

Dasen et al., "Classification and identification of Propionibacteria based on 16S ribosomal RNA genes and PCR" *Systematic and Applied Microbiology* (1998) 21:251-259.

De Sousa, M. A. et al., "Bridges from hospitals to the laboratory: genetic portraits of methicillin-resistant *Staphylococcus aureus* clones," *FEMS lmmunol. Med. Microbiol.* (2004) 40:101-111.

Deforce et al., "Analysis of oligonucleotides by ESI-MS" *Advances in Chromatography* (2000) 40:539-566.

Deforce et al., "Characterization of DNA Oligonucleotides by Coupling of Capillary Zone Electrophoresis to Electrospray Ionization Q-TOF Mass Spectrometry" *Analytical Chemistry* (1998) 70:3060-3068.

De Jong, J.C. et al., "Adenoviruses from Human Immunodeficiency Virus-Infected Individuals, Including Two Strains That Represent New Candidate Serotypes Ad50 and Ad51 of Species B1 and D, Respectively," J. Clin. Microbiol., 1999, vol. 37, No. 12, pp. 3940-3945.

Del Vecchio, V. G. et al., "Molecular Genotyping of Methicillin-Resistant *Staphylococcus aureus* via Fluorophore-Enhanced Repetitive-Sequence PCR," *J. Clin. Microbiol.* (1995) 33(8):2141-2144.

Demesure et al., "A set of universal primers for amplification of polymorphic non-coding regions of mitochondrial and chloroplast DNA in plants" *Molecular Ecology* (1995) 4:129-131.

Denis et al., "Development of a semiquantitative PCR assay using internal standard and colorimetric detection on microwell plate for pseudorabies virus" Mol. Cell. Probes (1997) 11(6):439-448.

Deurenberg et al., "Rapid detection of Panton-Valentine leukocidin from clinical isolates of Staphylococcus aureus strains by real-time PCR" FEMS Microbiol. Lett. (2004) 240(2):225-228.

Dias Neto et al., "Shotgun sequencing of the human transcriptome with ORF expressed sequence tags" *PNAS* (2000) 97:3491-3496.

Di Guilmi, A.M. et al., "Human adenovirus serotype 3 (Ad3) and the Ad3 fiber p[protein bind to a 130- kDa membrane protein on HeLa cells," Virus Res., 1995, vol. 38, pp. 71-81.

Diep, B. A. et al., "Complete genome sequence of USA300, an epidemic clone of community acquired meticillin-resistant *Staphylococcus aureus*," Lancet (2006) 367:731-739.

Dinauer et al., "Sequence-based typing of HLA class II DQB1" *Tissue Anigens* (2000) 55:364-368.

Ding et al., "A high-throughput gene expression analysis technique using competitive PCR and matrix-assisted laser desorption ionization time-of-flight MS" PNAS (2003) 100(6):3059-3064.

Donehower, et al., "The use of primers from highly conserved pol regions to identify uncharacterized retroviruses by the polymerase chain reaction," J. Vir. Methods (1990) 28:33-46.

Donofrio et al., "Detection of influenza A and B in respiratory secretions with the polymerase chain reaction" PCR methods and applications, Cold Spring Harbor Lab. Press vol. 1, No. 4, (1992) pp. 263-268.

Doty et al., Proc. Natl. Acad. Sci. USA 46:461 (1960).

Drosten et al., New England Journal of Medicine, 2003, 348, 1967.

Dubernet et al., "A PCR-based method for identification of Lactobacilli at the genus level" *FEMS Microbiology Letters* (2002) 214:271-275.

EBI Accession No. AEM14131 (Jan. 11, 2007) - Bacterial DNA PCR PRIMER SEQ ID No:874.

Ebner, K. et al., "Molecular Detection and Quantitative Analysis of the Entire Spectrum of Human Adenoviruses by a Two-Reaction Real-Time PCR Assay," J. Clin. Microbiol., 2005, vol. 43, No. 7, pp. 3049-3053.

Ebner et al., "Typing of human adenoviruses in specimens of immunosuppressed patients by PCR- fragment length analysis and real-time quantitative PCR" Journal of Clinical Microbiology (2006) 44:2808-2815.

Echavarria, M. et al., "PCR Method for Detection of Adenovirus in Urine of Healthy and Human Immunodeficiency Virus-Infected Individuals," J. Clin. Microbiol., 1998, vol. 36, No. 11, pp. 3323-3326.

Echavarria, M. et al., "Detection of Adenoviruses (AdV) in Culture-Negative Environmental Samples by PCR During an AdV-Associated Respiratory Disease Outbreak," J. Clin. Microbiol., 2000, vol. 38, No. 8, pp. 2982-2984.

Echavarria, M. et al., "Prediction of severe disseminated adenovirus infection by serum PCR," Lancet, 2001, Vol. 358, pp. 384-385.

Echavarria, M. et al., "Rapid Detection of Adenovirus in Throat Swab Specimens by PCR During Respiratory Disease Outbreaks among Military Recruits", J. Clin. Microbiol., 2003, vol. 41, No. 2, pp. 810-812.

Echavarria, M. et al., "Use of PCR to demonstrate of Adenovirus Species B, C, of F as Well as Coinfection with Two Adenovirus Species in Children with Flu-Like Symptoms", J. Clin. Microbiol, 2006, vol. 44, No. 2, pp. 625-627.

Ecker et al., "Rapid identification and strain-typing of respiratory pathogens for epidemic surveillance" PNAS (2005) 102(22):8012-8017.

Ecker et al., "The Ibis T5000 Universal Biosensor: An Automated Platform for Pathogen C1575 Identification and Strain Typing" JALA (2006) 11:341-351.

Edwards, K.M. et al., "Adenovirus Infections in Young Children", Pediatrics, 1985, vol. 76, No. 3, pp. 420-424.

Ellis et al., "Molecular diagnosis of influenza" Rev. Med. Virol. (2002) 12(6):375-389.

Elnifro et al., "PCR and Restriction Endonuclease Analysis for Rapid Identification of Adenovirus Subgenera" Journal of Clinical Microbiology (2000) 38:2055-2061.

Elsayed, S. et al., "Development and Validation of a Molecular Beacon Probe-Based Real-Time Polymerase Chain Reaction Assay for Rapid Detection of Methicillin Resistance in *Staphylococcus aureus*," Arch. Pathol. Lab. Med. (2003) 127945-849.

EMBL Accession No. S90302, Human, Muscle, Mitochondrial Mutant, 22 nt, segment 2 of 2 C1585 (XP002436791) Nov. 26, 1993.

EMBL Accession AJ552897 (Mar. 29, 2003).

EMBL Accession AR321656 (Aug. 12, 2003).

EMBL Accession L15697 (Mar. 4, 2000).

EMBL Accession AB068711 (May 21, 2003).

EMBL Accession Z48571 (Jun. 9 1995).

Enright, M. C, et al., "Multilocus Sequence Typing for Characterization of Methicillin-Resistant and Methicillin-Susceptible Clones of *Staphylococcus aureus*," *J. Clin. Microbial.* (2000) 38(3): 1008-1015.

Enright, M. C. et al., "The evolutionary history of methicillin-resistant *Staphylococcus aureus* (MRSA)," PNAS(2002) 99(11): 7687-7692.

Enright, M. C. et al., "The evolution of a resistant pathogen—the case of MRSA," *Curr. Opin. Pharmacol.* (2003) 3:474-479.

Enright, M.C., et al., "Multilocus Sequence Typing of Streptococcus pyogenes and the C1603 Relationships between emm Type and Clone" Infection and Immunity, 2001, 69, 2416-2427.

Eremeeva et al., "Evaluation of a PCR Assay for Quantitation of Rickettsia rickettsii and Closely C1605 Related Spotted Fever Group Rickettsiae" J. Clin. Microbiol. (2003) 41(12):5466-5472.

Erlich (ed.). PCR Technology, Stockton Press (1989).

Esmans et al., "Liquid Chromatography-Mass Spectrometry in Nucleoside, nucleotide and modified nucleotide characterization" *J. Of Chromatography A* (1998) 794:109-127.

Evans & Wareham, "Practical Algorithms for Universal DNA Primer Design: An Exercise in Algorithm Engineering".

European Patent Office Communication 96(2) EPC for 02709785.6 dated Nov. 20, 2006.
European Patent Office Communication for 06849755.1 dated Mar. 12, 2008.
European Search Report for 02709785.6 dated Oct. 10, 2005.
European Supplemental Search Report for 03796752.8 dated Aug. 14, 2007.
European Supplemental Search Report for 03810055.8 dated Jul. 9, 2007.
European Supplemental Search Report for 02709785.Jun. 2405 (PCT/US0206763) dated Oct. 12, 2005.
European Supplemental Search Report for 04752257.8 dated Feb. 15, 2006.
European Supplemental Search Report for 05751872.2 dated Jan. 28, 2008.
European Supplemental Search Report for 05856582.1 dated Nov. 10, 2008.
European Supplemental Search Report for 04775904.8 dated Jul. 25, 2008.
European Supplemental Search Report for 05856582.1 dated Nov. 10, 2008.
Facklam, R., et al., "emm Typing and Validation of Provisional M Types for Group a Streptococci" (1999) Emerging Infectious Diseases, 5, 247-253.
Fang, H. et al., "Rapid Screening and Identification of Methicillin-Resistant Staphylococcus aureus from Clinical Samples by Selective-Broth and Real-Time PCR Assay," J. Clin. Microbial. (2003) 41(7):2894-2899.
Farrell, D. J., "'The Reliability of Microscan Conventional and Rapid Panels to Identify Staphylococcus aureus and Detect Methicillin Resistance: an Evaluation Using the Tube Coagulase Test and mecA PCR," Pathology ( 1 997) 29:406-410.
Fedele C G et al., "Multiplex polymerase chain reaction for the simultaneous detection and typing of polyomavirus JC, BK, and SV40 DNA in clinical samples", Journal of Virological Methods, 82(2), Oct. 1999, pp. 137-144.
Fedele C G Et Al., "Quantitation of polyomavirus DNA by a competitive nested polymerase chain reaction," Journal of Virological Methods, 88(1):51-61 (Jul. 2000).
Feng, P., "Impact of molecular biology on the detection of food pathogens" Mol. Biotechnol., 1997, 7, 267-278.
Figueiredo et al., "Identification of Brazilian flaviviruses by a simplified reverse transcription-polymerase chain reaction method using Flavivirus universal primers" American Journal of Tropical Medicine and Hygiene (1998) 59:357-362.
Flora, et al., "Dual-micro-Esi source for precise mass determination on a quadrupole time-of-flight mass spectrometer for genomic and proteomic applications" Anal. Bioanal. Chem. (2002) 373:538-546.
Fong, W. K., et al., "Rapid Solid-Phase Immunoassay for Detection of Methicillin-Resistant Staphylococcus aureus Using Cycling Probe Technology." J. Clin. Microbiol. (2000) 38(7): 2525- 2529.
Fox et al., "Identification and Detection of Bacteria: Electrospray MS-MS Versus Derivatization/GCMS" Proceedings of the ERDEC Scientific Conference on Chemical and Biological Defense Research (1994) 39-44.
Fox et al., "Identification of Brucella by Ribosomal-spacer-region PCR and differentiation of, Brucella canis from other Brucella spp. pathogenic for humans by carbohdrate profiles" Journal of Clinical Microbiology (1998) 36:3217-3222.
Fox et al., "Report of the 'Bioterrorism Workshop' Duke University Thomas Center on Apr. 24, 2002 organized by US Army Research Office" Journal of Microbiological Methods (2002) 51:247-254.
Fox, J.P. et al., "The Virus Watch Program: A Continuing Surveillance of Viral Infections in Metropolitan New York Families", Am. J. Epidemiol., 1969, vol. 89, No. 1, pp. 25-50.
Francois, P. et al., "Rapid Detection of Methicillin-Resistant Staphylococcus aureus Directly from Sterile or Nonsterile Clinical Samples by a New Molecular Assay," J. Clin. Microbiol. (2003) 41(1):254-260.
Fraser et al., "The Minimal Gene Complement of Mycoplasma Genitalium" Science (1995) 270:397-403.

Freiberg et al. Genome-wide mRNA profiling: impact on compound evaluation and target identification in anti-bacterial research. Targets 1(1):20-29 (2002).
Freymuth et al., "Comparison of Multiplex PCR Assays and Conventional Techniques for the Diagnostic of Respiratory Virus Infections in Children Admitted to Hospital with an Acute Respiratory Illness" J. Med. Virol. (2006) 78(11):1498-1504.
Freymuth, F. et al., "Detection of respiratory syncytial virus, parainfluenzavirus 3, adenovirus and rhinovirus sequences in respiratory tract of infants by polymerase chain reaction and hybridization", Clin. Dian. Virol, 1997, vol. 8, pp. 31-40.
Fuerstenau et al., "Molecular Weight Determination of Megadalton DNA Electrospray Ions Using Charge Detection Time-of-flight Mass Spectrometry" Rapid Comm. Mass Spec. (1995) 9:1528-1538.
Fujimoto, T. et al., "Single-Tube Multiplex PCR for Rapid and Sensitive Diagnosis of Subgenus B and Other Subgenera Adenoviruses in Clinical Samples", Microbiol. Immunol., 2000, vol. 44, No. 10, pp. 821-826 (abstract only).
Fujimura, S, et al., "Characterization of the mupA Gene in Strains of Methicillin-Resistant Staphylococcus aureus with a Low Level of Resistance to Mupirocin," Antimicrob. Agents Chemother. (2001) 45(2):641-642.
Fujimura, S. et al., "Isoleucyl-tRNA Synthetase Mutations in Staphylococcus aureus Clinical Isolates and in Vitro Selection of Low-Level Mupirocin-Resistant Strains," Antimicrob. Agents Chemother . (2003) 47(10): 3373-3374.
Fujioka et al., "Analysis of enterovirus genotypes using single-strand conformation polymorphisms of polymerase chain reaction products" J. Virol. Meth . (1995) 51:253-258.
Gabriel et al., "Improved mtDNA sequence analysis of forensic remains using a "mini-primer set" amplification strategy" Journal of Forensic Sciences (2001)46:247-253.
Gall, J.G.D. et al., "Construction and Characterization of Hexon-Chimeric Adenoviruses: Specification of Adenovirus Serotype", J. Virol, 1998, vol. 72, No. 12, pp. 10260-10264.
Gammelin et al., "Two Subtypes of Nucleoproteins (NP) of Influenza a Viruses" Virology (1989) 170:71-80.
Garcia et al., "Quantitative Real-Time PCR Detection of Rift Valley Fever Virus and Its Application to Evaluation of Antiviral Compounds" J. Clin. Microbiol. (2001) 39(12):4456-61.
Gattermann et al., "Heteroplasmic Point Mutations of Mitochondria! DNA Affecting Subunit I of Cytochrome c Oxidase in Two Patients with Acquired Idiopathic Sideroblastic Anemia"Blood (1997) 90:4961-4972.
Gaydos, C.A. et al., "Adenovirus Vaccines in the U.S. Military", Military Med., 1995, vol. 160, No. 6, pp. 300-304.
Geha et al., "" J. Clin. Microbiol. (1994) 32:1768-1772.
GenBank Accession No. NC_ 000913.
Genbank Accession AF304460 (Jul. 11, 2001).
Genbank Accession No. M21150 Apr. 29, 1993.
Genbank Accession No. AF375051.1 (Jun. 26, 2001).
Genbank Accession No. Z48571 (Jun. 9, 1995).
Genbank Accession No. X84646 (Jul. 2, 1995).
Genbank GI:15922990 [online] Oct. 4, 2001 [retrieved on Jun. 22, 2008] retrieved from: http://www.ncbi.nlm.nih.gov/entrez/viewer.fcgi?15922990:0LD08:50885 (pp. 1, 12, 15, 148, 216, 476, 722, 723, 725, 881, 1251).
Genbank GI:18542231 [online] Sep. 16, 2003 [retrieved on Jun. 23, 20081 retrieved from http://www.ncbi.nlm.nih.gov/entrez/viewer.fcgi?db=nuccore&id=18542231 (2 pages).
Genbank GI:21281729 [online], publicly available at least as of May 31, 2002 [retrieved on Apr. 11, 20081, retrieved from: http://www.ncbi.nlm.nih.gov/entrez/viewer.fcgi?21281729:OLD11:599579 (pp. 1, 723 and 1137).
Gendel et al., "Computational analysis of the specificity of 16S rRNA-derived signature sequences for identifying food-related microbes" Food Microbiology (1996) 13:1-15.
Gibb et al., "Development and evaluation of a 5' fluorogenic nuclease assay to detect and differentiate between Ebola Virus subtypes Zaire and Sudan", Journal of Clinical Microbiology, 39(11):4125-4130 (Nov. 2001).
Ginther et al., "Identifying individuals by sequencing mitochondrial DNA from teeth," Nature Genetics (1992) 2:135-138.

Gilbert et al., "Comparison of commercial assays for the quantitation of HBV DNA load in health care workers: calibration differences" J. Virol. Methods (2002) 100(1-2):37-47.

Giles et al., "Maternal inheritance of human mitochondrial DNA," PNAS (1980) 77:6715-6719.

Gill, S. R. et al., "Insights on Evolution of Virulence and Resistance from the Complete Genome Analysis of an Early Methicillin-Resistant Staphylococcus aureus Strain and a Biofilm-Producing Methicillin-Resistant Staphylococcus epidemidis Strain," J. Bacteriol. (2005) 187(7): 2426-2438.

Gilliland et al., "Analysis of cytokine mRNA and DNA: detectionf and quantitation by competitive polymerase chain reaction" PNAS (1990) 87(7):2725-2729.

Gjoen et al., "Specific detection of coxsackie viruses a by the polymerase chain reaction" Clinical and Diagnostic Virology (1997) 8:183-188.

Golden et al., Pilot Study of COBAS PCR and Ligase Chain Reaction for Detection of Rectal Infections Due to Chlamydia trachomatis, J. Clin. Microbiol., 41(5):2174-2175 (May 2003).

Goto et al., "Applications of the partial 16S rDNA sequence as an index for rapid identification of species in the genus Bacillus" J. Gen. Appl. Microbiol. (2000) 46:1-8.

Gravet et al., "Characterization of a novel structural member, LukE-LukD, of the bi-component staphylococcal leucotoxins family" FEBS Lett. (1998) 436(2):202-208.

Gray, G.C. et al., "Adult Adenovirus Infections: Loss of Orphaned Vaccines Precipitates Military Respiratory Disease Epidemics", Clin. Infect. Diseases, 2000, vol. 31, pp. 663-670.

Greenberg et al., "Intraspecific nucleotide sequence variability surrounding the origin of replication in human mitochondria! DNA," Gene (1983) 21:33-49.

Griffey et al., "Detection of base pair mismatches in duplex DNA and RNA oligonucleotides using electrospray mass spectrometry" Proceedings of SPIE - The International Society for Optical Engineering (1997) 2985:82-86.

Griffin et al., "Direct genetic analysis by matrix-assisted laser desorption/ionization mass spectrometry" PNAS (1999) 96:6301-6306.

Griffin et al., "Single-nucleotide polymorphism analysis by MALDI-TOF mass spectrometry" Trends in Biotechnology (2000) 18:77-84.

Grondahl, B. et al., "Rapid Identification of Nine Microorganisms Causing Acute Respiratory Tract Infections by Single-Tube Multiplex Reverse Transcription-PCR: Feasibility Study", J. Clin. Microbiol., 1999, vol. 37, No. 1, pp. 1-7.

Grundmann, H. et al., "Emergence and resurgence of meticillin-resistant Staphylococcus aureus as a public-health threat," Lancet (2006) 368: 874-885.

Grzybowski "Extremely high levels of human mitochondria! DNA heteroplasmy in single hair roots" Electrophoresis (2000) 21:548-553.

Gu, Z et al., "Multiplexed, Real-Time PCR for Quantitative Detection of Human Adenovirus", J. Clin. Microbiol., 2003, vol. 41, No. 10, pp. 4636-4641.

Guatelli et al., "Nucleic Acid Amplification in Vitro: Detection of Sequences with Low Copy Numbers and Application to Diagnosis of Human Immunodeficiency Virus Type 1 Infection" Clin. Microbiol. Rev. (1989) 2(2):217-226.

Haff et al., "Multiplex Genotyping of PCR Products with Mass Tag-Labeled Primers" Nucleic Acids Research (1997) 25(18):3749-3750.

Hahner et al., "Analysis of short tandem repeat polymorphisms by electrospray ion trap mass spectrometry" Nucleic Acids Research (2000) 2E82.1:E82.8.

Heim, A. et al., "Rapid and Quantitative Detection of Human Adenovirus DNA by Real-Time PCR", J. Med. Virol., 2003, vol. 70, pp. 228-239.

Haines,.D J., et al., "Medical response to bioterrorism: Are we prepared?" J. Okla. State Med. Assoc. C1771 2000, 93, 187-196.

Hall et al., "Base composition analysis of human mitochondrial DNA using electrospray ionization mass spectrometry: A novel tool for the identification and differentiation of humans" Analytical Biochemistry (2005) 344:53-69.

Hamdad, F. et al., "Detection of Methicillin-Oxacillin Resistance and Typing in Aminoglycoside-Susceptible Methicillin-Resistant and Kanamycin-Tobramycin-Resistant Methicillin-Susceptible" Microbial Drug Resistance (2006) 12(3): 177-185.

Hamels et al., "Consensus PCR and Microarray for Diagnosis of the Genus Staphylococcus, Species, and Methicillin Resistance" BioTechniques (2001) 31(6):1364-1366.

Hammerle et al., "A sensitive PCR assay system for the quantitation of viral genome equivalents: Hepatitis C virus (HCV)" Arch. Virol. (1996) 141:2103-2114.

Hannis et al., "Accurate characterization of the tyrosine hydroxylase forensic allele 9.3 through development of electrospray ionization Fourier transform ion cyclotron resonance mass spectrometry" Rapid Communications in Mass Spectrometry (1999) 13:954-962.

Hannis et al., "Detection of double-stranded PCR amplicons at the attomole level electrosprayed from low nanomolar solutions using FT-ICR mass spectrometry" Fresenius Journal of Analytical is Chemistry (2001) 369: 246-251.

Hannis et al., "Genotyping short tandem repeats using flow injection and electrospray ionization Fourier transform ion cyclotron resonance mass spectrometry" Rapid Communications in Mass Spectrometry (2001) 15:348-350.

Hannis et al., "Genotyping complex short tandem repeats using electrospray ionization Fourier transform ion cyclotron resonance multistage mass spectrometry" Proceedings of Spie - The International Society for Optical Engineering (2000) 3926:36-47.

Hanssen, a.M. et al., "SCCmec in staphylococci: genes on the move," FEMS lmmuol. Med. Microbiol . (2006) 46:8-20.

Hasebe, F. et al. "Combined Detection and Genotyping of Chikungunya Virus by a Specific ReverseTranscription-Polymerase Chain Reaction," J. Med. Virol. (2002) 67(3): 370-374.

Hassan et al., "Inter- and Intraspecies Variations of the 16S-23S rDNA Intergenic Spacer Region of C1793 Various Streptococcal Species" Systematic and Applied Microbiology (2003) 26(1):97-103.

Haugland et al., "Identification of putative sequence specific PCR primers for detection of the toxigenic fungal species Stachybotrys chartarum"Mol Cell Probes (1998) 12:387-396.

Hayashi et al., "Phylogenetic analysis of the human gut microbiota using 16S rDNA clone libraries and strictly anaerobic culture-based methods" Microbiology and Immunology (2002) 46:535-548.

Henchal et al., "Sensitivity and specificity of a universal primer set for the rapid diagnosis of dengue virus infections by polymerase chain reaction and nucleic acid hybridization"American Journal of C1799 Tropical Medicine and Hygiene (1991) 45:418-428.

Herrmann et al., "Differentiation of Chlamydia spp. By Sequence Determination and RestrictionEndonuclease Cleavage of RNase P RNA Genes" J. Clin. Microbiol. (1996) 34:1897-1902.

Higgins et al., "Competitive oligonucleotide single-base extension combined with mass spectrometric detection for mutation screening" BioTechniques (1997) 23:710-714.

Higgins, J.A., et al., Ann. NY Acad. Sci. , 1999, 894, 130-148.

Hill, F., et al., "Polymerase recognition of synthetic oligodeoxyribonucleotides incorporating degenerate pyrimidine and purine bases," Proc. Natl. Acad. Sci. USA 95:4258-4263 (1998).

Hiramatsu, K. et al., "The emergence and evolution of methicillin-resistant Staphylococcus aureus," Trends Microbiol. (2001) 9(10):486-493.

Hodgson et al. Molecular Characterization of the Gene Encoding High-Level Mupirocin Resistance in Staphylococcus aureus J2870. Antimicrobial Agents and Chemotherapy 38(5):1205-1208, May 1994.

Hoffmann et al., "Rescue of influenza B virus from eight plasmids" PNAS (2002) 99:11411-11416.

Hoffmann et al., "Universal primer set for the full-length amplification of all influenza a viruses" Archives of Virology (2001) 146:2275-2289.

Hofstadler et al., "Tiger: the universal biosensor" Inter. J. Mass Spectrom. (2005) 242:23-41.

Holden, M. T. G. et al., "Complete genomes of two clinical Staphylocuccus aureus strain: Evidence for the rapid evolution of virulence and drug resistance," PNAS (2004) 101(26):9786-9791.

Holland et al., "Mitochondrial DNA Sequence Analysis of Human Skeletal Remains: Identification of Remains from the Vietnam War," Journal of Forensic Sciences (1993) 38:542-553.

Holland, M.M. and T.J. Parsons "Mitochondrial DNA analsysis Validation and use for forensic casework" (1999) Forensic Science Review, vol. 11, pp. 25-51.

Holm et al., "Removing near-neighbour redundancy from large protein sequence collections" *Bioinformatics* (1998) 14:423-429.

Holmes et al., "Whole-Genome Analysis of Human Influenza a Virus Reveals Multiple Persistent Lineages and Reassortment among Recent H3N2 Viruses" PLoS Biol. (2005) 3(9):1579-1589.

Honda et al., "Universal method of hypersensitive nested PCR toward forensic DNA typing" *International Congress Series* (1998) 7:28-30.

Hongoh et al., "Evaluation of primers and PCR conditions for the analysis of 16s rRNA genes from a natural environment" FEMS Microbiol. Lett. (2003) 221:299-304.

Hood, E., "Chemical and biological weapons: New questions, new answers" Environ. Health Perspect., 1999, 107:931-932.

Houng, H.-S. H. et al., "Rapid type-specific diagnosis of adenovirus type 4 infection using a hexon-based quantitative fluorogenic PCR", Diagn. Microbiol. Infect. Dis., 2002, vol. 42, pp. 227-236.

Howell et al., "Persistent Heteroplasmy of a Mutation in the Human mtDNA Control Region: Hypermutation as an Apparent Consequence of Simple-Repeat Expansion/Contraction" *Am. J. Hum. Genet*. (2000) 66:1589-1598.

Hunag, C. et al., "Detection of arboviral RNA directly from mosquito homogenates by reverse transcription-polymerase chain reaction," *J. Virol. Methods* (2001) 94(1-2): 121-128.

Huber et al., On-line cation exchange for suppression of adduct formation in negative-ion electrospray mass spectrometry of nucleic acids." Anal. Chem. (1998) 70:5288-5295.

Huletsky, A. et al., New real-time PCR assay for rapid detection of methicillin-resistant Staphylococcus aureus directly from specimens containing a mixture of staphylococci. J. Clin. Microbial. (2004) 42(5): 1875-84.

Hung, "Detection of Sars coronavirus RNA in the cerebrospinal fluid of a patient with severe acute respiratory syndrome" Clin. Chem. (2003) 2108.

Hurdle, J. G. et al., "Analysis of Mupirocin Resistance and Fitness in Staphylococcus aureus by Molecular Genetic and Structural Modeling Techniques," *Antimicrob. Agents Chemother*. (2004) 48(11):4366-4376.

Hurst et al., "Detection of bacterial DNA polymerase chain reaction products by matrix-assisted laser desorption/ioniation mass spectrometry" *Rapid Commun. Mass. Spec*. (1996) 10:377-382.

Hurst et al., "MALDI-TOF Analysis of Polymerase Chain Reaction Products from Methanotrophic Bacteria" *Anal. Chem*. (1998) 70:2693-2698.

Hutchison et al., "Maternal inheritance of mammalian mitochondrial DNA," *Nature* (1974) 251:536-538.

Ieven, M. et al., "Rapid Detection of Methicillin Resistance in Coagulase-Negative Staphylococci by Commercially Available Fluorescence Test," *J. Clin. Microbiol*. (1995) 33(8):2183-2185.

Ihle et al., "Efficient purification of DNA fragments using a protein binding membrane" *Nucleic Acids Research* (2000) 28:e76.

Inglis, T. J. et al., "Rapid Genotypic Confirmation of Methicillin Resistance," *Pathology* (1996) 28(3):259-261.

Ingman et al., "Mitochondrial genome variation and the origin of modern humans" *Nature* (2000) 408:708-713.

Australian Search Report for AU 2003297687 dated Sep. 4, 2008.
Australian Search Report for AU 2003302236 dated Sep. 10, 2008.
Australian Search Report for AU 2004248107 dated Jul. 30, 2008.
Canadian patent office communication for Application No. 2,525,498 dated Apr. 7, 2009.
International Prelim. Exam. Report for PCT/US02/20336 dated May 12, 2004.
International Prelim. Exam. Report for PCT/US2005/033707 dated Mar. 20, 2007.
International Search Report for PCT/US02/20336 dated Feb. 3, 2003.
International Search Report for PCT/US02/20336 dated May 12, 2004.
International Search Report for PCT/US02/06763 dated Oct. 23, 2002.
International Search Report for PCT/US03/009802 dated Aug. 20, 2004.
International Search Report for PCT/US03/22835 dated Dec. 12, 2003.
International Search Report for PCT/US03/38757 dated Jun. 24, 2004.
International Search Report for PCT/US03/38795 dated Apr. 19, 2004.
International Search Report for PCT/US03/38830 dated Aug. 25, 2004.
International Search Report for PCT/US03/38505 dated Apr. 12, 2005.
International Search Report for PCT/US03/38761 dated Dec. 30, 2005.
International Search Report for PCT/US04/007236 dated Feb. 24, 2006.
International Search Report for PCT/US2004/011877 dated Apr. 20, 2006.
International Search Report for PCT/US04/012671 dated Sep. 28, 2007.
International Search Report for PCT/US04/015123 dated Oct. 3, 2005.
International Search Report for PCT/US04/015196 dated Jul. 1, 2005.
International Search Report for PCT/US2004/028869 dated Jul. 17, 2006.
International Search Report for PCT/US04/033742 dated May 15, 2006.
International Search Report for PCT/US2005/000386 dated May 9, 2006.
International Search Report for PCT/US05/005356 dated Aug. 7, 2007.
International Search Report for PCT/US05/007022 dated Oct. 20, 2006.
International Search Report for PCT/US2005/018031 dated Jun. 28, 2006
International Search Report for PCT/US05/024799 dated Dec. 28, 2006.
International Search Report for PCT/US05/030058 dated Aug. 20, 2007.
International Search Report for PCT/US05/033707 dated Feb. 6, 2006.
International Search Report for PCT/US05/06133 dated Jul. 26, 2007.
International Search Report for PCT/US05/09557 dated Sep. 19, 2005.
International Search Report for PCT/US06/007747 dated Sep. 5, 2006.
International Search Report for PCT/US2006/040747 dated Mar. 17, 2009
International Search Report for PCT/US06/015160 dated Oct. 10, 2006.
International Search Report for PCT/US2006/061307 dated Jan. 9, 2008.
International Search Report for PCT/US2007/020045 dated Jan. 8, 2009.
International Search Report for PCT/US2007/066194 dated Jan. 15, 2008.
International Search Report for PCT/US2008/054926 dated Jan. 26, 2009.
International Search Report for PCT/US2008/057717 dated Jan. 13, 2009.
International Search Report for PCT/US2008/057901 dated Aug. 28, 2008.
International Search Report for PCT/US2008/065332 dated Nov. 28, 2008.

Inyaku, K. et al., "Rapid Detection and Identification of Mycobacteria in Sputum Samples by Nested Polymerase Chain Reaction and Restriction Fragment Length Polymorphisms of dnaJ Heat Shock Protein Gene," 42 J. Med. Sci. 21-31 (1993) ('787 reexamination).

Iqbal et al., " a review of molecular recognition technologies for detection of biological threat agents" Biosensors & Bioelectronics, 15:549-578 (2000).

Isola et al., "MALDIi-TOF mass spectrometric method for detection of hybridized DNA oligomers" Analytical Chemistry (2001) 73:2126-2131.

Ito, T. et al., "Structural Comparison of Three Types of Staphylococcal Cassette Chromosome mec Integrated in the Chromosome in Methicillin-Resistant *Staphylococcus aureus*," Antimicrob. Agents Chemother. (2001)45(5): 1323-1336.

Ito, T. et al., "Insights on antibiotic resistance of *Staphylococcus aureus* from its whole genome: genomic istand SCC," Drug Resist. Updat. (2003) 6(1):41-52.

Jackson et al., "Mass spectrometry for genotyping: an emerging tool for molecular medicine" Molecular Medicine Today (2000) 6:271-276.

Jambrina et al., GenBank: AF005737.1 influenza B virus B/Panama/45/90 polymerase (PB2) mRNA, complete cds, (1997), pp1-3.

Jankowski et al., "Mass spectrometry of DNA. Part 2. Quantitative estimation of base composition" European Journal of Mass Spectrometry in Biochemistry, Medicine, and Environmental Research (1980) 1:45-52.

Jansen et al., "Genotype-by-environment Interaction in Genetic Mapping of Multiple Quantitative Trait Loci" *Theor. Appl. Genet.* (1995) 91:33-37.

Jaulhac, B. et al., "Synthetic DNA probes for detection of genes for enterotoxins A, B, C, D, E and C1967 for TSST-1 in staphylococcal strains," *J. Appl. Bacterial.* (1992) 72(5):386-392.

Jensen et al., "Rapid Identification of Bacteria on the Basis of Polymerase C+A409hain Reaction-Amplified Ribosomal DNA Spacer Polymorphisms"*Appl. Viro Enn. Microbiol.* (1993) 59:945-952.

Jeong, J, et al., "Early Screening of Oxacillin-Resistant *Staphylococcus aureus* and Staphylcoccus epidermidis from Blood Culture," J. Korean Med. Sci . (2002) 17: 168-172.

Jiang et al., "Multiple Trait Analysis of Genetic Mapping for Quantitative Trait Loci Genetics" Genetics Genes (1995) 140:1111-1127.

Jiang et al., "A highly efficient and automated method of purifying and desalting PCR productsfor analysis by electrospray ionization mass spectrometry."*Anal. Biochem* (2003) 316:50-57.

Johnson et al., "Precise molecular weight determination of PCR products of the rRNA intergenic spacer region using electrospray quadrupole mass spectroemtry for differentiation of B. subtilis and B. atrophaeus, closely related species of bacilli" *Journal of Microbiological Methods* (2000)40:241-254.

Jonas, D. et al., "Rapid PCR-Based Identification of Methicillin-Resistant *Staphylococcus aureus* from Screening Swabs," *J. Clin. Microbiol.* (2002) 40(5): 1821-1823.

Jurinke C et al., "Application of nested PCR and mass specctrometry for DNA based virus detection: HBV-DNAS detected in the majority of isolated anti-HBC positive sera", Genetic Analysis: Biomolecular Engineering, Elsevier Science Publishing, US, 14(3):97-102 (Jan. 3, 1998)

Jurinke et al., "Detection of hepatitis B virus DNA in serum samples via nested PCR and MALDI-TOF mass spectrometry" Genetic Analysis: Biomolecular Engineering (1996) 13:67-71.

Jurinke et al., "MALDI-TOF Mass Spectrometry. A Versatile Tool for High-Performance DNA Analysis" *Molecular Biotechnology* (2004) 26(2):147-163.

Kacian et al., "A Replicating RNA Molecule Suitable for a Detailed Analysis of Extracellular Evolution and Replication" Proc. Natl. Acad. Sci. USA 69:3038 (1972).

Kageyama et al., "Rapid detection of human fecal Eubacterium species and related genera by nested PCR method" *Microbiology and Immunology* (2001) 45:315-318.

Kajon, A.E. et al., "Genome Type Analysis of Brazilian Adenovirus Strains of Serotypes 1, 2, 3, 5, and 7 Collected Between 1976 and 1995", J. Med. Virol., 1999, vol. 58, pp. 408-412.

Katano, H., et al., "Identification of Adeno-associated virus contamination in cell and virus stocks by PCR", Biotechniques, Informa Life Sciences Publishing, Westborough, MA, US, 36(4):676-680 (Apr. 2004).

Katayama, Y. et al., "Genetic Organization of the Chromosome Region Surrounding mecA in Clinical Staphylococcal Strains: Role of IS431 -Mediated mecl Deletion in Expression of Resistance in med-Canying, Low-Level Methicillin-Resistant Staphylococcus haemolyticus," Antimicrob. Agents Chemother. (2001)45(7): 1955-1963.

Ke et al., "Development of a PCR Assay for Rapid Detection of Enterococci" *Journal of Clinical Microbiology* (1999) 37:3497-3503.

Kearns, A. M. et al., "Rapid detection of methicillin-resistant staphylococci by multiplex PCR," *J. Hosp. Infect.*

Keller et al., "Empirical Statistical Model to Estimate the Accuracy of Peptide Identifications Made by MS/MS and Database Search" *Anal. Chem* (2002) 74:5383-5392.

Khan, A.S., et al., "An outbreak of Crimean-Congo haemorrhagic fever in the United Arab Emirates, 1994-1995" Am. J. Trop. Med. Hyg., 1997, 57, 519-525.

Khan, S. A. et al., "Simultaneous detection of erythromycin-resistant methylase genes *ermA* and *ermC* from *Staphylococcus spp*. By multiplex-PCR," *Mol. Cell Probes* (1999) 13:381-387.

Kidd, A.H. et al., "Rapid Subgenus Identification of Human Adenovirus Isolates by a General PPCR", J. Clin. Microbiol., 1996, vol. 34, No. 3, pp. 622-627.

Kilbourne, "Influenza Pandemics: Can We Prepare for the Unpredictable?" Viral Immunol. (2004) 17(3):350-357.

Kilbourne, "Influenza Pandemics of the 20th Century" Emerg. Infect. Dis. (2006) 12(1):9-14.

Kilpatrick et al., "Group-Specific Identification of Polioviruses by PCR Using Primer Containing Mixed-Base or Deoxyinosine Residues at Positions of Codon Degeneracy" *J. Clin. Microbiol.* (1996) 34:2990-2996.

Kinney et al., American J. Trop. Med. Hyg., (1998), vol. 59, No. 6, p. 952-954.

Kolbert et al., "" J. Clin. Microbiol. (1998) 36:2640-2644.

Krafft, A.E. et al., "Evaluation of PCR Testing of Ethanol-Fixed Nasal Swab Specimens as an Augmented Surveillance Strategy for Influenza Virus and Adenovirus Identification", J. Clin. Microbiol., 2005, vol. 43, No. 4, pp. 1768-1775.

Krahmer et al., "Electrospray quadrupole mass spectrometry analysis of model oligonucleotides and polymerase chain reaction products: determination of base substitutions, nucleotide additions/deletions, and chemical modifications" *Anal. Chem.* (1999) 71:2893-2900.

Krahmer et al., "MS for identification of single nucleotide polymorphisms and MS/MS for discrimination of isomeric PCR products" *Anal. Chem* (2000) 72:4033-4040.

Kramer, L. D. et al., "Dection of St. Louis Encephalitis and Western Equine Encephalomyelitis RNA in Mosquitoes Tested Without Maintainance of a Cold Chain," J. Am. Mosq. Control Assoc. (2001) 17(4): 213-215.

Kramer, L. D. et al., "Dection of Encephalitis Virusesin Mosquitoes (Diptera: Culicidea) and Avian C2023 Tissues," *J. Med. Entomol.* (2002) 39(2): 312-323.

Kresken, M. et al., "Prevalence of mupirocin resistance in clinical isolates of Staphylococccus aureus and *Staphylococcus epidermidis*: results of the Antimicrobial Resistance Surveillance Study of the Paul-Ehrlich-Society for Chemotherapy, 2001," Int. J. Antimicrob. Agents (2004) 23:577-581.

Krishnan, P.U. et al., "Detection of methicillin and mupirocin resistance in Staphylococcus aureus isolates using conventional and molecular methods: a descriptive study from a burns unit with high prevalence of MRSA," J. Clin. Pathol. (2002) 55:745-748.

Kroes et al., "Baterial diversity within the human subgingival crevice,"Proc. Natl. Acad. Sci. USA (1999) 96:14547-14552.

Krossoy et al., "The putative polymerase sequence of infectious anemia virus suggests a new geneus within the Orthomyxoviridae" Journal of Virology (1999) 73:2136-2142.

Ksiazek, Thomas G., et al., "A novel coronavirus associated with severe acute respiratory syndrome," New England Journal of Medicine, 348(20):1953-1966 (Apr. 10, 2003).

Kupke et al., "Molecular Characterization of Lantibiotic-synthesizing Enzyme EpiD Reveals a Function for Bacterial Dfp Proteins i Coenzyme a Biosynthesis" *Journal of Biological Chemistry* (2000) 275:31838-31846.

Kuroda, M., et al., "Whole genome Sequencing of meticillin-resistant Staphylococcus aureus", The Lancet, 357(9264):1225-1240 (Apr. 21, 2001).

Kwok, S. and R. Hguchi, "Avoiding false positives with PCR" Nature, 1989, 339,237-238.

Labandeira-Rey, M. et al., "Staphylococcus aureus Panton Valentine Leukocidin Causes Necrotizing Pneumonia" Sciencexpress (2007) Jan. 18.

Lacroix et al., "PCR-Based Technique for the Detection of Bacteria in Semen and Urine" J. Microbiol. Meth. (1996) 26:61-71.

Lamb et al., "Sequence of Interrupted and Uninterrupted mRNAs and Cloned DNA Coding for the Two Overlapping Nonstructural Proteins of Influenza Virus" Cell (1980) 21:475-485.

Lambert, A.J. et al., "Detection of North American Eastern and Western Equine Encephalitis Viruses by Nucleic Acid Amplification Assays," J. Clin. Microbiol. (2003)41(1): 379-385.

Lau et al., "Nucleic acid sequence-based amplification methods to detect avian influenza virus" Biochem. Biophys. Res. Commun. (2004) 313:336-342.

Lau et al., "A real-time PCR for SARS-coronavirus incorporating target gene pre-amplification" Biochem. Biophys. Res. Comm. (2003) 312:1290-1296.

Lebedev, Y. et al "Oligonucleotides containing 2-aminoadenine and 5-methycytosine are more effective as primers for PCR amplification than their nonmodified counterparts" Genetic Analysis: Biomolecular Engineering (1996) 13:15-21.

Lee, J.A. et al., "Rapid Identification of Human Adenovirus Types 3 and 7 from Respiratory Specimens via Multiplex Type-Specific PCR", J. Clin. Microbiol., 2005, vol. 43, No. 11, pp. 5509-5514.

Lee, J.H. et al., "Simultaneous Detection of Three Mosquito-Borne Encephalitis Viruses (...) with a Single-Tube Multiplex Reverse Transcriptase Polymerase Chaine Reaction Assay," J. Am. Mosq. Control Assoc. (2002) 18(1): 26-31.

Leif et al., "Isolation and characterization of the proton-translocating NADH: ubiquinone oxidoreductase from Escherichia coli" Eur. J. Biochem. (1995) 230:538-548.

Lengyel, A. et al., "Characterization of the Main Protein Components of Adenovirus Virion and its Possible Use in Laboratory Diagnostics", Acta Microbiol. Immunol. Hung., 1998, vol. 43, Nos. 3-4; pp. 281-283.

Leroy et al., "Diagnosis of Ebola haemorrhagic fever by RT-PCR in an epidemic setting", Journal of Medical Virology, 60:463-467 (2000).

Letter count for Jambrina et al., GenBank: AF005737.1 influenza B virus B/Panama/45/90 polymerase (PB2) mRNA, complete cds, (1997), pp1-2. Same as entry titled "Jambrina et al., GenBank: AF005737.1".

Levi, K. et al., "Evaluation of an Isothermal Signal Amplification Method for Rapid Detection of Methicillin-Resistant Staphylococcus aureus from Patient-Screening Swabs," J. Clin. Microbiol. (2003) 41(7):3 187-3191.

Levine et al., "PCR-based detection of Bacillus anthracis in formalin-fixed tissue from a patient receiving ciprofloxacin" Journal of Clinical Microbiology (2002) 40(11):4360-4362.

Levison et al., "Recent developments of magnetic beads for use in nucleic acid purification" Journal of Chromatography (1998) A 816:107-111.

Lewers et al., "Detection of Linked Qtl for Soybean Brown Stem Rot Resistance in 'BSR 101' as Expressed in a Growth Chamber Environment" Molecular Breeding (1999) 5:33-42.

Le Cann et al., "Quantification of human astroviruses in sewage using real-time RT-PCR" Res. Microbiol. (2004) 155(1):11-15.

Li, Q.-G. et al., "Analysis of 15 Different Genome Types of Adenovirus Type 7 Isolated on Five Continents", J. Virol., 1986, vol. 60, No. 1, pp. 331-335.

Li, Q.-G. et al., "Comparison of 17 Genome Types of Adenovirus Type 3 Identified among Strains Recovered from Six Continents", J. Clin. Microbiol, 1988. Vol. 26, No. 5, pp. 1009-1015.

Li, Q.-G. et al., "Genetic variability of hexon loops 1 and 2 between seven genome types of adenovirus serotype 7", Arch. Virol., 1999, vol. 144, No. 9, pp. 1739-1749.

Li et al., "Screening of the high yield influenza B virus on MDCK cell and cloning of its whole genome" International Congress Series 1263 (2004) 610-614.

Li et al., "Single nucleotide polymorphism determination using primer extension and time of flight mass spectrometry" Electrophoresis (1999) 20:1258-1265.

Li et al., "Evolution of H9N2 influenza viruses from domestic poultry in Mainland China" Virology (2005) 340:70-83.

Liebermann, H. et al., "Mapping of linear epitopes on fibre knob of human adenovirus serotype 5", Virus Res., 2001, vol. 73, No. 2, pp. 145-151.

Liebermann, H. et al., "Mapping of Epitopes on the Fiber Knobs of Human Adenovirus Serotypes 8 and 15". Intervirology, 2002, vol. 45, pp. 59-66.

Lim et al., Genes and Development 17:991-1008 (2003).

Limbach, P.A., et al., "Enzymatic Sequencing of Oligonucleotides with Electrospray Mass Spectrometry" 42nd ASMS Conference on Mass Spectrometry (Jun. 1994) ('787 reexamination).

Limoncu, M. H. et al., "Emergence of phenotypic resistance to ciprofloxacin and levofloxacin in methicillin-resistant and methicillin-sensitive Staphylococcus aureus strains," Int. J. Antimicrob. Agents (2003) 21:420-424.

Lin et al., "Oxidative Damage to Mitochondrial DNA in Atrial Muscle of Patients with Atrial Fibrillation," Free Radical Biology and Medicine, 35(10):1310-1318 (2003).

Lin, B. et al., "Use of Oligonucleotide Microarrays for Rapid Detection and Serotyping of Acute Respiratory Disease-Associated Adenoviruses", J. Clin. Microbiol., 2004, vol. 42, No. 7, pp. 3232-3239.

Lina, G. et al., "Involvement of Panton-Valentine Leukocidin-Producing Staphylococcus aurues in Primary Skin Infections and Pneumonia," Clin. Infect. Dis. (1999) 29(5):1128-1132.

Lina, G. et al., "Bacterial Competition for Human Nasal Cavity Colonization: Role of Staphylococcal agr Alleles," Appl. Environ. Microbiol. (2003) 69(1):18-23.

Linssen, B. et al., "Development of Reverse Transcription-PCR Assays Specific for Detection of Equine Encephalitis Viruses," J. Clin. Microbiol. (2000) 38(4): 1527-1535.

Livermore, D. M., "The threat from the pink corner," Ann. Med. (2003) 35(4):226-234.

Little, et al., "Rapid Sequencing of Oligonucleotides by High-Resolution Mass Spectrometry" J. Am. Chem. Soc. (1994) 116:4893-4897.

Little et al., "MALDI on a Chip: Analysis of Arrays of Low-Femtomole to Subfemtomole Quantities of Synthetic Oligonucleotides and DNA Diagnostic Products Dispensed by a Piezoelectric Pipet" Analytical Chemistry (1997) 69:4540-4546.

Liu et al., "An unusual gene arrangement for the putative chromosome replication origin and circadian expression of dnaN in Synechococcus sp. Strain PCC 7942" Gene (1996) 172:105-109.

Liu et al., "Improving the microdialysis procedure for electrospray ionization mass spectrometry of biological samples" Journal of Mass Spectrometry (1997) 32:425-431.

Liu et al., "Interregional Transmission of the Internal Protein Genes of H2 Influenza Virus in Migratory Ducks from North America to Eurasia" Virus Genes (2004) 29(1):81-86.

Loakes et al., "Nitroindoles as universal bases" Nucleosides and Nucleotides (1995) 14:1001-1003.

Lott, "Nucleotide Sequence Analysis of the 5-8s rDNA and Adjacent ITS2 Region of Candida albicans and Related Species" Yeast, 9:1199-1206 (1999).

Louie, L. et al., "Evaluation of Three Rapid Methods for Detection of Methicillin Resistance in Staphylococcus aureus," J. Clin. Microbiol. (2000) 38(6):2170-2173.

Love et al., "Cloning and sequence of the groESL heat-shock operon of Pasteurella multocida" Gene (1995) 166:179-180.

Lovseth, A. et al., "Modified Multiplex PCR Method for Detection of Pyrogenic Exotoxin Genes in Staphylococcal Isolates," J. Clin. Microbiol. (2004) 42(8):3869-3872.

Lu, X. et al., "Molecular typing of human adenoviruses by PCR and sequencing of a partial region of the hexon gene", Arch. Virol.,., 2006, vol. 15, No. 8, pp. 1587-1602.

Ludwig, S.L. et al., "Prevalence of Antibodies to Adenovirus Serotypes 4 and 7 among Unimmunized US Army Trainees: Results of Retrospective Nationwide Seroprevalence Survey", J. Infect. Dis., (1998) 178, pp. 1776-1778.

Ma, X. X. et al., "Novel Type of Staphylococcal Cassette Chromosome mec Identified in Community-Acquired Methicillin-Resistant Staphylococcus aureus Strains," Antimicrob. Agents Chemother. (2002) 46(4):1147-1152.

Mack and Sninsky, "A sensitive method for the identification of uncharacterized viruses related to known virus groups: Hepadnavirus model system," Proc. Natl. Acad. Sci. USA (1988) 85:6977-6981.

Maiwald et al., "Characterization of contaminating DNA in Taq polymerase which occurs during amplification with a primer set for Legionella 5S ribosomal RNA" Molecular and Cellular Probes (1994) 8:11-14.

Magnuson, VL, "Substrate nucleotide-determined non-templated addition of adenine by Taq DNA polymerase: Implications for PCR-based genotyping and cloning" Biotechniques, 21:700-709 (Oct. 1996).

Malasig, M.D. et al., "Simplified Microneutralization Test for Serotyping Adenovirus Isolates", J. Clin. Microbiol., 2001, vol. 39, No. 8, pp. 2984-2986.

Manian, F. A., "Asymptomatic Nasal Carriage of Mupirocin-Resistant, Methicillin-Resistant Staphylococcus aureus (MRSA) in a Pet Dog Associated with MRSA Infection in Household Contacts," Clin. Infect. Dis. (2003) 36:e26-e28.

Mangrum et al., "Solution composition and thermal denaturation for the production of single-stranded PCR amplicons: piperdine-induced destabilization of the DNA duplex?" *Journal of the American Society for Mass Spectrometry* (2002) 13:232-240.

Marmur et al., "Strand Separation and Specific Recombination in Deoxyribonucleic Acids: Biological Studies" Proc. Natl. Acad. Sci. USA 46:453 (1960).

Martemyanov et al., "Extremely Thermostable Elongation Factor G from Aquifex aeolicus: Cloning, Expression, Purification, and Characterization in a Heterologous Translation System" Protein Expr. Purif. (2000) 18:257-261.

Martineau, F. et al., "Species-Specific and Ubiquitous-DNA-Based Assays for Rapid Identification of Staphylococcus aureus," J. Clin. Microbial. (1998) 36(3):618-623.

Martineau, F. et al., "Development of a PCR Assay for Identification of Staphylococci at Genus and Species Levels," J. Clin. Microbial. (2001) 39(7):2541-2547.

Martin-Lopez, J. V. et al., "Simultaneous PCR detection of ica cluster and methicillin and mupirocin resistance genes in catheter-isolated Staphylococcus," Int. Microbial. (2004) 7:63-66.

Mason et al., "Diversity and linkage of replication and mobilisation genes in Bacillus rolling circle-replicating plasmids from diverse geographical origins" FEMS Microbiol. Ecol. 2002, 42:235-241.

Matray et al., "Synthesis and properties of RNA analogs - oligoribonucleotide N3'->P5' phosphoramidates" *Nucleic Acids Res* (1999) 3976-3985.

Matsuoka, M. et al., "Characteristic expression of three genes, msr(A), mph(C) and erm(Y), that confer resistance to macrolide antibiotics on Staphylococcus aureus," Fems Microbiol. Lett. (2003) 220:287-293.

May, "Percent sequence identity: The need to be explicit" Structure (2004) 12(5):737-738.

Mccabe et al., "Bacterial Species Identification after DNA Amplification with a Universal Primer Pair" *Molecular Genetics and Metabolism* (1999) 66:205-211.

McLafferty et al., "Comparison of Algorithms and Databases for Matching Unknown Mass Spectra" *J. Am. Soc. Mass Spectrom.* (1998).

Mcluckey, S.A., et al., "Ion Trap Tandem Mass Spectrometry Applied to Small Multiply Charged Oligonucleotides with a Modified Base," 5 J. Am. Soc. Mass. Spectrom. 740-747 (1994) ('787 reexamination).

Mehrotra et al., "Multiplex PCR for detection of genes for Staphylococcus aureus enterotoxins, exfoliative toxins, toxic shock syndrome toxin 1, and methicillin resistance", Journal of Clinical Microbiology, Washington, DC US 38(3):1032-1035 (Mar. 1, 2000).

Meiyu et al., "Detection of flaviviruses by reverse transcriptase-polymerase chain reaction with the universal primer set" *Microbiology and Immunology* (1997)41:209-213.

Mellor et al., "Genotype Dependence of Hepatitis C Virus Load Measurement in Commercially Available Quantitative Assays" J. Clin. Microbiol. (1999) 37(8):2525-2532.

Merlino, J. et al., "New Chromogenic Identification and Detection of Staphylococcus aureus and Methicillin-Resistant S. aureus." J. Clin. Microbiol (2000) 38(6): 2378-2380.

Merlino, J. et al., "Rapid Detection of Non-Multidrug-Resistant and Multidrug-Resistant Methicillin-Resistant Staphylococcus aureus Using Cycling Probe Technology for the mecA Gene," Eur. J. Clin. Microbiol. Infect. Dis. (2003) 22: 322.323.

Messmer et al., "Discrimination of Streptococcus pneumoniae from other upper respiratory tract streptococci by arbitrarily primed PCR" *Clinical Biochemistry* (1995) 28:567-572.

Nakao et al., "Development of a Direct PCR Assay for Detection of the Diphtheria Toxin Gene" *J. Clin. Microbiol.* (1997) 35:1651-1655.

Narita et al., "Phage conversion of Panton-Valentine leukocidin in Staphylococcus aures: molecular analysis of a PVL-converting phage, phiSLT" Gene (2001) 265(1-2);195-206.

Naumov et al., "Discrimination of the Soil Yest Species Williopsis stamus and Williopsis suavelons by the Polymerase Chain reaction with the Universal Primer N21" *Microbiology (Moscow) (Translation of Mikrobiologiya)* (20000 69:229-233.

Neumann et al., "Host Range restriction and Pathogenicity in the Context of Influenza Pandemic" Emerg. Infect. dis (2006) 12(6):881-886.

New England Biolabs Catlog (1998-1999) pp. 1, 79, 121, 284.

Newcombe et al. "PCR of peripheral blood for diagnosis of meningococcal disese" (1996) 34:1637-1640.

Ng et al., "Serial analyis of the plasma concentration of SARS coronavirus RNA in pediatric patients with severe acute respiratory syndrome" Clin.Chem. (2003) 49:2085.

Ng et al., "Quantitative analysis and prognostic implicatio of SARS coronavirus RNA in the plasma and serumof patients with severe acute respiratory syndrome" Clin. Chem. (2003) 49:1976-1980.

Nilsson et al., "Evaluation of mitochondrial DNA coding region assays for increased discrimination in forensic analysis" *Forensic Science International: Genetics* (2008) 2:1-8.

Nishikawa et al., "Reconsitution of active remombinant Shiga troxin (Stx)1 from recombinant Stxl-A and Stxl-b subunits independently produced by E. coli clones" *FEMS* (1999) 178:13-18.

Norder et al., "Typing of Hepatitis B Virus Genomes by a Simplified Polymerase Chain reaction" *J. Med. Virol.* (1990) 31:215-221.

Nordhoff, E., et al., "Matrix Assisted Laser Desorption/Ionization Mass Spectrometry of Nucleic Acids with Wavelengths in the Ultraviolet and Infrared" 6 Rapid Commun. Mass Spectrom, 771-776 (1992) ('787 reexamination).

Nubel et al., "PCR primers to amplify 16S rRNA genes from Cyanobacteria," Applied and Environmental Microbiology, 63(8):3327-3332 (Aug. 1997).

Null et al., "Preparation of single-stranded PCR products for electrospray ionization mass spectrometry using the DNA repair enzyme lambda exonuclease" *Analyst* (2000) 125:619-626.

Null et al., "Genotyping of Simple and Compound Short Tandem Repeat Loci Using Electrospray Ionization Fourier Transform Ion Cyclotron Resonance Mass Spectrometry" Analytical Chemistry (2001) 73:4514-4521.

Null et al., "Perspectives on the use of electrospray ionization Fourier transform ion cyclotron resonance mass spectrometry for short tandem repeat genotyping in the post-genome era" *Journal of Mass Spectrometry* (2001) 36:589-606.

Null et al., "Evaluation of sample preparation techniques for mass measurements of PCR products using ESI-FT-ICR mass spectrometry" *Journal of the American Society for Mass Spectrometry* (2002) 13:338-344.

Null et al., "Determination of a correction to improve mass measurement accuracy of isotopically unresolved polymerase chain reaction amplicons by electrospray ionization Fourier transform ion cyclotron resonance mass spectrometry" *Rapid Comm. Mass Spectrom.* (2003) 17:1714-1722.

Null et al., "Implications of hydrophobicity and free energy of solvation for characterization fo nucleic acids by electrospray ionization mass spectrometry" *Anal. Chem.* (2003) 75:1331-1339.

Nunes, E. L. et al., "Dection of ileS-2 Gene Encoding Mupirocin Resistance in Methicillin-Resistan Staphylococcus aures by Multiplex PCR" Diagn. Microbiol. Infect. Dis. (1999) 34(2): 77-81.

Nygren et al., "quantification of HIV-1 Using Multiple Quantitiative Polymerase Chain Reaction Standards and Bioluminometric Detection" Anal. Biochem. (2001) 288(1):28-38.

Oberacher H et al., "Increased foresnic efficiency of DNA fingerprints through simultaneous resoltuion of length and nucleotide variability by high-performance mas spectrometry," Human Mutation 29(3):427-432 (Mar. 2008)+A613+A714.

Metzgar, D. et al., "PCR Analysis of Egyptian Respiratory Adenovirus Isolates, Including Identification of Species, Serotypes and Coinfections", J. Clin. Microbiol., 2005, vol. 43, No. 11, p. 5743-5752.

Miller et al., "A compendium of human mitochondrial DNA control region: development of an international standard forensic database," Croat Med. J. (2001)42:315-327.

Miragaia, M. et al., "Genetic Diversity among Methicillin-Resistant Staphylococcus epidemidis (MRSE)," Microbial Drug Resistance (2005) 11(2):83-93.

Miura-Ochiai, R. et al., "Quantitative detection and rapid identification of human adenoviruses", J. Clin. Microbiol., 2007, vol. 45, No. 3, pp. 958-967.

Monroy, A.M. et al., "Exvaluation of Reverse Transcriptase Polymerase Chain Reaction for the Detection of Eastern Equine Encephalumyelitis Virus during Vector Surveillance," *J. Med. Entomol.* (1996) 33(3): 449-457.

Moore et al., "Development and Evaluation of a Real-Time Nucleic Acid Sequence Based Amplification Assay for Rapid Detection of Influenza a" J. Med. Virol. (2004) 74(4):619-628.

Moricca et al., "Detection of Fusarium oxysporum f.sp. Vasinfectum in cotton tissue by polymerase chain reaction" *Plant Pathology* (1998) 47:486-494.

Morinaga, N. er al., "Purification, Cloning and Charactarizarion of Variant LukE-LukD with Strong Leukocidal Activity of Staphylococcal Bi-Component Leukotoxin Family," Microbiol. Immunol. (2003) 47(1):81-90.

Morse et al., "Nucleotide Sequence of Part of the ropC Gene Encoding the B Subunit of DNA-Dependent Rna Polymerase from some Gram-Positive Bacteria and Comparative Amino Acid Sequence Analysis" *System Appl. Microbiol.* (1996) 19:150-157.

Muddiman et al., "Application of secondary ion and matrix-assisted laser desorption-ionization time-of-flight mass spectrometry for the quantitative analysis of biological molecules" *Mass Spectrometry Reviews* (1995) 14:383-429.

Muddiman et al., "Important aspects concerning the quantification of biomolecules by time-of-flight secondary-ion mass spectrometry" *Applied Spectroscopy* (1996) 50:161-166.

Muddiman et al., "Characterization of PCR Products from Bacilli Using Electrospray Ionization FTICR Mass Spectrometry" *Anal. Chem.* (1996) 68:3705-3712.

Muddiman et al., "Length and base composition of PCR-amplified nucleic acids using mass measurements from electrospray ionization mass spectrometry" *Anal. Chem* . (1997) 69:1543-1549.

Muddiman et al., "Sequencing and Characterization of Larger Oligonucleotides by Electrospray Ionization Fourier Transform Ion Cyclotron Resonance Mass Spectrometry" *Reviews in Analytical Chemistry* (1998) 17:1-68.

Muddiman et al., "Precise mass measurement of a double-stranded 500 base-pair (309 kDa) polymerase chain reaction product by negative ion electrospray ionization fourier transform ion cyclotron resonance mass spectrometry" *Rapid Commun. Mass Spec.* (1999) 13:1201-1204.

Muhammad et al., "Electrospray ionization quadrupole time-of-flight mass spectrometry and quadrupole mass spectrometry for genotyping single nucleotide substitutions in intact polymerase chain reaction products in K-ras and p53" *Rapid Commun. Mass Spectrom* (2002) 16:2278-2285.

Murakami, K. et al., "Identification of Methicillin-Resistant Strains of Staphylococci by Polymerase Chain Reaction," J. Clin. Microbiol. (1991) 29(10):2240-2244.

Mushegian et al., "A minimal gene set for ceullular life derived by comparison of complete bacterial genomes" Proc. Natl. Acad. Sci. USA (1996) 93:10268-10273.

Na et al., "Detection and typing of respiratory adenoviruses in a single-tube multiplex polymerase chain reaction" Journal of Medical Virology (2002) 66:512-517.

Nagpal et al., "Utility of 16S-23S RNA spacer region methodology: how similar are interspace regions within a genome and between strains for closely related organisms?"*Journal of Microbiological Methods* (1998) 33:211-219.

Nagy, M. et al., "Sequence Analysis of Porcine Adenovirus Serotype 5 Fibre Gene: Evidence for Recombination", Virus Genes, 2002, vol. 24, No. 2, pp. 181-185.

Nakagawa et al., "Gene sequences and specific detection for Panton-Valentine leukocidin" Biochem. Biophys. Res. Commun. (2005) 328(4):995-1002.

Oberacher et al., "Analysis of polymerase chain reaction products by on-line liquid chromatography mass spectrometry for genotyping of polymeric short tandem repeat loci" (2001) 73:5109-5115.

Oberste, et al., "Molecular phylogeny and proposed classification of the Simian picornaviruses," J. Virol. (2002) 76:1244-1251.

Oberste, et al., "Improved molecular identification of enteroviruses by RT-PCR and amplicon sequencing," J. Clin. Virol. (2003) 26:375-377.

Oberste, et al., "Molecular epidemiology and type-specific detection of echovirus 11 isolates from the Americas, Europe, Africa, Australia, southern Asia and the Middle East," Virus Res. (2003) 91:241-248.

O'Guinn, M.L. et al., ""Field Detection of Eastern Equine Encephalitis Virus in the Amazon Basin Region of Peru Using Reverse Transcription-Polymerase Chain Reaction Adapted for Field Identification of Arthropod-Borne Pathogens," *Am. J. Trop. Med. Hyg* . (2004) 70(2): 164-171.

Oizumi, N, et al., "Relationship between mutations in the DNA gyrase and topoisomerase IV genes and nadifloxacin resistance in clinically isolated quinolone-resistant Staphylococcus aureus," Journal of Infection and Chemotherapy: Official Journal of the Japan Society of Chemotherapy, 7(3):191-194 (Sep. 2001).

Okada, M. et al., "Detection and sequence-based typing of human adenoviruses using sensitive universal primer sets for the hexon gene", Arch. Virol., 2007, vol. 152, No. 1, pp. 1-9.

Okuma, K. et al., "Dissemination of New Methicillin-Resistant Staphylococcus aureus Clones in the Community," J. Clin. Mcrobiol. (2002) 40(11):4289-4294.

Oliveira, D. C. et al., "Genetic Organization of the Downstream Region of the mecA Element in Methicillin-Resistant Staphylococcus aureus Isolates Carrying Different Polymorphisms of This Region," Antimicrob. dients Chemother. (2000) 44(7): 1906-1910.

Oliveira, D. C. et al., "Multiplex PCR Strategy for Rapid Identification of Structural Types and Variants of the mec Element in Methicillin- Resistant Staphylococcus aureus," Antimicrob. Agents Chemother. (2002) 46(7):2155-2161.

Osiowy, C. et al., "Direct Detection of Respiratory Syncytial Virus, Parainfluenze Virus, and Adenovirus in Clinical Respiratory Specimens by a Multiplex Reverse Transcription-PCR Assay", J. Clin. Microbiol., 1998, vol. 36, No. 11, pp. 3149-3154.

Ounissi, H. et al., "Gene Homogeneity for Aminoglycoside-Modifying Enzymes in Gram-Positive Cocci," Antimicrob. Agents Chemother. (1990) 34(11):2164-2168.

Parson et al., "Population data for 101 Austrian Caucasian mitochondrial DNA d-loop sequences: Application of mtDNA sequence analysis to a forensic case" *Int. J. Legal Med.* (1998) 111:124-132.

Pastorino, B. et al., "Development of a TaqMan PCR assay without RNA extraction step for the detection and quantification of African Chikungunya viruses," *J. Virol. Methods* (2005) 124(1-2): 65-71.

Paterson et al., "Fine Mapping of Quantitative Trait Loci Using Selected Overlapping Recombinant Chromosomes, in an Interspecies Cross of Tomato" *Genetics* (1990) 124:735-742.

Pawa, A. et al., "Co-transfer of plasmids in association with conjugative transfer of mupirocin or mupirocin and penicillin resistance in methicillin-resistant Staphylococcus aureus;" J. Med. Microbiol. (2000) 49: 1103-1107.

Payne et al. Antimicrobials: The challenge of antibiotic resistant bacterial pathogens: the medical need, the market and prospects for new antimicrobial agents. Current Opinion in Microbiology 7:435-438 (2004).

Peng et al., "Rapid detection of Shigella species in environmental sewage by an immunocapture PCR with universal primers" *Applied and Environmental Microbiology* (2002) 68:2580-2583.

Perez-Roth, E. et al., "Multiplex PCR for Simultaneous Identification of Staphylococcus aureus and Detection of Methicillin and Mupirocin Resistance," J. Clin. Microbial. (2001) 39(11):4037-4041.

Peters et al., "Quantification of the detection of Pneumocystis carinii by DNA amplification" Mol. Cell. Probes (1992) 6:115-117.

Pfeffer, M. et al., "Genus-Specific Detection of Alphaviruses by a Semi-Nested Reverse Transcription-Polymerase Chain Reaction," *Am. J. Trop. Med Hyg.* (1997) 57(6): 709-718.

Pfeffer, M. et al., "Specific Detection of Chikungunya Virus Using a RT-PCR/Nested PCR Combination," *J. Vet. Med. B* (2002) 49(1): 49-54.

Pieles, U, et al., Matrix-Assisted Laser Desorption Ionization Time-of-Flight Spectrometry: A Powerful Tool for the Mass and Sequence Analysis of Natural and Modified Oligonucleotides 21 Nucleic Acids Res. 3191-3196 (1993) ('787 reexamination).

Pillai, S.D., :Rapid molecular detection of microbial pathogens: breakthroughs and challenges" Arch Virol., 1997, 13 Suppl., 67-82.

Piper, J. et al., "Commercially Available Technique for Rapid Laboratory Detection of Methicillin.

Poddar, S.K., "Detection of adenovirus using PCR and molecular beacon", J. Virol. Methods., 1999, vol. 82, No. 1, pp. 19-26.

Pomerantz et al., "Determination of oligonucleotide composition from mass spectrometrically measured molecular weight" *Journal of the American Society for Mass Spectrometry* (1993) 4:204-209.

Pring-Akerblom, P., et al., "PCR-based detection and typing of human adenoviruses in clinical samples", Res. Virol., 1997, vol. 148, No. 3, pp. 225-231.

Pring-Akerblom, P., et al., "Multiplex Polymerase Chain Reaction for Subgenus-Specific Detection of Human Adenoviruses in Clinical Samples", J. Med. Virol., 1999, vol. 58, No. 1, pp. 87-92.

Promega T4 Polynucleotide Kinase, Promega Technical Bulletin No. 519, Jul. 2002.

Puthavathana et al., "Molecular characterization of the complete genome of human influenza H5N1 virus isolates from Thailand" J. Gen. Virol. (2005) 86:423-433.

Qadri, S. M. et al., "Rapid Detection of Methicillin-Resistant Staphylococcus aureus by Crystal MRSA ID System,"J. Clin. Microbiol. (1994) 32(7):1830-1832.

Raaum, R. L. et al., "Catarrhine primate divergence dates estimated from complete mitochondrial genomes: concordance with fossil and nuclear DNA evidence," *J. Hum. Evol.* (2005)48:237-257.

Ramisse et al., "Identification and characterization of Bacillus anthracis by multiplex PCR analysis of sequences on plasmids pX01 and pX02 and chromosomal DNA" FEMS Microbiology Letters (1996) 145(1):9-16.

Rangarajan, Sampath, et al., "Rapid identification of emerging infectious agents using PCR and electrospray ionization mass spectrometry" Ann. N.Y. Acad. Of Sci (2007) 1102:109-120.

Reid et al., "Primary diagnosis of foot-and-mouth disease by reverse transcription polymerase chain reaction" Journal of Virological Methods (2000) 89:167-176.

Reilly et al., "Design and use of 16S ribosomal DNA-directed primers in competitive PCRs to enumerate proteolytic bacteria in the rumen" Microb. Ecol. (2002)43:259-270.

Reischl, Frontiers Biosci., 1996, 1, Application of Molecular Biology-Based Methods to the Diagnosis of Infectious Diseases 1, e72-e77.

Reischl, U. et al., "Rapid Identification of Methicillin-Resistant Staphylococcuss aureus and Simultaneous Species Confirmation Using Real-Time Fluorescence PCR," J. Clin. Microbiol. (2000) 38(6):2429-2433.

Roberts, M.M. et al., "Three-Dimensional Structure of the Adenovirus Major Coat Protein Hexon", Science, 1986, vol. 232, No. 4754, pp. 1148-1151.

Robinson, D. A. et al., "Multilocus sequence typing and the evolution of methicillin-resistant Staphylococcus aureus," Clin. Microbiol. Infect. (2004) 10:92-97.

Rong et al., "Design and Application of 60mer oligonucleotide microarray in SARS coronavirus detection", Chinese Sci. Bull., 2003, 48, 1165-1169.

Ross et al., "Discrimination of Single-Nucleotide Polymorphisms in Human DNA Using Peptide Nucleic Acid Probes Detected by MALDI-TOF Mass Spectrometry" *Anal. Chem.* (1997) 69:4197-4202.

Ross et al., "Analysis of DNA fragments from conventional and microfabricated PCR devices using delayed extraction Maldi-Tof mass spectrometry" *Anal. Chem .* (1998) 70:2067-2073.

Ruan et al., "Comparative full-length genome sequence analysis of 14 SARS coronavirus isolates and common mutations associated with the putative origins of infection," Lancet (2003) 361:1832.

Rota et al., "Sequencing of a cDNA clone of the nucleoprotein gene of influenza B/Ann Arbor/1/86" Nucleic Acids Research (1989) 17:3595.

Ruest et al., "Comparison of the Directigen Flu A+B test, the QuickVue Influenza Test, and Clinical Case Definition to Viral Culture and Reverse Transcription-PCR for Rapid Diagnosis of Influenza Virus Infection" J. Clin. Microbiol. (2003) 41(8):3487-3493.

Rupf et al., "Quantitative determination of Streptococcus mutans by using competitive polymerase chain reaction" Eur. J. Oral. Sci. (1999) 107(2):75-81.

Russell, K.L. et al., "Transmission Dynamics and Prospective Environmental Sampling of Adenovirus in a Military Recruit Setting", J. Infect. Dis., 2006, vol. 194, No. 7, pp. 877-885.

Sabat, A. et al., "Comparison of PCR-Based Methods for Typing Staphylococcus aureus Isolates," J. Clin. Microbiol. (2006) 44(10):3804-3807.

Sackesen, C. et al., "Use of polymerase chain reaction for detection of adenovirus in children with or without wheezing", Turk. J. Pediatr., 2005, vol. 47, No. 3, pp. 227-231.

Sakai, H. et al., "Simultaneous Detection of Staphylococcus aureus and Coagulase-Negative Staphylococci in Positive Blood Cultures by Real-Time PCR with Two Fluorescence Resonance Energy Transfer Probe Sets," J. Clin. Microbiol. (2004) 42(12):5739-5744.

Sala et al., "Ambiguous base pairing of the purine analogue 1-(2Odeoxy-B-D-ribofuranosyl)-imidazole 4-carboxamide during PCR" *Nucl. Acids Res.* (1996) 24:3302-3306.

Sambrook et al., Molecular Cloning: A Laboratory Manual, 2nd Edition, Cold Spring Harbor Press, Cold Spring Harbor, NY 1989.

Sampath et al., "Rapid Identification of Emerging Pathogens: Coronavirus" Emerg. Infect. Dis. (2005) 11(3):373-379.

Sanchez et al., "Detection and Molecular Characterizatio of Ebola viruses causing disease in human and nonhuman primates" The Journal of Infectious Diseases, 179(1):S164-S169 (1991).

Sanchez, J.L. et al., "Epidemic of Adenovirus-Induced Respiratory Illness Among US Military Recruits: Epidemiologic and Immunologic Risk Factors in Healthy, Young adults", J. Med. Virol., 2001, vol. 65, No. 4, pp. 710-718.

Sanchez-Seco, M. P. et al., "A generic nested-RT-PCR followed by sequencing for detection and identification of members of the alphavirus genus," J. Virol. Methods (2001) 95(1-2): 153-161.

Sarantis, H. et al., "Comprehensive Detection and Serotyping of Human Adenoviruses by PCR and Sequencing", J. Clin. Microbial., 2004, vol. 42, No. 9, pp. 3963-3969.

Sauer et al., "A novel procedure for efficient genotyping of single nucleotide polymorphisms" *Nucleic Acids Research* (2000) 28:E13.1.

Scaramozzino et al., "Comparison of Flavivirus universal primer pairs and development of a rapid, highly sensitive heminested reverse transcription-PCR assay for detection of flaviviruses targeted to a conserved region of the NS5 gene sequences" *J. Clin. Microbiol.* (2001) 39:1922-1927.

Schena M. "Genome analysis with gene expression microarrays" Bioessays (1996) 18:427-431.

Schmidt et al., "Analysis of a marine pikoplankton community by 16s rRNA gene cloning and sequencing," J. Bacteriol. (1991) 173:4371-4378.

Schmitz, F. J. et al., "Specific information concerning taxonomy, pathogenicity and methicillin resistance of staphylococci obtained by a multiplex PCR." J. Med. Microbiol. (1997) 46:773-778.

Schmitz, F. J. et al., "Development of a multiplex-PCR for direct detection of the genes for enterotoxin B and C, and toxic shock syndrome toxin-1 in Staphylococcus aureus isolates," J. Med. Microbiol. (1998) 47(4):335-340.

Schmitz, F. J. et al., "Development of Resistance to Ciprofloxacin, Rifampin, and Mupirocin in Methicillin-Susceptible and -Resistant Staphylococcus aureus Isolates," Antimicrob. Agents Chemother. (2000) 44(11): 3229-3231.

Schram et al., "Mass Spectrometry of Nucleic Acid Components" *Biomedical Applications of Mass Spectrometry* (1990) 34:203-280.

Schultz et al., "Polymerase chain reaction products analyzed by charge detection mass spectrometry" *Rapid Communications in Mass Spectrometry* (1999) 13:15-20.

Schwartz, M, et al., "Prenatal diagnosis of alpha-1-antitrypsin deficiency using polymerase chain reaction (PCR). Comparison of conventional Rflp methods with PCR used in combination with allele specific oligonucleotides or RFLP analysis," 36 Clin. Genet. 419-426 (1989) ('787 reexamination).

Schweiger et al., "Application of a Fluorogenic PCR Assay for Typing and Subtyping of Influenza Viruses in Respiratory Samples" J. Clin. Microbiol. (2000) 38(4):1552-1558.

Sciacchitano et al., "Analysis of polymerase chain reaction-amplified DNA fragments of clostridium botulinum type E neurotoxin gene by high performance capillary electrophoresis." *J. Liq. Chromatogr. Relat. Technol.* (1996) 19:2165-2178.

Scott-Taylor, T.H. et al., "Conserved Sequences of the Adenovirus Genome for Detection of all Human Adenovirus Types by Hybridization", J. Clin. Microbiol., 1992, vol. 30, No. 7, pp. 1703-1710.

Seifarth, et al., "Rapid identification of all known retroviral reverse transcriptase sequences with a novel versatile detection assay," AIDS Res. Human Retrovir. (2000) 16:721-729.

Sellner, L. N. et al., "Sensitive detection of Ross River virus - a one-tube nested RT-PCR," J. Virol. Methods (1994) 49(1): 47-58.

Sellner, L., "A Single-Tube Nested RT-PCR for the Detection of Ross River Virus," *Methods Mol. Biol.* (1998) 92: 145-152.

Senko et al., "Determination of Monoisotopic Masses and Ion Populations for Large Biomolecules from Resolved Isotopic Distributions," *J. Am. Soc. Mass Spectrom.* (1995) 6:229.

Seshadri et al., "Differential Expression of Translational Elements by Life Cycle Variants of Coxiella burnetii" *Infect. Immun.* (1999) 67:6026-6033.

Shaver et al., "Variation in 16S-23S rRNA intergenic spacer regions among Bacillus subtilis 168 isolates" *Molecular Microbiology* (2001) 42:101-109.

Shaver et al., "Restriction fragment length polymorphism of rRNA operons for discrimination and intergenic spacer sequences for cataloging Bacillus subtilis sub-groups" *J. Microbiol Methods* (2002) 50:215-223.

Shi et al., "Design and application of 60mer oligonucleotide microarray in SARS coronavirus detection" Chinese Sci. Bull. (2003) 48:1165-1169.

Shimaoka, M. et al., "Development of Enzyme-Labeled Oligonucleotide Probe for Detection of mecA gene in Methicillin-Resistant Staphylococcus aureus," J. Clin. Microbiol (1994) 32(8): 1866-1869.

Shimaoka, M. et al., "Detection of the gene for toxic shock syndrome toxin 1 in Siaphylococcus aureus by enzyme-labelled oligonucleotide probes," J. Med. Microbiol. (1996)44:215-218.

Shrestha, N. K. et al., "Rapid Identification of Staphylococcus aureus and the mecA Gene from BacT/Alert Blood Culture Bottles by Using the Lightcycler System," J. Clin. Microbiol. (2002) 40(1):2659-2661.

Simonsen et al., "The Impact of Influenza Epidemics on Hospitalizations" J. Infect. Dis. (2000) 181:831-837.

Skov, R L. et al., "Evaluation of a new 3-h hybridization method for detecting the mecA gene in Staphylococcus aureus and comparison with existing genotypic and phenotypic susceptibility testing methods," J. Antimicrob. Chemother. (1999) 43: 467-475.

Smirnov et al. "Application of Dna-binding polymers for preparation of DNA for analysis by matrix-assisted laser desorption/ionization mass spectrometry." Rapid Comm in Mass Spectrometry (2001) 15:1427-1432.

Smith and Waterman, Adv. Appl. Math., 1981, 2, 482-489.

Song et al., "Identification of cry11-type genes from Bacilus thuringiensis strains and characterization of a novel cry11-type gene" App. Environ. Microbiol. (2003) 69:5207-5211.

Spackman et al., "Development of a real-time reverse transcriptase PCR assay for type a influenza virus and the avian H5 and H7 hemagglutinin subtypes" Journal of Clinical Microbiology (2002) 40:3256-3260.

Spiess, et al., Trehalose is a potent PCR enhancer: Lowering of DNA melting temperature and thermal stabilization of Taq polymerase by the disaccharide trehalose', In: Clinical Chemistry, 2004, 50(7):1256-1259.

Srinivasan et al., "Matrix-assisted laser desorption/ionization time-of-flight mass spectrometry as a rapid screening method to detect mutations causing Tay-Sachs disease" *Rapid Communications in Mass Spectrometry* (1997) 11:1144-1150.

Steffens et al., "Sequence analysis of mitochondrial DNA hybervariable regions using infrared fluorescence detection" *BioTechniques* (1998) 24:1044-1046.

Stephensen CB et al., "Phylogenetic analysis of a highly conserved region of the polymerase gene from 11 coronaviruses and development of a consensus polymerase chain reaction assay" Virus Research Amsterdam NL, 60(2):181-189 (Apr. 1, 1999).

Stone et al., "Rapid detection and simultaneous subtype differentiation of influenza a viruses by real time PCR" (2004) *Journal of Virological Methods* (2004) 117:103-112.

Stoneking et al., "Population variation of human mDNA control region sequences detected by enzymatic amplification and sequence-specific oligonucleotide probes," American Journal of Human Genetics (1991)48:370-382.

Stratagene, 1988 Catalog, p. 39.

Strommenger, B. et al., "Multiplex Pcr Assay for Simultaneous Detection of Nine Clinically Relevant Antibiotic Resistance Genes in Staphylococcus aureus," J. Clin. Microbial. (2003) 41(9):4089 4094.

Studdert, M. J. et al., "Polymerase chain reaction tests for the identification of Ross River, Kunjin and Murray Valley encephalitis virus infections in horses," *Aust. Vet. J.* (2003) 81(1-2): 76-80.

Stuhlmeier, R et al., "Fast, simultaneous, and sensitive detection of staphylococci," J. Clin. Pathol. (2003) 56:782-785.

Sundsfjord, A. et al., "Genetic methods for detection of antimicrobial resistance," APMIS (2004) 112:815-837.

Swanborg, R.H., "Human herpesvirus 6 and Chlamydia pneumoniae as etiologic agents in multiple sclerosis—a critical review"Microbes and Infection, 4:1327-1333 (2002).

Swaminathan, B., et al., Emerging Infectious Diseases, 2001, 7, 382-389.

Swenson, J. M. et al., "Pet-romance of Eight Methods, Including Two New Rapid Methods, for Detection of Oxacillin Resistance in a Challenge Set of Staphylococcus aureus Organisms," J. Clin. Microbial. (2001) 39(10):3785-3788.

Takahashi et al., "Characterization of gryA, gryB, grlA and grlB mutations in fluoroquinolone-resistant clinical isolates of Staphylococcus aureus" *J. Antimicrob. Chemother* (1998) 41:49-57.

Takahata M, et al., "Mutations in the gyrA and grl A genes of quinolone-resistant clinical isolates of methicillin-resistant Staphylococcus aureus," the Journal of Antimicrobial Chemotherapy, 38(3):543-546 (Sep. 1996).

Takayama, R. et al., "Quantification of Adenovirus Species B and C Viremia by Real-Time PCR in Adults and Children Undergoing Stem Cell Transplantation", J. Med. Virol., 2007, vol. 79, No. 3, pp. 278-284.

Takeuchi et al., "Serotyping of Adenoviruses on Conjunctival Scrapings by PCR and Sequence Analysis" *Journal of Clinical Microbiology* (1999) 37:1839-1845.

Talaat et al., "Genome-directed primers for selective labeling of bacterial transcripts for DNA microarray analysis" *Nature Biotechnology* 17:676-682.

Tan, T.Y., "Use of molecular techniques for the detection of antibiotic resistance in bacteria," Expert. Rev. Mol. Diagn. (2003) 3(1):93-103.

Tanabe, F. et al., "The Properties and mec A Gene of the Methicillin-Resistant Staphylccoccus aureus Isolated in Fukushima Medical College Hospital," Fukushima J. Med. Sci (1993) 39(1):35-42.

Tang, K., "Matrix-Assisted Laser Desorption/Ionization Mass Spectrometry of Oligonucleotides,"Dissertation submitted to the Faculty of Vanderbilt University (Aug. 1994) ('787 reexamination).

Tang, K, N.I. Taranenko, S.L. Allman, L.Y. Chang and C.H. Chen, "Double-Stranded DNA Analysis by Matrix Assisted Laser Desorption/Ionization," 42nd ASMS Conference on Mass Spectrometry (Jun. 1994) ('787 reexamination).

Tang, K, N.I. Taranenko, S.L. Allman, L.Y. Chang and C.H. Chen, "Detection of 500-Nucleotide DNA by Laser Desorption Mass Spectrometry," Rapid Commun. Mass Spectrom. 727-730 (Sep. 1994) ('787 reexamination).

Tarassishin, L. et al., "Adenovirus core protein VII displays a linear epitope conserved in a range of human adenoviruses", J. Gen. Virol., 1999, vol. 80, pp. 47-50.

Tarassishin, L. et al., "An epitope on the adenovirus fibre tail is common to all human subgroups", Ach. Virol., 2000, vol. 145, pp. 805-811.

Tatuch et al., "Heteroplasmic mtDNA mutation (T-G) at 8993 can cause Leigh disease when the percentage of abnormal mtDNA is high" Am. J. Hum. Genet. (1992) 50:852-858.

Taubenberger et al., "Characterization of the 1918 influenza virus polymerase genes" Nature (2005) 437:889-893.

Taylor, L.H., et al., Philos. Trans. R. Soc. Lond B. Biol. Sci. 2001, 356, 983-989.

Tenover, F. C. et al., "Characterization of a Strain of Community-Associated Methicillin-Resistant Slaphylococcus aureus Widely Disseminated in the United States," J. Clin.Microbiol. (2006) 44(1):108-118.

Teramura, T. et al., "Quantitative detection of serum adenovirus in a transplant recipient", Lancet, 2002, Vol. 359, pp. 1945.

Thiel, et al., "Infectious RNA transcribed in vitro from a cDNA copy of the human coronavirus genome cloned in vaccinia virus" J. Gen. Virology 2001 82:1273-1281.

Thompson et al., "Influenza-Associated Hospitalizations in the United States" JAMA (2004) 292:1333-1340.

Thompson et al., Nucleic Acid Res., 22, 4673-80.

Tokue, Y. et al., "Comparison of a Polymerase Chain Reaction Assay and a Conventional Microbiologic Method for Detection of Methicillin-Resistant Slaphylococcus aureus," Antimicrob. Agents Chemother. (1992) 36(1):6-9.

Tong et al., "Ligation reaction specificities of an NAD+-dependent DNA ligase from the hyperthermophile Aquifex aeolicus" Nucleic Acids Res (2000) 28:1447-1454.

Top, F., Jr., "Control of Adenovirus Acute Respiratory Disease in U.S. Army Trainees", Yale J. Biol. Med., 1975, vol. 48, pp. 185-195.

Torroni et al., "Classification of European mtDNAs from an Analysis of Three European Populations" Genetics (1996) 144:1835-1850.

Towner, K. J. et al., "Development and evaluation of a PCR-based immunoassay for the rapid detection of methicillin-resistant Staphylococcus aureus," J. Med. Microbial. (1998) 47:607-613.

Tsuneyoshi et al., "Mass spectrometric gene diagnosis of one-base substitution from polymerase chain reaction amplified human DNA" (1997) 11:719-722.

Tsunoda et al., Time and Memory Efficient Algorithm for Extracting Palindromic and Repetitive Subsequences in Nucleic Acid Sequences" Pacific Symposium on Biocomputing (1999)4:202-213.

Udo, E. E. et al., "Rapid detection of methicillin resistance in staphylococci using a slide latex agglutination kit," Int. J Antimicrob. Agents. (2000) 15(1):19-24.

Udo, E. E. et al., "Genetic analysis of methicillin-resistant Staphylococcus aureus expressing high-and low-level mupirocin resistance."J. Med. Microbiol. (2001) 50:909-515.

Udo, E. E. et al., "A chromosomal location of the mupA gene in Staphylococcus aureus expressing high-level mupirocin resistance," J. Antimicrob. Chemother. (2003) 51:1283-1286.

Unal et al., "" J. Clin. Microbiol. (1992) 30:1685-1691.

Unpublished U.S. Appl. No. 10/318,463 filed Dec. 13, 2002.
Unpublished U.S. Appl. No. 10/323,186 filed Dec. 18, 2002.
Unpublished U.S. Appl. No. 10/323,187 filed Dec. 18, 2002.
Unpublished U.S. Appl. No. 10/324,721 filed Dec. 18, 2002.
Unpublished U.S. Appl. No. 10/728,486 filed Dec. 5, 2003.
Unpublished U.S. Appl. No. 11/209,439 filed Aug. 23, 2005.
Unpublished U.S. Appl. No. 11/233,630 filed Sep. 2, 2005.
Unpublished U.S. Appl. No. 60/604,329 filed Aug. 24, 2004.
Unpublished U.S. Appl. No. 60/632,862 filed Dec. 3, 2004.
Unpublished U.S. Appl. No. 60/639,068 filed Dec. 22, 2004.
Unpublished U.S. Appl. No. 60/648,188 filed Jan. 28, 2005.
Unpublished U.S. Appl. No. 60/658,248 filed Mar. 3, 2005.

Upton, A. et al., "Mupirocin and Staphylococcus aureus: a recent paradigm of emerging antibiotic resistance," J. Antimicrob. Chemother. (2003) 51: 613-617.

Vabret, A., et al., "Development of a PCR-and hybridization-based assay (PCR Adenovirus Consensusa) for the detection and the species identification of adenoviruses in respiratory specimens", J. Clin. Virol., 2004, vol. 31, No. 2, pp. 116-122.

Van Aerschot et al., "In search of acyclic analogues as universal nucleosides in degenerate probes" Nucleosides and Nucleotides (1995) 14:1053-1056.

Van Baar et al., "Characterization of Bacteria by Matrix Assisted Laser Desorption/Ionization and Electrospray Mass Spectrometry" FEMS Microbiol. Review (2000) 24:195-219.

Van Camp et al., "Amplification and sequencing of variable regions in bacteria 23S ribosomal RNA genes with conserved primer sequences" Current Microbiology (1993) 27:147-151.

Van Der Vossen et al., "DNA based typing, identification and detection systems for food spoilage microorganisms: development and implementation" Int. J. Food Microbiol. (1996) 33:35-49.

Van Der Zee, et al., "Rapid and alternative screening methods for microbiological analysis" J. AOAC Int., 1997, 80, 934-940.

Van Dinten et al., " Proteolytic Processing of the Open Reading Frame 1b-Encoded Part of Arterivirus Replicase Is Mediated by nsp4 Serine Protease and Is Essential for Virus Replication" J. Virology, 1999, vol. 73, pp. 2027-2037.

Van Elden et al., "Simultaneous Detection of Influenza Viruses A and B Using Real-Time Quantitative PCR" J. Clin. Microbiol. (2001) 39(1):196-200.

Van Elden et al., "Clinical diagnosis of influenza virus infection: evaluation of diagnostic tools in general practice" Br. J. Gen. Pract. (2001) 51:630-634.

Van Ert et al., "Mass spectrometry provides accurate characterization of two genetic marker types in Bacillus anthracis" Biotechniques (2004) 37:642-644, 646, 648.

Van Leeuwen, W. B. et al., "Rapid Detection of Methicillin-Resistance in Staphylococus aureus Isolates by the MRSA-Screen Latex Agglutination Test,"J. Clin. Microbiol. (1999) 37(9):3029-3030.

Van Leeuwen, W. B. et al., "Multilocus Sequence Typing of Staphylococcus aureus with DNA Array Technology," J. Clin. Microbiol. (2003) 41(7):3323-3326.

Vanderhallen et al., "Identification of Encephalomyocarditis Virus in Clinical Samples by Reverse Transcription-PCR Followed by Genetic Typing Using Sequence Analysis"J. Clin. Microbiol. (1998) 36:3463-3467.

Vannuffel, P. et al.. "Specific Detection of Methicillin-Resistant Staphylococcus Species by Multiplex PCR," J. Clin Microbiol. (1995) 33(11):2864-2867.

Vannuffel, P. et al., "Rapid and Specific Molecular Identification of Methicillin-Resistant Staphylococcus aureus in Endotracheal Aspirates from Mechanically Ventilated Patients," J Clin. Microbiol. (1998) 36(8):2366-2368.

Videla, C. et al., "Genomic analysis of adenovirus isolated from Argentinean children with acute lower respiratory infections", J. Clin. Virol., 1999, vol. 14, pp. 67-71.

Vilchez, Regis a et al., "Detection of polyomavirus simian virus 40 tumor antigen DNA in AIDS related systemic non-Hodgkin lymphoma," J. Aids Journal of Acquired Immune Deficiency Syndromes, 29(2):109-116 (Feb. 1, 2002).

Voelter C et al., "Screening human tumor samples with a broad-spectrum polymerase chain reaction method for the detection of polyomaviruses", VIROLOGY, Academic Press, Orlando, US 237(2):389-396 (Oct. 1997).

Volokhov et al. Microarray analysis of erythromycin resistance determinants. Journal of Applied Microbiology 95:787-798 (2003).

Von Eiff, C. et al., "Pathogenesis of infections due to coagulase-negative staphylococci," Lancet Infect. Dis. (2002) 2:677-685.

Walker, E. S. et al., "A Decline in Mupimcin Resistance in Methicillin-Resistant Staphylococcus aureus Accompanied Administrative Control of Prescriptions," J. Clin. Microbiol. (2004) 42(6):2792-2795.

Wallace, et al., "The Enigma of Endonuclease VII. DNA Repair," 2:441-453 (2003).

Wallet, F. et al., "Choice of a routine method for detecting methicillin-resistance in staphylococci,"I Antimicrob. Chemother. (1996) 37:901-909.

Walters et al., "Genotyping single nucleotide polymorphisms using intact polymerase chain reaction products by electrospray quadrupole mass spectrometry" Rapid Communications in Mass Spectrometry. (2001) 15:1752-1759.

Ward et al ., "Design and performance testing of quantitative real time PCR assays for influenza a and B viral load measurement" Journal of Clinical Virology (2004) 29:179-188.

Weissenbacher, M. et al., "Etiologic and Clinical Evaluation of Acute Lower Respiratory Tract Infections in Young Argentinean Children: An Overview", Rev. Infect. Dis., 1990, vol. 12, Suppl. 8; pp. S889-898.

Welham et al., "The Characterization of Micro-organisms by Matrix-assisted Laser Desorption/Ionization Time-of-flight Mass Spectrometry" Rapid Communications in Mass Spectrometry (1998) 12:176-180.

Wertheim, H. F. et al., "Effect of Mupirocin Treatment on Nasal, Pharyngeal, and Perineal Carriage of Staphylococcus aureus in Healthy Adults," Antimicrob. Agents Chemother. (2005) 49(4):1465-1467.

Whiley, David M et al., "Simultaneous detection and differentiation of human polyomaviruses JC and BK by a rapid and sensitive PCR-ELAHA assay and a survey of the JCV subtypes within an Australian population," Journal of Medical Virology, 72(3):467-472 (Mar. 2004).

Wichelhaus, T. A. et al., "Rapid Detection of Epidemic Strains of Methicillin-Resistant Staphylococcus aureus," J. Clin. Microbiol. (1999) 37(3):690-693.

Wickham, T.J., "Targeting adenovirus", Gene Therapy, 2000, vol. 7, pp. 110-114.

Widjojoatmodjo et al., "Rapid Identification of Bacteria by PCR-Single-Strand Conformation Polymorphism" Journal of Clinical Microbiology (1994) 3002-3007.

Winger et al., "High resolution accurate mass measurements of biomolecules using a new electrospray ionization ion cyclotron resonance mass spectrometer" J. Am. Soc. Mass Spectrom. 4, 566, 1993.

Wolter et al., "Negative Ion FAB Mass Spectrometric Analysis of Non-Charged Key Intermediates in Oligonucleotide Synthesis: Rapid Identification of Partially Protected Dinucleoside Monophosphates" Biomed. Environ. Mass Spectrom. (1987) 14:111-116.

Woo et al., "Identification of Leptospira inadai by continuous monitoring of fluorescence during rapid cycle PCR" Systematic and Applied Microbiology (1998) 21:89-96.

Wood, S.R. et al., "Rapid Detection and Serotyping of Adenovirus by Direct Immunofluorescence", J. Med. Virol., 1997, vol. 51, No. 3, pp. 198-201.

Wright et al., "Typing and Subtyping of Influenza Viruses in Clinical Samples by PCRr" J. Clin. Microbiol. (1995) 33(5):1180-1184.

Wu et al., "Genetic Organization of the mecA Region in Methicillin-Susceptible and Methicillin-Resistant Strains of Staphylococcus sciuri" J. Bacteriol. (1998) 180(2):236-242.

Wu et al., "Establishment of a fluorescent polymerase chain reaction method for the detection of SARS-associated coronavirus and its clinical application" Chin. Med. J. (2003) 116:988-990.

Wunschel et al., "Discrimination Among the B. Cereus Group, in Comparison to B. Subtilis, by Structural Carbohydrate Profiles and Ribosomal RNA Spacer Region PCR" System. Appl. Microbiol. (1994) 17:625-635.

Wunschel et al., "Analysis of double-stranded polymerase chain reaction products from the Bacillus cereus group by electrospray ionization Fourier transform ion cyclotron resonance mass spectrometry" Rapid Communications in Mass Spectrometry (1996) 10:29-35.

Wunschel et al., "Mass spectrometric characterization of DNA for molecular biological applications: Advances using MALDI and ESI" Advances in Mass Spectrometry (1998) 14:Chapter 15/377-Chapter 15/406.

Wunschel et al., "Heterogeneity in baciullus cereus PCR products detected by ESI-FTICR mass spectrometry" Anal. Chem. (1998) 70:1203-1207.

Xu et al., "Intercontinental Circulation of Human Influenza a(H1N2) Reassortant Viruses During the 2001-2002 Influenza Season" J. Infect. Dis. (2002):186:1490-1493.

Xu, W. et al., "Species-Specific Identification of Human Adenoviruses by a Multiplex PCR Assay", J. Clin. Microbiol., 2000, vol. 38, No. 11, pp. 4114-4120.

Xu, W. et al., "Type-Specific Identification of Human Adenovirus, 3, 7, and 21 by a Multiplex PCR Assay", J. Med. Virol., 2001, vol. 64, No. 4, pp. 537-542.

Yao et al., "Mass Spectrometry Based Proteolytic Mapping for Rapid Virus Detection" Anal. Chem. (2002) 74:2529-2534.

Yasui et al., "A specific oligonucleotide primer for the rapid detection of Lactobacillus lindneri by polymerase chain reaction" Can. J. Microbiol. (1997)43:157-163.

Yun, H J et al., "Increased antibacterial activity of OW286, a novel fluoronaphthyridone antibiotic, against Staphylococcus aureus strains with defined mutations in DNA gyrase and toposiomerase IV", International Journal of Antimicrobial Agents, Amsterdam, NL, 25(4):334-337 (Apr. 1, 2005).

Zeng et al., "Precision Mapping of Quantitative Trait Loci" Genetics (1994) 136:1457-1468.

Zhang et al., "Detectiona and identification of human influenza viruses by the polymerase chain reaction" J. Virol. Methods (1991) 33(1-2):165-189.

Zhang, K. et al., "New Quadriplex PCR Assay for Detection of Methicillin and Mupirocin Resistance and Simultaneous Discrimination of Staphylococcus aureus from Coagulase-Negative Staphylococci," J. Clin. Microbiol. (2004) 42(11):4947-4955.

Zhang, Y.-Q. et al., "Genome-based analysis of virulence genes in a non-biofilm-forming Staphylococcus epidemidis strain (ATCC 12228):" Mol. Microbiol. (2003) 49(6):1577-1593.

European Supplemental Search Report for 05753037 dated August 28, 2009.

* cited by examiner

US 7,714,275 B2

MASS SPECTROMETRY WITH SELECTIVE ION FILTRATION BY DIGITAL THRESHOLDING

CROSS-REFERENCE TO RELATED APPLICATIONS

This application claims the benefit of priority of U.S. Provisional Application Ser. No. 60/574,042 filed May 24, 2004, the entire disclosure of which is incorporated herein by reference in its entirety.

FIELD OF THE INVENTION

The invention relates to the field of detection and characterization of large analytes, such as biomolecules, by molecular mass analysis.

BACKGROUND OF THE INVENTION

Mass spectrometry has been used for many decades in the characterization of small organic molecules. The technique typically involves the ionization of molecules in the sample to form molecular ions by subjecting the sample to an electron beam at a very low pressure. The molecular ions are then focused and accelerated by an electric field into a magnetic field or quadrupole. The ions are separated in the magnetic field or quadrupole according to the ratio of the mass of the ion m to the charge on the ion z (m/z). After passing through the field, the ions impinge upon a detector which determines the intensity of the ion beam and the m/z ratio, and these data are used to create the mass spectrum of the sample.

With the increasing interest in larger molecules, especially biomolecules such as nucleic acids and proteins, new techniques in the field of mass spectrometry are continually being developed to characterize these molecules.

In recent years the performance of commercially available mass spectrometers has seen significant improvement due, in part, to the availability of improved core components including more stable power supplies, faster digitizers, and more sophisticated fabrication methods for ion optic elements. Particularly noteworthy are the newest generation ESI-TOF mass spectrometers which, from several vendors in a variety of configurations, are now routinely yielding the types of mass measurement accuracy and mass resolution previously attainable only on high end sector or Fourier transform ion cyclotron resonance (FTICR)-based platforms. As such, the use of such bench top instruments by the bioanalytical community continues to expand as these instruments are increasingly being made available to scientists and technicians with a broad range of analytical needs. Accordingly, a number of increasingly sophisticated automation schemes are emerging, many incorporating some form of liquid chromatography (LC) as an on-line sample purification step to support high throughput QC or drug screening activities. While there are a number of applications in which some form of LC is a requisite step that facilitates the analysis of very complex mixtures, it is also used frequently as a generic desalting/purification protocol to prepare relatively pure analyte fractions for MS analysis.

Low molecular weight chemical noise is often the limiting factor in overall MS performance as the presence of high levels of low molecular weight components, such as polymers and buffer constituents, can drastically limit the spectral dynamic range and adversely affect mass accuracy. While LC is often used to reduce the adverse affects of such backgrounds, constraints on sample throughput and issues associated with solvent usage/disposal must be considered as part of the laboratory work flow. Additionally, LC is often used as a purification step (as opposed to a separation step) to render analytes amenable to MS analysis. Consequently, there is an increasing need for simple methods to reduce the chemical noise floor and render less than "pristine" samples amenable to mass spectrometric analysis.

The present invention satisfies this need, as well as others, by providing systems and methods for digital filtration of mass spectral signals arising from singly-charged low molecular weight components such as solution additives and matrix modifiers without significantly altering the mass spectral signals of larger analytes such as biomolecules.

SUMMARY OF THE INVENTION

The present invention is directed to methods of identifying a multiply-charged ion. A mass spectrometer that comprises the following components is provided: (i) an ion detector, (ii) a digitizer that converts an analog signal to a digital signal, (iii) an analog signal transfer means for transferring an analog signal from the detector to the digitizer, and (iv) a digital threshold filter which is in digital data communication with the digitizer. A digital signal threshold can be set at the digital threshold filter and, in response to a digital signal input from the digitizer, the digital threshold filter independently outputs a digital signal to a data file only if the digital signal input is greater than the specified digital signal threshold. The continuing step of the method is then effected by specifying a digital signal threshold such that, upon a mass spectrometer measurement of the multiply-charged ion, the filtered digital signal output to the data file originates from the detection of the multiply-charged ion and excludes digital signal output from analog signals arising from singly-charged ions.

The present invention is also directed to methods for determining the molecular mass of a plurality of analytes in a mixture. A mass spectrometer that comprises the following components is provided: (i) an ion detector, (ii) a digitizer that converts an analog signal to a digital signal, (iii) an analog signal transfer means for transferring an analog signal from the detector to the digitizer, and (iv) a plurality of digital threshold filters, each in digital data communication with the digitizer. A digital signal threshold can be independently set at any of the plurality of digital threshold filters, each of which is in digital data communication with the digitizer and, in response to a digital signal input from the digitizer, independently outputs a digital signal to a corresponding data file only if the digital signal input is greater than the specified digital signal threshold. The continuing steps of the method are then effected by specifying a unique digital signal threshold at some members of the plurality of digital threshold filters, making a mass spectrometer measurement of the mixture, wherein each unique digital signal threshold differentially filters digital signals arising from the plurality of analytes and produces a unique digital signal output to each corresponding data file. The measurement results in storage of a plurality of data files. In the final step, each of the plurality of data files is analyzed and the molecular mass of at least one member of the plurality of analytes is contained in each of the plurality of data files.

The present invention is also directed to methods for calibrating a mass spectrum of an analyte. A mass spectrometer that comprises the following components is provided: (i) an ion detector, (ii) a digitizer that converts an analog signal to a digital signal, (iii) an analog signal transfer means for transferring an analog signal from the detector to the digitizer, and (iv) a plurality of digital threshold filters, each in digital data communication with the digitizer. A digital signal threshold can be independently set at any of the plurality of digital threshold filters, each of which is in digital data communication with the digitizer and, in response to a digital signal input from the digitizer, independently outputs a digital signal to a corresponding data file only if the digital signal input is greater than the specified digital signal threshold. The continuing steps of the method are then effected by specifying a first unique digital signal threshold at one digital threshold filter such that digital signal output to a first data file has signals from both the analyte and a calibrant ion and then specifying a second unique digital signal threshold at another digital threshold filter such that the digital signal output to a second data file has signals from the analyte but not the calibrant. The second data file is subtracted from the first data file to obtain a calibration file which is then used to calibrate the mass spectrum.

The present invention is also directed to a system comprised of a mass spectrometer that comprises the following components: (i) an ion detector, (ii) a digitizer that converts an analog signal to a digital signal, (iii) an analog signal transfer means for transferring an analog signal from the detector to the digitizer, and (iv) a plurality of digital threshold filters for setting a digital signal threshold which are each in digital data communication with the digitizer and in response to a digital signal input from the digitizer independently outputting a digital signal to a corresponding data file only if the digital signal input is greater than the specified digital signal threshold. The system has a plurality of data files and a plurality of parallel digital signal output transferring means, each of which is in digital data communication with one of the plurality of digital threshold filters and a corresponding data file from the plurality of data files.

BRIEF DISCUSSION OF THE DRAWINGS

FIG. 1 shows the detector response intensity as a function of digital signal threshold value (in this case indicated by cutoff voltage) of analyte ions having similar m/z ratios but differing in molecular weights. Circles: 140-mer oligonucleotide (m/z=1232.9), squares: 70-mer oligonucleotide (m/z=1199), diamonds: 38-mer oligonucleotide (m/z=1174.7), crosses: 12-mer oligonucleotide (m/z=1233) and triangles: polypropylene glycol (PPG-m/z=1236).

Figure 2:
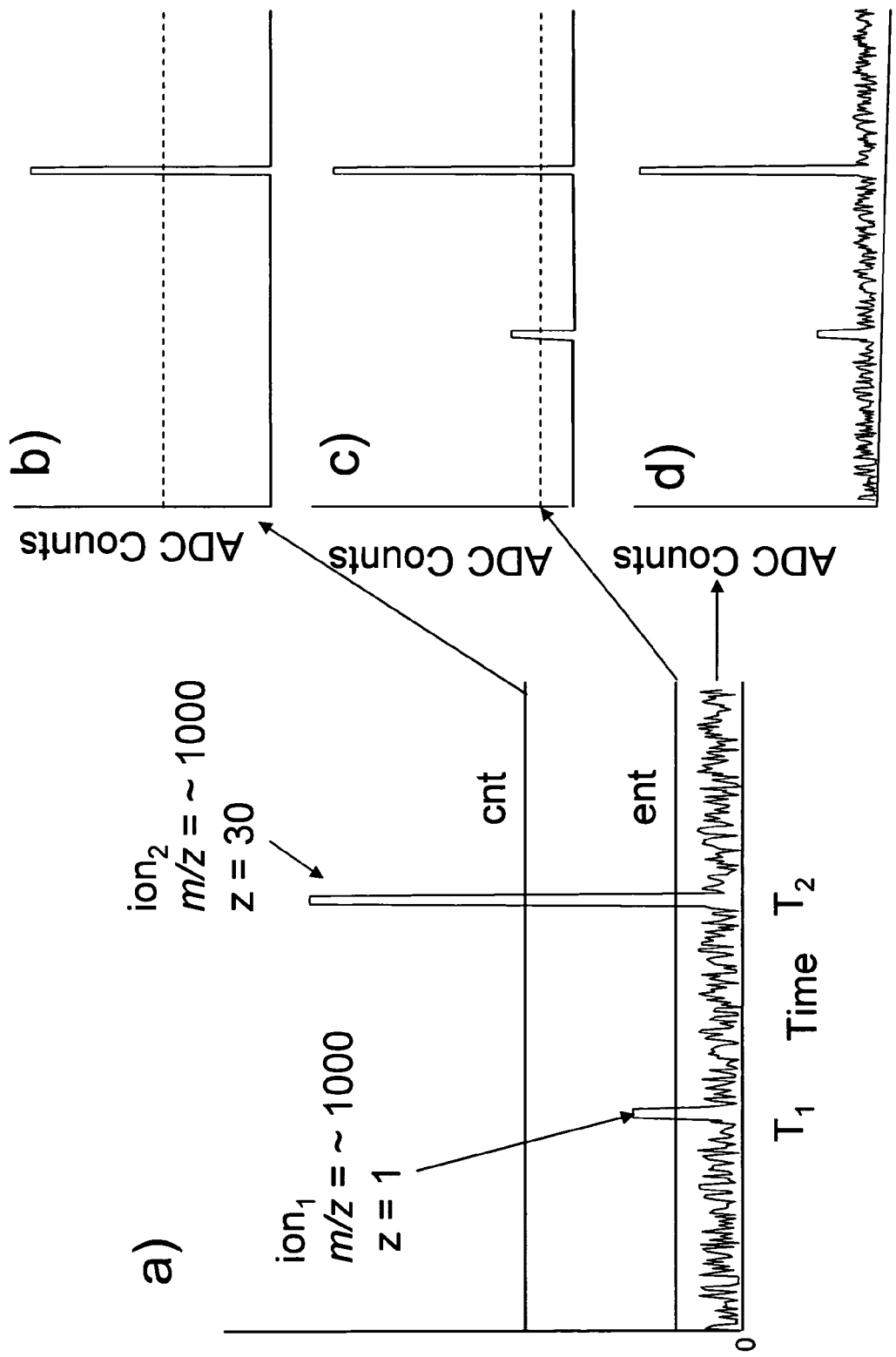

FIG. 2 is a schematic representation of the effects of specifying digital signal thresholds on mass spectra. FIG. 2a depicts the raw digitizer (ADC, analog digital converter) output from a theoretical single scan containing a singly-charged ion (ion1) which strikes the detector at T1 and a large multiply-charged ion (ion2) which strikes the detector at T2. FIGS. 2b and 2c indicate a spectrum with a high and low digital signal threshold respectively. FIG. 2d indicates a spectrum without a digital signal threshold and detector "white noise" is visible in the spectrum.

Figure 3:
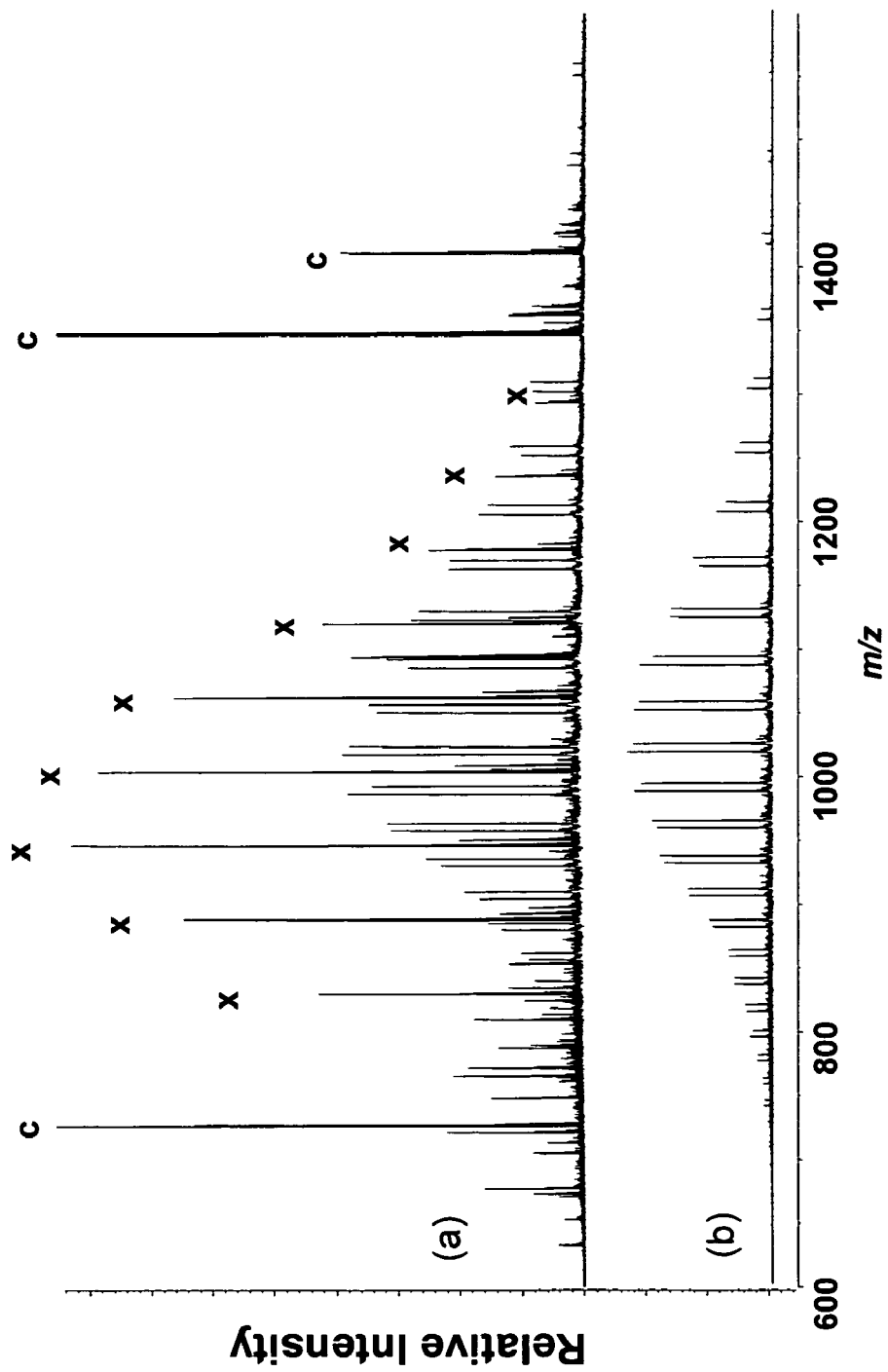

FIG. 3 displays mass spectra of a PCR product. FIG. 3a is an ESI-TOF mass spectra of a 140-mer PCR product acquired at a normal (3 mV) digital threshold setting. The sample contains a contaminating amount of polypropylene glycol (PPG) relatively high levels of singly charged peptides (which serve as internal mass standards). Peaks labeled with "x" indicate signals from the PPG and "c" represents signals from the peptide mass standards. FIG. 3b is an ESI-TOF spectrum of the same sample of PCR product obtained at a digital threshold setting of 15 mV. Contaminants and mass standards have been filtered out of the spectrum.

Figure 4:
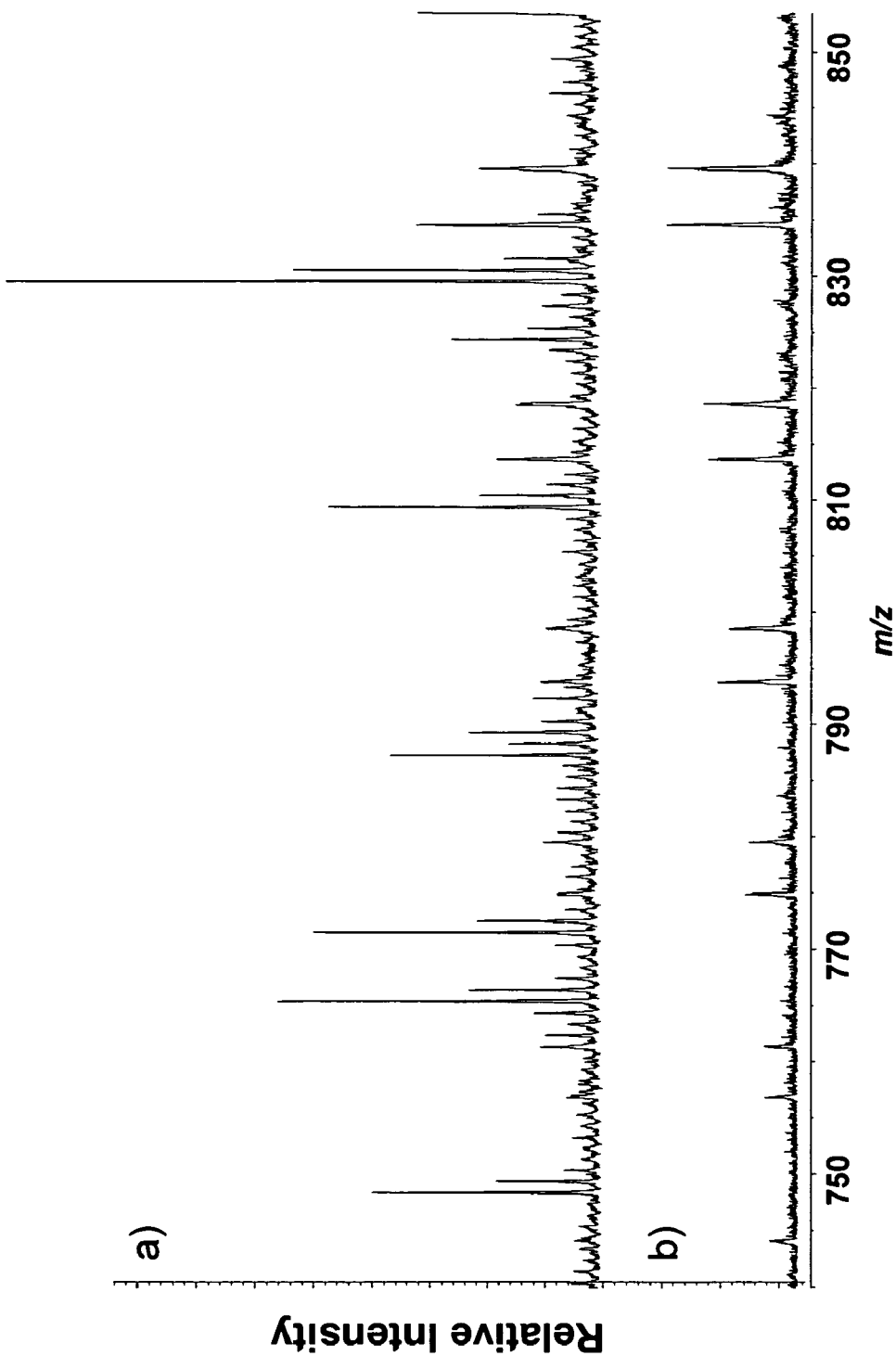

FIG. 4 is an expanded region of the ESI-TOF spectra from FIG. 3 in which the relatively low abundance high charge states of the PCR amplicon are detected. The effective signal to noise of the spectrum in FIG. 4a is defined by the signal to chemical noise ratio, while the effective signal to noise of the spectrum in FIG. 4b is defined by the signal to electronic noise ratio.

Figure 5:
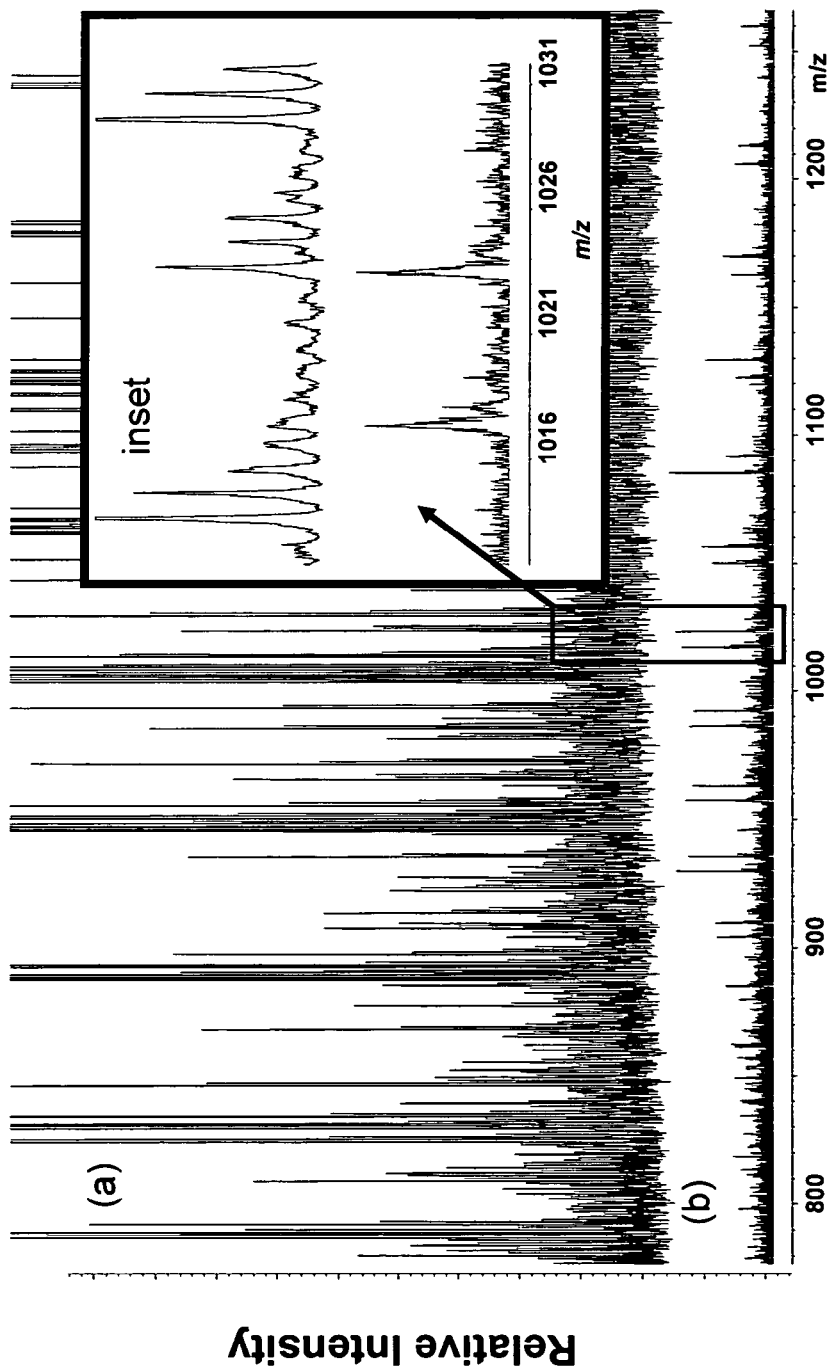

FIG. 5 exhibits ESI-TOF spectra of a solution containing approximately 0.5 nM PCR product in the presence of 500 nM PPG was characterized at low (FIG. 5a) and high (FIG. 5b) threshold settings As shown in the inset, the top spectrum is also inundated with other chemical noise components and the peak-at-every-mass background precludes the detection of the low level PCR products. When the digital signal threshold is set such that signals from singly charged species are not detected, a distinct signature for the low level amplicon is detected.

Figure 6:
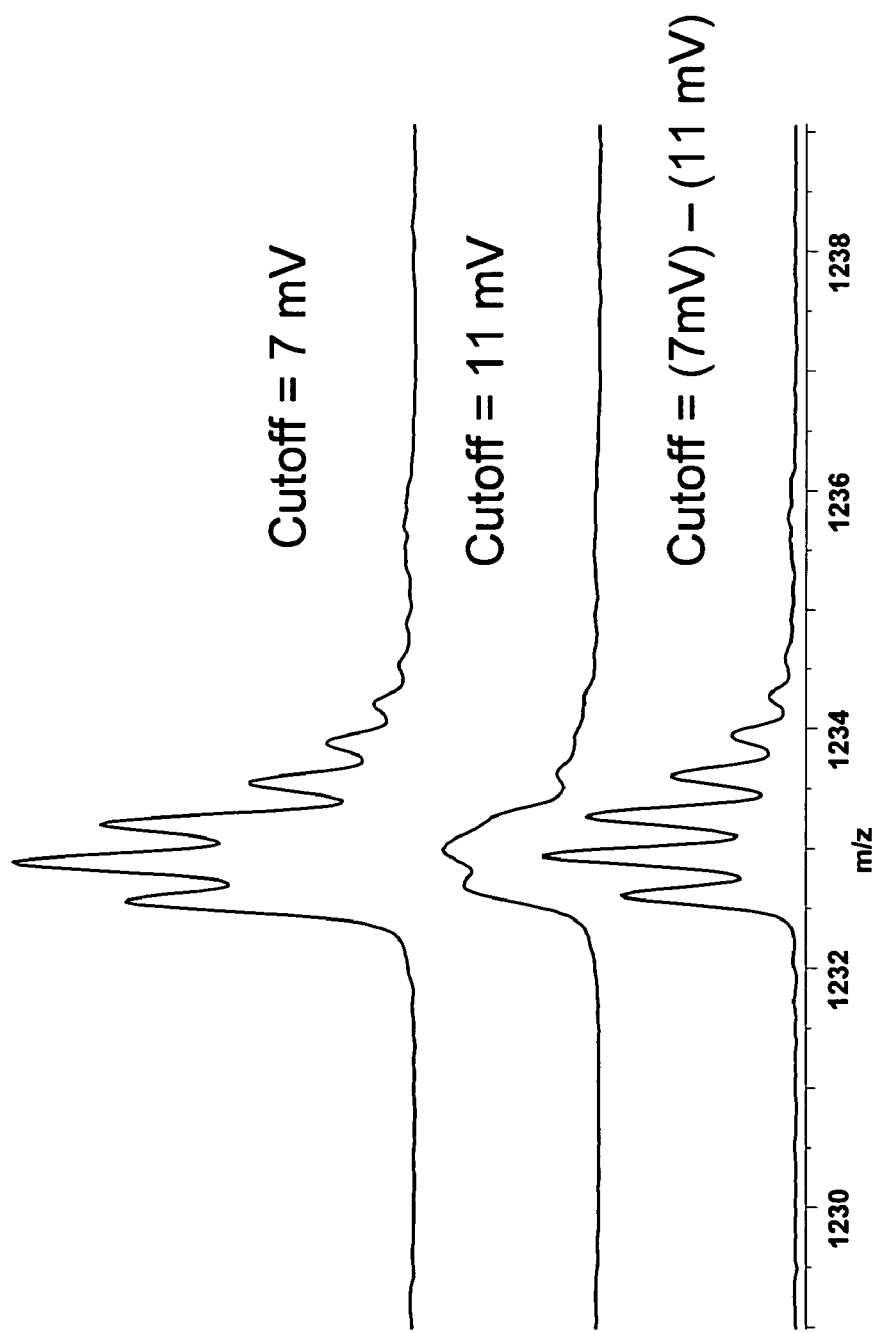

FIG. 6 indicates two overlapping peaks of a 140-mer oligonucleotide and of a 12-mer oligonucleotide which can be resolved through acquisition of data with different digital signal thresholds. The top spectrum was obtained with a digital signal threshold setting of 7 mV. The middle spectrum was obtained with a digital signal threshold setting of 11 mV. The bottom spectrum was obtained by subtraction of the middle spectrum from the top spectrum to obtain a clean isotopically resolved spectrum of the 12-mer oligonucleotide.

Figure 7:
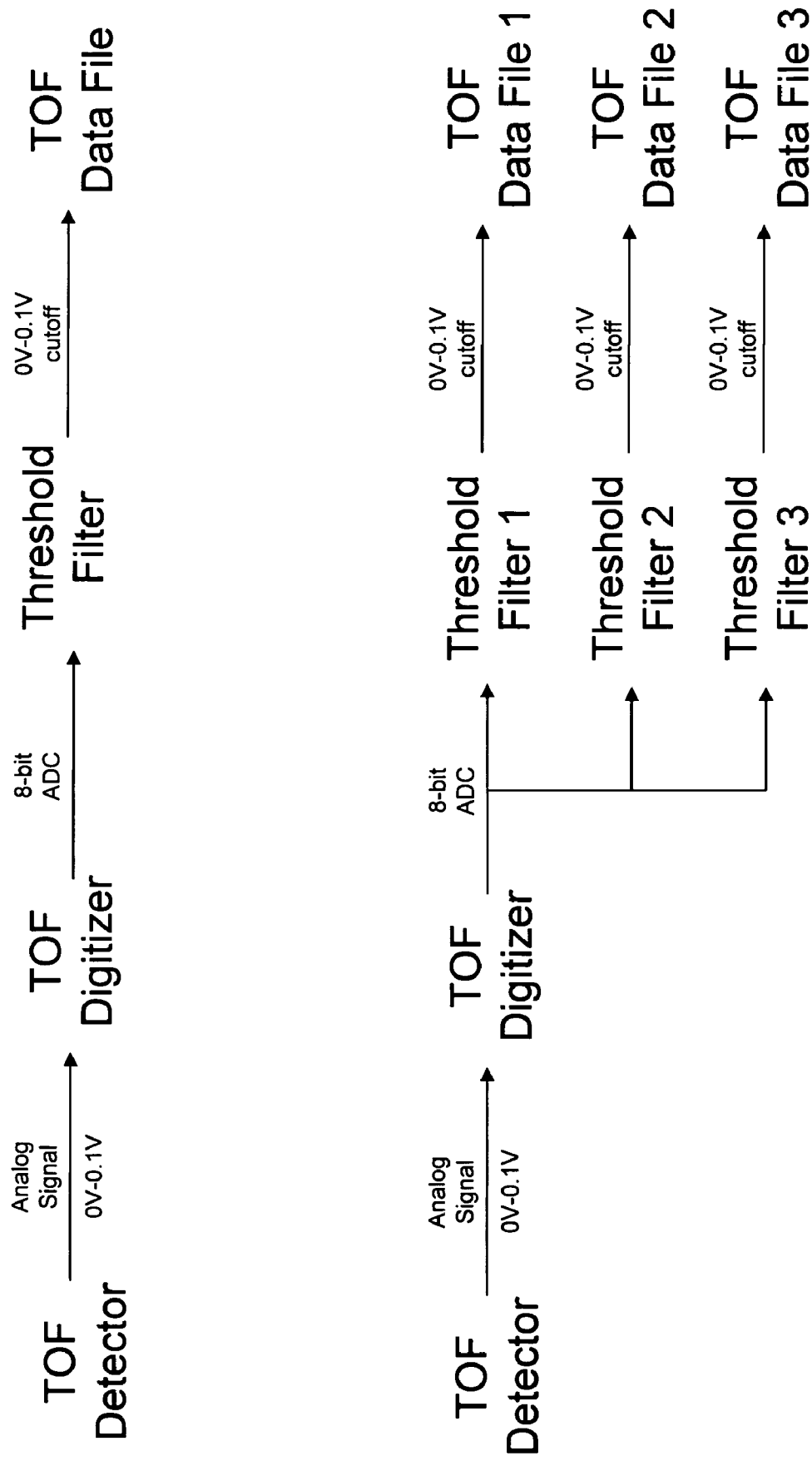

FIG. 7 shows the typical digitizer configuration (FIG. 7a) with a single threshold setting compared to a digitizer which allows multiple threshold settings to be applied simultaneously to data stream coming from the TOF digitizer (FIG. 7b).

Figure 8:
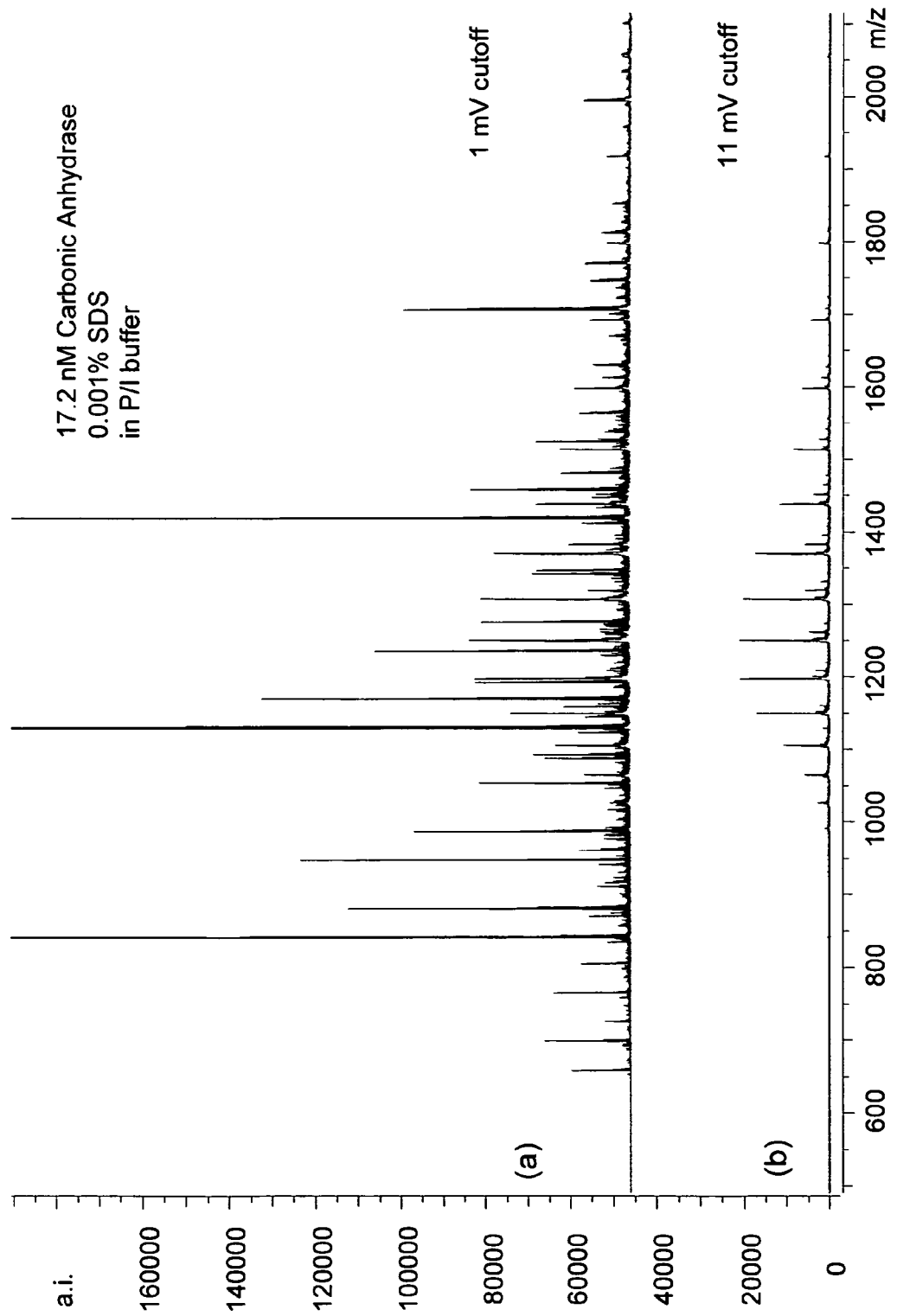

FIG. 8 shows mass spectra of carbonic anhydrase in the presence of 0.001% SDS and P/I buffer. The protein-derived signals of the spectrum obtained with a 1 mV digital signal threshold setting (FIG. 8a) are subject to considerable interference from the detergent and buffer components. In contrast, FIG. 8b indicates that the interfering components are rendered "invisible" by specifying a digital threshold setting of 11 mV.

DESCRIPTION OF EMBODIMENTS

In some embodiments of the present invention, the mass spectrometer system comprises the following components: (i) an ion detector, (ii) a digitizer that converts an analog signal to a digital signal, (iii) an analog signal transfer means for transferring an analog signal from the detector to the digitizer, and (iv) a plurality of digital threshold filters for setting a digital signal threshold which are each in digital data communication with the digitizer and in response to a digital signal input from the digitizer independently outputting a digital signal to a corresponding data file only if the digital signal input is greater than the specified digital signal threshold. In some embodiments, the analog and digital signals are voltage signals and the analog to digital converter (ADC) converts the analog voltage signal to a digital voltage signal. In some embodiments, a plurality of mass spectrometer measurements are made and the resulting plurality of data files are co-added.

In other embodiments, the mass spectrometer system comprises a (iv) single digital threshold filter instead of a plurality of digital threshold filters. The single digital threshold filter is in digital data communication with the digitizer and a corresponding data file.

In some embodiments, the mass spectrometer is a time-of-flight mass spectrometer, a quadrupole time-of-flight mass spectrometer, a linear quadrupole mass spectrometer, a linear trap mass spectrometer, an electric/magnetic sector mass spectrometer or a quadrupole ion trap mass spectrometer. In some embodiments, ions are produced by electrospray ionization (ESI).

In some embodiments, the multiply-charged analyte is a biomolecule such as, for example, a nucleic acid, a protein, a carbohydrate or a lipid. Examples of nucleic acids include, but are not limited to, RNA constructs used to screen small molecules for drug discovery and amplification products such as PCR products which can be used for genetic analyses. In some embodiments, the multiply-charged analyte is of a molecular weight of 5-500 kDa, 25-250 kDa, or 50-100 kDa.

In some embodiments, the method allows for ESI-TOF characterization of biomolecules in the presence of biomolecule stabilizing agents or matrix modifiers used in online separation techniques. Stabilizing agents include, but are not limited to, buffer salts such as phosphates for example, ampholytes, glycerol, polyethylene glycol, polypropylene glycol, reducing agents, detergents, and the like. Matrix modifiers may be any type of additive used to effect a solution matrix property advantageous to an analytical separation and may include, but are not limited to, ampholytes, detergents and buffer salts such as phosphates for example.

In some embodiments, the biomolecule stabilizing agents or matrix modifiers are singly-charged when detected by the mass spectrometer. In other embodiments, the biomolecule stabilizing agents or matrix modifiers have one or two charges.

In some embodiments, when a plurality of digital signal threshold filters are employed in the mass spectrometer system, a plurality of unique digital signal thresholds are specified in order to obtain parallel differentially filtered data streams which are stored in corresponding data files. In some embodiments, any member of the data files may be subtracted from any of the other data files to obtain a more accurate representation of a given analyte signal. These embodiments may be used to obtain a more accurate mass spectrum of a calibrant ion, or any other lower molecular weight contaminating ion by subtracting out an overlapping signal from an ion having a similar m/z but with a larger molecular mass.

In some embodiments, the methods described herein which employ multiple differentially thresholded data streams may be used in multiplexed data acquisition of a plurality of ions such as those obtained from chemical, protease or restriction digestion of proteins or nucleic acids.

In some embodiments, the methods described herein may be used to reduce the burden of level of purification of large molecular weight or multiply charged analytes such as biomolecules, for example, from stabilizing agents or matrix modifiers.

EXAMPLES

Example 1

ESI-TOF Mass Spectrometry Conditions

A Bruker Daltonics (Billerica, Mass.) MicroTOF ESI time-of-flight (TOF) mass spectrometer was used in this work. Ions from the ESI source undergo orthogonal ion extraction and are focused in a reflectron prior to detection. Ions are formed in the standard MicroTOF ESI source which is equipped with an off-axis sprayer and glass capillary. For operation in the negative ion mode, the atmospheric pressure end of the glass capillary is biased at 6000 V relative to the ESI needle during data acquisition. A counter-current flow of dry N2 is employed to assist in the desolvation process. External ion accumulation is employed to improve ionization duty cycle during data acquisition. Each ESI-TOF spectrum is comprised of 75,000 data points digitized over 75 μs. All aspects of data acquisition were controlled by the Bruker MicroTOF software package. Post processing of data was also performed using the standard Bruker software.

Example 2

PCR Conditions and Purification of Amplification Products

All PCR reactions were assembled in 50 μL reaction volumes in a 96 well microtiter plate format using a Packard MPII liquid handling robotic platform and M. J. Dyad thermocyclers (MJ research, Waltham, Mass.). The PCR reaction mix consists of 4 units of Amplitaq Gold, 1× buffer II (Applied Biosystems, Foster City, Calif.), 1.5 mM $MgCl_2$, 0.4M betaine, 800 μM dNTP mix and 250 nM of primer. The following PCR conditions were used: 95° C. for 10 min followed by 50 cycles of 95° C. for 30 sec, 50° C. for 30 sec, and 72° C. for 30 sec.

PCR products were purified using the protocols disclosed and claimed in U.S. patent application Ser. No. 10/943,344 which is commonly owned and incorporated herein by reference in entirety.

Example 3

Investigation of Detection Efficiency of Large Oligonucleotide Ions

In an attempt to optimize detection efficiency of large oligonucleotide ions, and to better understand the relationship between ion arrival statistics and mass accuracy, a detailed systematic study was designed to investigate detector response as a function of molecular weight, m/z, and charge state at the individual ion level.

In time of flight mass spectrometry ions are separated based on differences in their velocity as they traverse the flight tube. As ions strike the detector, their arrival times are recorded and subsequently converted to m/z based on the specific configuration of the spectrometer (length of flight path, accelerating voltage, geometry, etc.). It is generally accepted that for singly charged species, detector response is inversely proportional to molecular weight (velocity) and, for example in the case of MALDI, higher molecular weight species induce a smaller detection signal than lower molecular weight species. It was suspected that lower charge states (i.e. lower velocity species) induce a smaller signal than do the higher charge states (i.e. high velocity species) under the same accelerating voltages. The reduced response of high molecular weight "slow" ions can be partially ameliorated by the use of post-acceleration methods in which ions are accelerated to very high kinetic energies immediately prior to detection.

During the course of this investigation, it became immediately apparent that ions of the same nominal m/z but different molecular weights induced significantly different detector responses. The heavier, more highly charged ions consistently produced detector responses several times that of their singly charged counterparts at the same m/z. Thus, while in the TOF mass analyzer ions of the same m/z have the same velocity, ions of different molecular weigh do not have the same momentum or kinetic energy and do not induce the same signal on the detector.

This phenomenon is readily illustrated by examining spectral response as a function of the digital threshold employed to acquire mass spectra of species covering a range of molecular weights.

Unlike MALDI of large biomolecules, the multiple charging phenomenon inherent to the ESI process generally produces mass spectra in which the majority of the signals are in the same m/z range. Molecular ions from moderate to large biomolecules (1 kDa to 100 kDa) are generally detected in the 500-2000 m/z range and it is thus not at all uncommon for complex mixtures to yield spectra in which peaks of many different masses are detected at the same m/z. To characterize detector response as a function of molecular weight (charge), solutions containing analytes with molecular weight ratios of 1.0, 3.7, 11.8, 21.5, and 43 were analyzed at a range of digital thresholds. For each series, a single charge at or near m/z 1233 was used to gauge the detector response. The resulting molecular weight isopleths are plotted in FIG. 1. Importantly, at low digital signal thresholds set according to Example 4 (vide infra), the singly charged PPG ions drop in intensity at significantly lower cutoff voltages than do the higher molecular weight (charge) species. For example, at a digital signal threshold cutoff voltage of 9 mV, the signal of the PPG ions at m/z 1233 is attenuated to non-detectable levels while the 43 kDa PCR product at m/z 1233 is still detected at approximately 90% of the initial response. There is a definite trend in cutoff voltages as a function of molecular weight (charge state) suggesting that one can select a digital signal threshold to selectively detect (or not detect) species of interest.

Example 4

Digital Signal Threshold Rationale

Under the acquisition conditions routinely employed to characterize PCR products, individual scans are acquired and co-added at a rate of 75 kHz. Thus for a typical 45 second acquisition, each spectrum is comprised of 660,000 co-added individual scans. In order to reduce the shot/white noise in the co-added spectrum, the MicroTOF electronics allow one to set a digital filter threshold (voltage cutoff) such that white noise from the detector at the single or low-bit ADC count is zeroed out of each scan and only detector responses consistent with ion detection events are passed to the transient summing digitizer data system to be co-added. This concept is shown schematically in FIG. 2. FIG. 2a depicts the raw ADC output from a theoretical single scan in which a singly charged ion (ion1) strikes the detector at T1 and a large multiply charged ion (ion2) which strikes the detector at time T2. During the time intervals in which neither ion1 nor ion2 are striking the detector the ADC is picking up and digitizing detector noise generally corresponding to 1-5 bits. Because of the fast acquisition rate of the TOF and the finite ion capacity of the source, each scan is typically comprised of relatively few ion detection events and for any given ion channel, it is very unlikely that an ion will be detected in each scan. Thus, co-adding large numbers of unfiltered scans such as those depicted in FIG. 2d would result in a noise floor that increases linearly with the number of scans and a mass spectrum in which the ultimate dynamic range would be limited by the relatively high electronic noise floor.

To minimize the deleterious effects of co-adding low-bit detector noise, the MicroTOF electronics allow the user to set a cutoff voltage that has the net effect of zeroing-out low level signals that are attributed only to detector noise. As illustrated in FIG. 2c, this approach, ideally, does not affect the ADC counts for signals consistent with a singly charged ion but digitally filters each scan prior to co-adding, such that detector white noise is not co-added with the same efficiency as detector ion response. As illustrated in FIG. 2b, this concept can be taken a step further by setting the digital filter threshold such that ADC counts derived from detector noise and singly charged ions striking the detector are zeroed out prior to co-adding. Thus, with the digital threshold set at the level depicted in FIG. 2b, a singly charged ion striking the detector is "invisible" in the post-filtered ADC output and the net result is a "high pass" molecular weight (charge) filter in which low molecular weight (charge) species are not detected but high molecular weight (charge) species, which tend to be multiply-charged are still detected.

Example 5

Chemical Noise Removal by High Pass Digital Threshold Filtering

A key challenge in the analysis of large biopolymers by ESI-MS is sample purification. Low molecular weight contaminants in biopolymer solutions can have deleterious effects on the quality of ESI-MS spectra and can significantly limit the dynamic range and accuracy of the measurement. In some cases these low molecular weight "contaminants" are actually required additives as components of an on-line separations. Such additives include ampholytes used in capillary isoelectric focusing, phosphates commonly used as components of buffers used in capillary zone electrophoresis, and solution matrix modifiers used to promote micelle formation in micellar electrokinetic chromatography. Similarly, electrospray incompatible additives such as glycerol and polymers (polyethelene glycol, PPG) are often used to stabilize enzymes to be used in biochemical processes. These compounds often make their way through an entire biochemical process and end up in the mass spectrometer. A key example of the latter type of "contaminant" is the presence of high levels of polyethelene glycol and polypropylene glycol polymers in the Taq polymerase used for PCR. While typically only 1-2 µL of Taq are used in each 50 µL PCR reaction, the relatively high concentration of polymer in the presence of the relatively low concentration of PCR products (typically 10-100 nM), coupled with the fact that such polymers are ionized with high efficiency, may cause a significant chemical noise suppression issue.

FIG. 3a illustrates an example of an ESI-TOF spectrum of a 140-mer PCR product into which a contaminating amount of PPG was spiked along with relatively high levels of singly charged peptides (which serve as internal mass standards). The signal from the charge state envelope of the multiply charged strands of the PCR amplicons is confounded by the presence of the intense signal arising from the low molecular weight species. This spectrum was acquired using a "normal" digital threshold setting in which the detector white noise output from the digitizer is filtered out but the threshold is set low enough to ensure that signals from singly charged ions are captured. This spectrum is exemplary of a common situation in which a large biopolymer is analyzed in the presence of a significant chemical noise background arising from low molecular weight contaminants. As shown, such interferences can adversely affect the mass accuracy of the measurement and result in reduced spectral dynamic range.

In contrast, the ESI-TOF spectrum in FIG. 3b was acquired on the same spectrometer from the identical solution using the identical ESI source parameters and acquisitions conditions with the important exception that the spectrum in FIG. 3b was acquired at a cutoff voltage of 15 mV while the spectrum in 3a was acquired moments earlier at a cutoff voltage of 3 mV. It is clear from these spectra, and the data presented in FIG. 2 that the 15 mV cutoff setting precludes the detection of the singly charged species in the solution yet facilitates the detection of the larger, more highly charged PCR amplicons. It is evident from the spectra in FIG. 3 and the cutoff profiles in FIG. 2 that the intensity of the amplicon peaks are reduced by about 30%; importantly the peaks from the singly charged polymer and calibrants are not present in the spectrum acquired at the higher cutoff voltage and the spectrum in FIG. 3b has significantly improved signal-to-chemical noise characteristics. It is worthwhile to emphasize that, no other instrument, solution, or data processing parameters were changed between collecting the spectra in FIGS. 3a and 3b, the only difference was the digital signal threshold setting.

Indicating the applicability of the method for biomolecules other than nucleic acids, FIG. 8 shows mass spectra of carbonic anhydrase in the presence of 0.001% SDS and 25 mM Piperidine/Imidizole buffer. The protein-derived signals of the spectrum obtained with a 1 mV digital signal threshold setting are subject to considerable interference from the detergent and buffer components. In contrast, FIG. 8b indicates that the interfering components are rendered "invisible" by specifying a digital threshold setting of 11 mV.

These data indicate that in some high throughput screening and QC applications a less rigorous sample purification protocol might be employed and chemical noise can be removed via the digital filtering approach described above. Importantly, this approach allows ESI-MS analysis of large biomolecules (or noncovalent complexes) from solutions which might otherwise contain too much chemical noise to produce interpretable spectra.

Example 6

Dynamic Range Enhancement by Digital Threshold Filtering

By reducing or eliminating the chemical noise floor in addition to reducing the electronic noise floor, significant improvements in dynamic range and spectral quality are attainable. This concept is demonstrated in FIGS. 4 and 5. Shown in FIG. 4 is an expanded region of the ESI-TOF spectra from FIG. 3 in which the relatively low abundance high charge states of the PCR amplicon are detected. Note that the signals from the $(M-43H+)^{43-}$, $(M-42H+)^{42-}$, and $(M-41H+)^{41-}$ charge states are barely visible in the unfiltered spectrum (FIG. 4a) but clearly visible in the filtered spectrum (FIG. 4b). The effective signal to noise of the spectrum in FIG. 4a is defined by the signal to chemical noise ratio, while the effective signal to noise of the spectrum in FIG. 4b is defined by the signal to electronic noise ratio. For example, for the $(M-41H+)^{41-}$ charge state of the amplicon the signal to (chemical) noise in the spectrum acquired at the low cutoff threshold is approximately 2 while the signal to (electronic) noise of the spectrum acquired at the higher cutoff threshold is approximately 12. Additionally, signals from charge states $(M-40H+)^{40-}$ and $(M-39H+)^{39-}$ are not readily discernable from the chemical noise in FIG. 4a but clearly visible in FIG. 4b.

The improvement in effective dynamic range afforded by the present invention is further illustrated in FIG. 5 in which a solution containing approximately 0.5 nM PCR product in the presence of 500 nM PPG was characterized at high and low threshold settings. At the normal threshold setting the spectrum is dominated by highly abundant singly charged polymer ions and the very low level PCR products are not observed. As shown in the inset, the top spectrum is also inundated with other chemical noise components and the peak-at-every-mass background precludes the detection of the low level PCR products. When the digital signal threshold is set such that signals from singly charged species are not detected, a distinct signature for the low level amplicon is detected. This attribute has the potential to significantly improve the detection of low concentration biomolecules in solution as it is frequently the presence of low level, ubiquitous, contaminants introduced from buffer impurities, plasticware, and sample handling that define the chemical noise floor of the mass spectra and limit the applicability of ESI-MS to complex biological systems.

In addition to reducing the useful dynamic range of a mass spectrum, chemical noise and low molecular weight contaminants can have adverse affects on accurate mass measurements. As described above, ESI-MS spectra often have overlapping peaks that result from species of different molecular weights but the same m/z. This is particularly problematic for large biopolymer ions which generally produce somewhat congested spectra in which multiple charge states are observed in the 500 to 2000 m/z range. Because low molecular weight species are isotopically resolved and species above about 10 kDa are generally not, it is quite common to see a low molecular weight contaminant peak overlap with and distort an otherwise analytically useful analyte peak. An example of this is shown in FIG. 6 in which the signal from the $(M-3H+)^{3-}$ charge state of a 12-mer oligonucleotide is observed at the same m/z as the $(M-35H+)^{35-}$ charge state of a much larger 140-mer PCR product. In this case the smaller oligonucleotide is intended to serve as an internal mass standard but, as is illustrated in FIG. 6 and in the mass accuracy data in Table 1, the co-location of these signals is deleterious to both signals. First, at the 7 mV threshold it is not immediately apparent that there are two species at m/z 1233 as peaks from the isotopically resolved 12-mer mask the presence of the larger unresolved amplicon peak. Additionally, the presence of the unresolved amplicon peak distorts the peak shapes and centroids of the isotopically resolved 12-mer peaks such that the mass accuracy is compromised. When the digital threshold is set to 11 mV, the contribution to the peak from the triply charged 12-mer is substantially reduced and the presence of a high molecular weight unresolved peak is apparent. Importantly, because the aggregate signal (i.e. 12-mer and 140-mer) is captured at the 7 mV digital threshold level, and the contribution to the signal from the 140-mer can be measured at a higher digital threshold level (11 mV in this example), the signal from the 12-mer can be derived by subtracting the spectrum acquired at 11 mV from the spectrum acquired at 7 mV. The resulting spectrum exhibits a notably improved distribution (containing 5 peaks) and, perhaps more importantly, the centroided peaks yield a reduced mass measurement error across the distribution. In this example, the average mass measurement error for the five peaks was reduced from 5.9 to 1.5 ppm following the spectral subtraction.

TABLE 1

Calculated Error in m/z Measurements for 7 mV Digital Signal Threshold vs. (7 mV)-(11 mV) Digital Signal Thresholds

| Digital Signal Threshold (mV) | Peak Number | Theoretical (m/z) | Measured (m/z) | Error (ppm) |
| --- | --- | --- | --- | --- |
| 7 | 1 | 1232.5408 | 1232.5596 | −15.2512 |
| 7-11 | 1 | 1232.5408 | 1232.5449 | −3.3246 |

TABLE 1-continued

Calculated Error in m/z Measurements for 7 mV Digital Signal Threshold vs. (7 mV)-(11 mV) Digital Signal Thresholds

| Digital Signal Threshold (mV) | Peak Number | Theoretical (m/z) | Measured (m/z) | Error (ppm) |
|---|---|---|---|---|
| 7 | 2 | 1232.8752 | 1232.8809 | −4.6266 |
| 7-11 | 2 | 1232.8752 | 1232.8753 | −0.0844 |
| 7 | 3 | 1233.2095 | 1233.2005 | 7.2811 |
| 7-11 | 3 | 1233.2095 | 1233.2071 | 1.9292 |
| 7 | 4 | 1233.5437 | 1233.5452 | −1.1898 |
| 7-11 | 4 | 1233.5437 | 1233.5428 | 0.7558 |
| 7 | 5 | 1233.8780 | 1233.8764 | 1.2781 |
| 7-11 | 5 | 1233.8780 | 1233.8799 | −1.5585 |

In Table 1, 7-11 indicates that a spectrum obtained with a digital signal threshold setting of 11 mV was subtracted from a spectrum obtained with a digital signal threshold setting of 7 mV.

Example 7

Spectral Subtraction and Ion Partitioning: Obtaining "Slices of Ions"

In accordance with the present invention, the experiments illustrated in FIGS. 3-5 illustrate that the digital thresholding method described above allows for the detection of large multiple charged biomolecular ions in such a manner so as to render low molecular weight species "invisible" (based on digital thresholding) while the data presented in FIG. 6 illustrates a method by which low molecular weight species can be analyzed in such a manner so as to make large multiple charged biomolecular ions "invisible" (by digital thresholding and spectral subtraction). The results from the relatively simple subtraction described in Example 6 lay the foundation for more sophisticated digital thresholding schemes in which multiple "slices" of a complex ion population can be analyzed simultaneously with the effective result being a multidimensional detection configuration in which ions are simultaneously measured.

In this work all of the high threshold/low threshold comparisons were made by multiple measurements of the same analyte solution acquired under identical instrument conditions except the digital threshold was varied. This was done out of necessity because, as illustrated in FIG. 7a, the basic system architecture of the Bruker MicroTOF consists of a single data stream from the detector to the digitizer for which a single threshold level is applied to the data stream prior to co-adding of scans. As sample throughput is a key driver in many laboratories, requiring each sample to be analyzed two (or more) times at different digital thresholds may not be feasible.

In accordance with the present invention and as a means of circumventing this problem, the alternative digitization scheme illustrated in FIG. 7b indicates that output from the ADC can be split to multiple parallel data streams, each of which is subjected to a different digital threshold. By subtracting spectra acquired at different digital thresholds, one could obtain a mass spectrum for any "slice" of the ion population. This would allow one to perform digital thresholding on a very complex mass spectrum and evaluate a range of molecular weights (charges) independent of other, potentially interfering, ion populations such as for example, a restriction digest of a nucleic acid or a protease digest of a protein.

Another example could be a biomolecule such as a nucleic acid or a protein having a non-covalently-bound small molecule.

Having multiple variably-thresholded mass spectra derived from the identical digitization event would guarantee perfect subtraction of spectral features and would eliminate potential artifacts which may arise from spectral drift over the course of acquiring multiple spectra. Importantly, this also means that one could introduce low molecular weight internal mass standards (calibrants) to very accurately calibrate the m/z axis (e.g. the PPG series in FIG. 3a) but derive accurate mass measurements of biomolecular analytes from peaks that are never "stepped on" by low molecular weight species (e.g. the digitally thresholded spectrum in FIG. 3b).

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of selective ion filtering of a mass spectrum, comprising the steps of:
   a) generating an analog signal of multiply-charged and singly-charged ions from mass spectrometric analysis of a sample comprising at least one biomolecule;
   b) converting said analog signal to a digital signal;
   c) generating one or more outputs by filtering said digital signal with a plurality of filters configured to exclude ions based upon a plurality of predetermined cutoff levels;
   d) storing said one or more outputs to one or more data files; and
   e) providing a mass spectrum, wherein said mass spectrum displays one or more of said data files.

2. The method of claim 1, wherein at least one of said plurality of filters is configured to exclude singly-charged ion signals.

3. The method of claim 1, wherein said biomolecule is a nucleic acid, a peptide, a protein, a lipid, or a carbohydrate biomolecule.

4. The method of claim 1, wherein said biomolecule comprises a non-covalently-bound small molecule.

5. The method of claim 1, wherein said singly-charged ions are biomolecule stabilizer additives or matrix-modifying additives.

6. The method of claim 5, wherein said biomolecule stabilizer additives are selected from the group consisting of polyethylene glycol, glycerol, reducing agents, detergents, buffer salts, and any combination thereof.

7. The method of claim 5, wherein said matrix-modifying additives are selected from the group consisting of ampholytes, detergents, buffer salts, and any combination thereof.

8. The method of claim 1, wherein said analog signal is an analog voltage signal and said digital signal is a digital voltage signal.

9. The method of claim 1, wherein said mass spectrometric analysis is selected from the group consisting of time-of-flight mass spectrometric analysis, quadrupole time-of-flight mass spectrometric analysis, linear quadrupole mass spectrometric analysis, linear trap mass spectrometric analysis, electric/magnetic sector mass spectrometric analysis, and quadrupole ion trap mass spectrometric analysis.

10. The method of claim 1, wherein said mass spectrum is generated by co-adding two or more of said data files.

11. A method for determining the molecular mass of a plurality of analytes in a mixture, comprising the steps of:
 a) providing a mass spectrometer, comprising:
  i) an ion detector;
  ii) an analog signal transfer means configured to transfer said analog signal from said detector to a digitizer configured to convert said analog signal to a digital signal; and
  iii) a plurality of filters in digital data communication with said digitizer configured to provide a plurality of outputs in response to a plurality of inputs from said digitizer;
 b) providing a mass spectrometeric analysis of said mixture, wherein said filters differentially filter inputs arising from said plurality of said analytes, and wherein said plurality of outputs corresponding to said plurality of inputs greater than predetermined corresponding cutoff levels are stored on a plurality of corresponding data files; and
 c) determining the molecular mass of a plurality of analytes in said mixture by analyzing said plurality of data files wherein the molecular mass of at least one member of said plurality of analytes is contained therein.

12. The method of claim 11, wherein said analyzing said plurality of data files further comprises mathematical subtraction of at least one member of said plurality of data files from at least one other member of said plurality of data files.

13. The method of claim 11, wherein said plurality of analytes comprises singly-charged ions and multiply-charged ions.

14. The method of claim 13, wherein said multiply-charged ions are biomolecules.

15. The method of claim 14, wherein said biomolecules comprise non-covalently-bound small molecules.

16. The method of claim 14, wherein said biomolecules are nucleic acids, peptides, proteins, lipids or carbohydrates.

17. The method of claim 13, wherein the singly-charged ions are biomolecule stabilizer additives or matrix-modifying additives.

18. The method of claim 17, wherein said stabilizer additives are selected from the group consisting of polyethylene glycol, glycerol, reducing agents, detergents, buffer salts, and any combination thereof.

19. The method of claim 17, wherein said matrix-modifying additives are selected from the group consisting of ampholytes, detergents, buffer salts, and any combination thereof.

20. The method of claim 11, wherein said analog signal is an analog voltage signal and said digital signal is a digital voltage signal.

21. The method of claim 11, wherein the mass spectrometer is a time-of-flight mass spectrometer, a quadrupole time-of-flight mass spectrometer, a linear quadrupole mass spectrometer, a linear trap mass spectrometer, an electric/magnetic sector mass spectrometer, or a quadrupole ion trap mass spectrometer.

22. A method of calibrating a mass spectrum of an analyte, comprising:
 a) providing a first cutoff level for a first member of a plurality of filters on a mass spectrometer, wherein said mass spectrometer comprises:
  i) an ion detector;
  ii) a digitizer configured to convert an analog signal to a digital signal;
  iii) an analog signal transfer means configured to transfer an analog signal from said detector to said digitizer; and
  iv) a plurality of filters in digital data communication with said digitizer configured to provide a plurality of signal outputs in response to a plurality of inputs from said digitizer, wherein said filters differentially filter inputs, and wherein said plurality of outputs corresponding to said plurality of inputs greater than predetermined corresponding cutoff levels are stored in a plurality of corresponding data files, and wherein said first cutoff level is predetermined such that said output to a first data file comprises signals from said analyte and a calibrant ion;
 b) providing a second cutoff level for a second member of said plurality of filters wherein said second cutoff level is predetermined such that said output to a second data file comprises a signal from said analyte but not from said calibrant ion;
 c) subtracting said second data file from said first data file to obtain a calibration data file comprising a signal from said calibrant ion but not from said analyte; and
 d) calibrating the mass spectrum of said analyte from said calibration data file.

23. The method of claim 22, wherein said calibrant ion is a nucleic acid, a peptide or a small molecule.

24. The method of claim 22, wherein said analyte is a biomolecule.

25. The method of claim 24, wherein said biomolecule is a nucleic acid, a peptide, a protein, a lipid or a carbohydrate.

26. The method of claim 24, wherein said biomolecule comprises a non-covalently-bound small molecule.

27. The method of claim 22, wherein said analog signal is an analog voltage signal and said digital signal is a digital voltage signal.

28. The method of claim 22 wherein said mass spectrometer is a time-of-flight mass spectrometer, a quadrupole time-of-flight mass spectrometer, a linear quadrupole mass spectrometer, a linear trap mass spectrometer, an electric/magnetic sector mass spectrometer, or a quadrupole ion trap mass spectrometer.

29. A system, comprising:
 a) a mass spectrometer, comprising:
  i) a biomolecule ion detector;
  ii) a digitizer configured to convert an analog signal to a digital signal;
  iii) an analog signal transfer means configured to transfer an analog signal from said detector to said digitizer; and
  iv) a plurality of filters with a plurality of corresponding cutoff levels in parallel electronic communication with said digitizer, wherein said filters generate a digital voltage signal output in response to a digital voltage signal input from said digitizer greater than a predetermined corresponding cutoff level;
 b) a plurality of data files; and
 c) a plurality of parallel output transfer means in digital data communication with at least one of said filters, and a corresponding data file contained in said plurality of data files.

30. The method of claim 29, wherein at least one of said plurality of filters is configured to exclude singly-charged ion signals.

31. The method of claim 29, wherein said biomolecule is a nucleic acid, a peptide, a protein, a lipid, or a carbohydrate biomolecule.

32. The method of claim 29, wherein said biomolecule comprises a non-covalently-bound small molecule.

33. The method of claim 30, wherein said singly-charged ions are biomolecule stabilizer additives or matrix-modifying additives.

34. The method of claim 30, wherein said biomolecule stabilizer additives are selected from the group consisting of polyethylene glycol, glycerol, reducing agents, detergents, buffer salts, and any combination thereof.

35. The method of claim 34, wherein said matrix-modifying additives are selected from the group consisting of ampholytes, detergents, buffer salts, and any combination thereof.

36. The system of claim 29, wherein said analog signal is an analog voltage signal and said digital signal is a digital voltage signal.

37. The system of claim 29, wherein said mass spectrometer is a time-of-flight mass spectrometer, a quadrupole time-of-flight mass spectrometer, a linear quadrupole mass spectrometer, a linear trap mass spectrometer, an electric/magnetic sector mass spectrometer, or a quadrupole ion trap mass spectrometer.

38. The method of claim 29, wherein said plurality of data files are data files on a computer readable medium.

* * * * *

UNITED STATES PATENT AND TRADEMARK OFFICE
CERTIFICATE OF CORRECTION

| | | |
|---|---|---|
| PATENT NO. | : 7,714,275 B2 | Page 1 of 1 |
| APPLICATION NO. | : 11/136134 | |
| DATED | : May 11, 2010 | |
| INVENTOR(S) | : Hofstadler et al. | |

It is certified that error appears in the above-identified patent and that said Letters Patent is hereby corrected as shown below:

Column 14, lines 62 and 65; column 15, lines 1, 3, 6, and 10; and column 16, line 10, each occurrence of "The method" should read --The system--.

Signed and Sealed this

Fifteenth Day of June, 2010

David J. Kappos
*Director of the United States Patent and Trademark Office*